(12) United States Patent
Hurley et al.

(10) Patent No.: US 11,141,064 B2
(45) Date of Patent: Oct. 12, 2021

(54) SYSTEMS AND METHODS FOR RAPID WIDE FIELD ILLUMINATION SCANNING FOR IN VIVO SMALL ANIMAL FLUORESCENCE TOMOGRAPHIC IMAGING

(71) Applicant: PerkinElmer Health Sciences, Inc., Waltham, MA (US)

(72) Inventors: William Hurley, Providence, RI (US); Ali Behrooz, Waltham, MA (US); Michael Meltzer, Norwood, MA (US); Andrew Wilson, Laguna Beach, CA (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 623 days.

(21) Appl. No.: 15/654,442

(22) Filed: Jul. 19, 2017

(65) Prior Publication Data

US 2019/0021602 A1    Jan. 24, 2019

(51) Int. Cl.
*A61B 5/00* (2006.01)
*G01N 21/64* (2006.01)
(Continued)

(52) U.S. Cl.
CPC .......... *A61B 5/0071* (2013.01); *A61B 5/0062* (2013.01); *A61B 5/0073* (2013.01);
(Continued)

(58) Field of Classification Search
CPC ... A61B 5/0071; A61B 5/0073; A61B 5/0062; A61B 6/5235; G02B 19/0052;
(Continued)

(56) References Cited

U.S. PATENT DOCUMENTS 5,307,096 A   4/1994  Baroth et al.
7,905,597 B2  3/2011  Tsukada et al.
(Continued)

FOREIGN PATENT DOCUMENTS

DE   102004034978 A1   2/2006
EP       1797818 A2    6/2007
(Continued)

OTHER PUBLICATIONS

Klaser, Jacob. "Labe III Laser Beam Properties". MSU ECE, East Lansing, MI, 2008. (Year: 2008).*
(Continued)

*Primary Examiner* — Sean D Mattson
(74) *Attorney, Agent, or Firm* — Banner & Witcoff, Ltd.

(57) ABSTRACT

Presented herein are systems and methods for tomographic imaging that provide for rapid illumination of multiple excitation locations across a large field of view by one or more beams of excitation light from one or more excitation sources. The approaches described herein utilize a galvanometer optical scanner to scan a beam of excitation light through a plurality of locations across a scan region corresponding to the field of view to be imaged. In certain embodiments, the systems and methods described herein utilize beams of excitation light with specifically tailored shapes to maintain small spot sizes across the large scan region. The ability to scan over a large region while still maintaining small spot sizes provided by the approaches described herein allows for accurate, high-resolution tomographic imaging of large or multiple subjects, thereby expanding the capabilities of tomographic imaging systems.

36 Claims, 19 Drawing Sheets
(1 of 19 Drawing Sheet(s) Filed in Color)

(51) Int. Cl.
  *G02B 26/10* (2006.01)
  *G02B 19/00* (2006.01)
  *G06T 7/00* (2017.01)
  *G06T 11/00* (2006.01)
  *G01N 21/47* (2006.01)

(52) U.S. Cl.
  CPC ..... *G01N 21/6456* (2013.01); *G02B 19/0014* (2013.01); *G02B 19/0052* (2013.01); *G02B 26/101* (2013.01); *G02B 26/105* (2013.01); *G06T 7/0012* (2013.01); *G06T 11/003* (2013.01); *A61B 2503/40* (2013.01); *G01N 21/4795* (2013.01); *G01N 2201/10* (2013.01)

(58) Field of Classification Search
  CPC .............. G02B 19/0014; G02B 26/101; G02B 26/105; G01N 21/6456; G01N 21/4795; G01N 2201/10; G06T 11/003; G06T 7/0012
  See application file for complete search history.

(56) References Cited

U.S. PATENT DOCUMENTS

| | | | |
|---|---|---|---|
| 2002/0062202 A1 | 5/2002 | Arai | |
| 2003/0105195 A1 | 6/2003 | Holcomb et al. | |
| 2004/0010375 A1* | 1/2004 | Schomaker | A61B 5/0059 702/19 |
| 2004/0089817 A1 | 5/2004 | Long et al. | |
| 2006/0062202 A1 | 3/2006 | Oesterling et al. | |
| 2007/0189664 A1* | 8/2007 | Andersen | A61B 3/0008 385/25 |
| 2007/0206192 A1 | 9/2007 | Fomitchov et al. | |
| 2007/0274580 A1* | 11/2007 | Ntziachristos | A61B 5/0073 382/131 |
| 2009/0018451 A1* | 1/2009 | Bai | A61B 5/0073 600/476 |
| 2009/0021746 A1* | 1/2009 | Toida | A61B 5/0066 356/484 |
| 2009/0133167 A1* | 5/2009 | Yakushevska | H01J 37/263 850/3 |
| 2009/0149705 A1 | 6/2009 | Tani et al. | |
| 2010/0078576 A1 | 4/2010 | Ntziachristos et al. | |
| 2011/0096967 A1* | 4/2011 | Oda | H04N 5/2254 382/128 |
| 2013/0015370 A1* | 1/2013 | Damaskinos | G01N 21/6452 250/459.1 |
| 2014/0029013 A1 | 1/2014 | Yoshii et al. | |
| 2015/0346483 A1* | 12/2015 | Ehrmann | G02B 26/101 219/121.85 |
| 2016/0147081 A1* | 5/2016 | Kilcher | G02B 27/40 359/13 |
| 2016/0290927 A1* | 10/2016 | Buczkowski | G01N 21/6489 |

FOREIGN PATENT DOCUMENTS

| | | |
|---|---|---|
| EP | 03165903 A1 | 5/2017 |
| JP | 10-300443 A | 11/1998 |
| JP | H10300443 A | 11/1998 |
| JP | 11-326188 A | 11/1999 |
| JP | 2007-528500 A | 10/2007 |
| JP | 2008-196970 A | 8/2008 |
| JP | 2013-156286 A | 8/2013 |
| JP | 2014-025701 A | 2/2014 |
| WO | 2004/001402 A1 | 12/2003 |
| WO | 2008132325 A2 | 11/2008 |

OTHER PUBLICATIONS

Oct. 11, 2018—(WO) International Search Report and Written Opinon—App PCT/US2018/042723.
Apr. 4, 2019—(WO) International Search Report and Written Opinion—App PCT/US2018/056451.
English language abstract of JP 2013-156286.
English language abstract of JP 11-326188.
English language abstract of JP 2008-196970.
Feb. 17, 2021—U.S. Non-Final Office Action—U.S. Appl. No. 16/163,094.

* cited by examiner

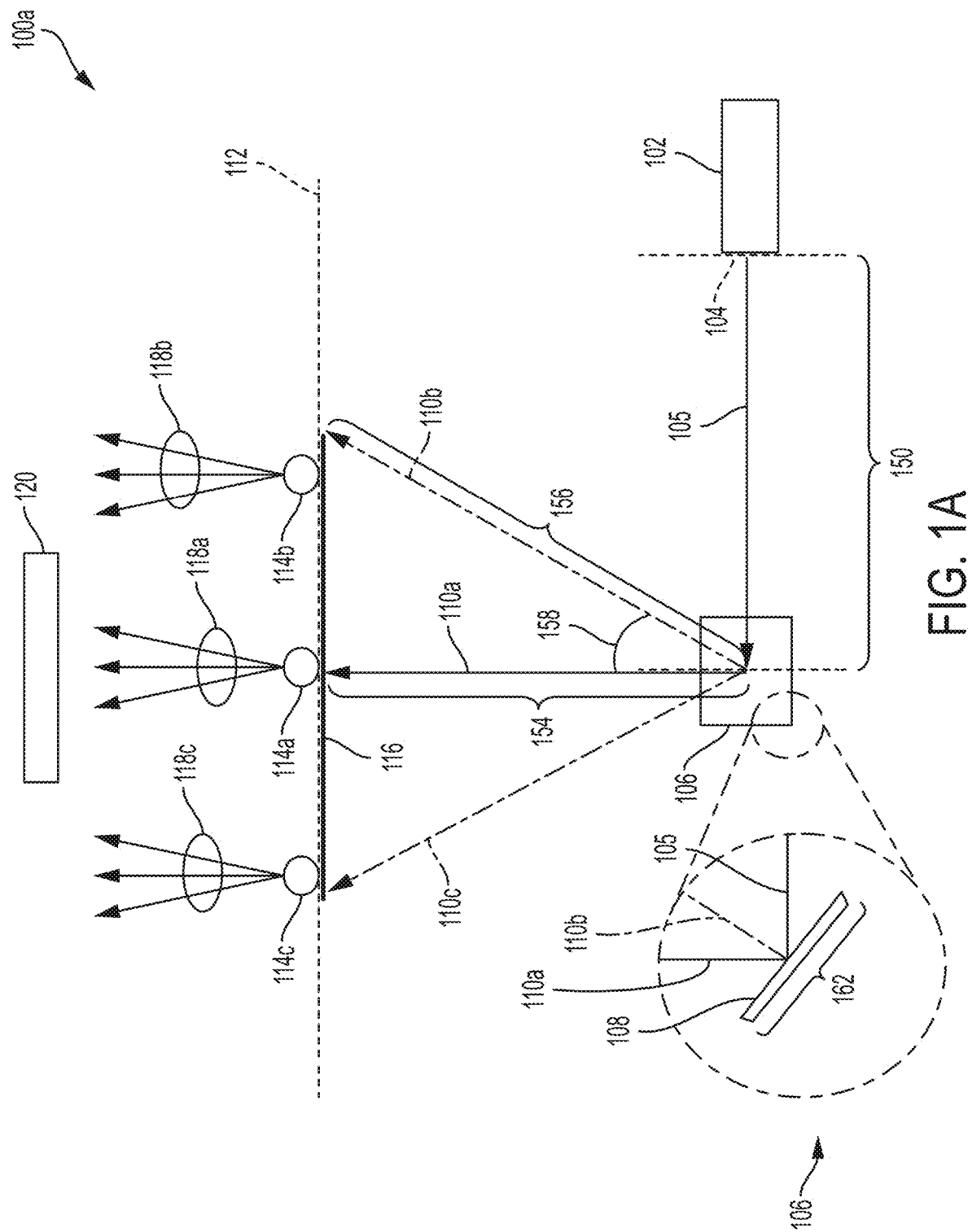

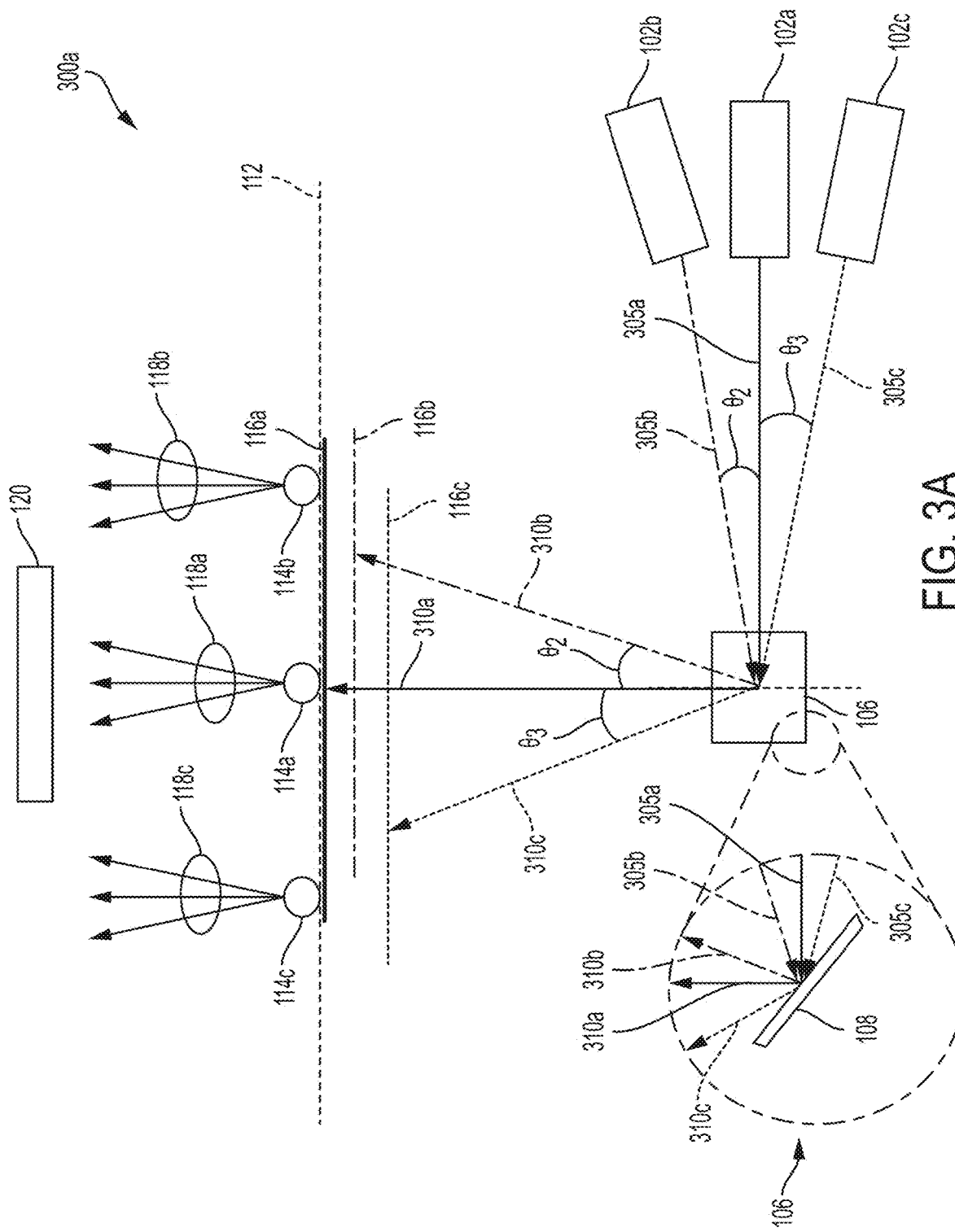

$[y - W_{bw}/2]/(d_2 - d_1)/2 = tan\phi$ $2y <= W_{max}$ (e.g., 1 mm)

$[W_{max}/2 - W_{bw}/2]/(d_2 - d_1)/2 = tan\phi$ $[W_{max} - W_{bw}]/(d_2 - d_1) > tan\phi$ $[y - W_{bw}/2]/(d_2 + d_0) = \tan\phi$ $2y <= W_{max}$ (e.g., 1 mm)

$[W_{max}/2 - W_{bw}/2]/(d_2 + d_0) = \tan\phi$ $[W_{max} - W_{bw}]/2(d_2 + d_0) > \tan\phi$

SYSTEMS AND METHODS FOR RAPID WIDE FIELD ILLUMINATION SCANNING FOR IN VIVO SMALL ANIMAL FLUORESCENCE TOMOGRAPHIC IMAGING

FIELD OF THE INVENTION

This invention relates generally to systems and methods for imaging. More particularly, in certain embodiments, the invention relates to systems and methods for rapid tomographic imaging over a wide field of view.

BACKGROUND OF THE INVENTION

In vivo imaging of small animals is performed by a large community of investigators in various fields, e.g., oncology, infectious disease, and drug discovery. There is a wide array of technologies directed to in vivo imaging of animals—for example, bioluminescence, fluorescence, tomography, and multimodal imaging technologies.

Many imaging modalities are tomographic approaches. Tomography is based on detection of light transmitted through or emanating from a sample to obtain images or infer the optical properties of the sample under study. For example, tomographic imaging can be used to reconstruct a map of tissue absorption within a region of interest of a subject under study. In other applications, tomographic imaging is used to generate a map of the spatial distribution of a probe, such as a fluorescent emitter, that is present in the region of interest. Tomographic imaging thus allows construction of detailed images of internal structures of objects, and distribution of a probe within a region of interest of a subject, in a non-invasive fashion.

Optical tomographic imaging can provide valuable information, relevant to analysis of biological processes within a subject under study, that cannot be obtained from non-optical imaging techniques such as micro-CT or magnetic resonance imaging (MRI). For example, maps of tissue absorption at optical wavelengths are capable of providing biological functional information related to hemoglobin concentration and tissue oxygenation state, which can be used to detect certain types of tumors. In addition, optical absorption additionally provides improved contrast for localizing certain organs, such as the heart, in comparison with X-ray imaging or MRI techniques.

Optical tomography can also be used to map the spatial distribution of an administered or endogenous light emitting probe, such as a fluorescent or bioluminescent probe. For example, fluorescent probes absorb light propagating inside of an object and emit light at a longer wavelength (lower energy) than the absorbed light inside of the object, allowing non-invasive, in vivo investigation of functional and molecular signatures in whole tissues of animals and humans. Fluorescence optical tomography systems thereby provide for molecular imaging, which can be used to visually indicate molecular abnormalities that are the basis of a disease, rather than just imaging the anatomical structures in the area of suspected molecular abnormalities, as with conventional imaging approaches. Specific imaging of molecular targets provides earlier detection and characterization of a disease, as well as earlier and direct molecular assessment of treatment efficacy. An illustrative fluorescence optical tomography system is described in U.S. Patent Application Publication No. US2004/0015062, the text of which is incorporated by reference herein, in its entirety.

In optical tomographic imaging, multiple locations within a region (e.g., a subject; e.g., a region of interest within a subject) to be imaged are illuminated with excitation light. In fluorescence imaging applications, fluorescent species that are within a given location illuminated by the excitation light absorb the excitation light and emit fluorescent light, which is detected by one or more detectors. In this manner, detector signals representing the emitted fluorescent light are recorded for each of the multiple illumination locations. Data corresponding to the detected fluorescent light for each of the illumination locations is used as input in tomographic reconstruction techniques that reconstruct a distribution of fluorescent emitters within the region of the object. Effectively imaging a particular region of an object requires illuminating a sufficient number and density of locations within the region in order to provide adequate data for tomographic reconstruction.

Accordingly, there exists a need for improved systems and methods for tomographic imaging that are capable of rapidly illuminating a plurality of locations within a wide field of view comprising one or more objects to be imaged. Such systems and methods are of particular relevance to in vivo small animal tomographic imaging.

SUMMARY OF THE INVENTION

Presented herein are systems and methods for tomographic imaging that provide for rapid illumination of multiple excitation locations across a wide field of view by one or more beams of excitation light from one or more excitation sources. The approaches described herein utilize a galvanometer optical scanner to scan a beam of excitation light through a plurality of locations across a scan region corresponding to the field of view to be imaged. In certain embodiments, the systems and methods described herein utilize beams of excitation light with specifically tailored shapes to maintain small spot sizes across the large scan region. The ability to scan over a large region while still maintaining small spot sizes provided by the approaches described herein allows for accurate, high-resolution tomographic imaging of large or multiple subjects, thereby expanding the capabilities of tomographic imaging systems. For example, in certain embodiments, the tomographic imaging approaches described herein allow for multiple subjects, such as multiple small animals to be quickly imaged together, thereby facilitating in vivo tomographic imaging of small animals.

Notably, in certain embodiments, the beam shaping approaches described herein allow for a wide variety of high powered lasers, with output powers on the order of (e.g., greater than or approximately equal to) 100 mW to be used. In particular, in certain embodiments, a beam shaping approach that utilizes a focused, rather than a collimated beam of excitation light is used. Many high powered lasers emit highly divergent beams of excitation light from a large output area that, accordingly, are challenging to collimate. By overcoming this challenge, the beam shaping approaches described herein provide for increased flexibility in terms of the types of excitation sources (e.g., lasers) that can be used for tomographic imaging. This provides several advantages.

For example, high powered lasers are advantageous for tomographic imaging of thick objects (e.g., subjects; e.g., small animals), as they allow sufficient power to be delivered to locations deep within the object in order to excite fluorescent species located there. This is especially relevant for objects (e.g., subjects; e.g., small animals) comprising highly absorptive and/or scattering (e.g., diffuse) media, such as tissue, in which the beam of excitation light is significantly attenuated as it propagates through the object.

Moreover, by allowing a wide variety of high powered lasers—not just those that can be readily collimated—to be used, the approaches described herein greatly increase the range of excitation wavelengths that can be used for imaging. The wavelength at which a particular laser emits cannot be selected arbitrarily, but instead is dependent in a complex fashion on a range of interdependent properties of the laser, such as the laser cavity type, the particular gain media used, and a given pumping scheme. Accordingly, various types of lasers produce excitation light at a limited, discrete set of wavelengths. For example, while fiber lasers can, in certain cases, produce adequately collimated beams of excitation light, they utilize limited set of elements (e.g., rare earth elements) as gain media and, accordingly, are limited to emitting light at a limited set of wavelengths in the near-infrared spectral region. Accordingly, the ability to accommodate a variety of types of excitation sources dramatically facilitates imaging a variety of fluorescent probes that are excitable via a variety of excitation wavelengths.

The flexibility in the range of wavelengths of excitation light that can be used in the tomographic imaging systems and methods described herein also facilitates multi-spectral imaging. In certain embodiments, multi-spectral imaging involves illuminating one or more objects with a plurality of beams of excitation light, each having a distinct wavelength. In certain embodiments, each beam of excitation light thus excites, and causes fluorescent emission from a distinct fluorescent species within the one or more objects. Accordingly, by successively performing tomographic imaging at each excitation wavelength, tomographic images representing the distribution of each of a plurality of fluorescent species within the one or more subjects can be obtained. This allows, for example, studies involving co-location of multiple types of cells and/or proteins (e.g., each type labelled with a different fluorescent probe) to be performed. Such studies are highly relevant for understanding mechanisms of various diseases and their treatment.

In certain embodiments, the tomographic imaging approaches described herein further facilitate multi-spectral imaging by providing for multiple excitation sources to be incorporated into a single system and switched between in a robust and efficient manner. In particular, in certain embodiments each of a plurality of excitation sources is aligned such its respective beam of excitation light is directed towards the galvanometer optical scanner along a corresponding optical path that is offset from the others by a corresponding offset angle. This allows the multiple excitation sources to be mounted in fixed positions, and avoids the need to use motorized stages to switch between excitation sources—an approach which, notably, in addition to being slow and complex, is prone misalignment via routine use over time and/or as a result of mechanical vibrations. Combining the ability to rapidly switch between, and rapidly scan, multiple high powered excitation sources greatly facilitates multi-spectral imaging applications.

In one aspect, the invention is directed to a system for fast scanning of excitation light over a wide field of view for tomographic imaging of one or more subjects positioned across an object plane, the system comprising: (a) an excitation source operable to emit a beam of excitation light (e.g., for excitation of a fluorescent species within the one or more subjects), wherein the excitation source is aligned to direct the beam of excitation light along an optical path from an output (e.g., a distal end of a fiber of a fiber coupled source or a fiber laser; e.g., a laser aperture of a free space laser) of the excitation source to a galvanometer optical scanner comprising one or more rotating galvanometer mirrors; (b) the galvanometer optical scanner, wherein the galvanometer optical scanner is aligned and operable to direct the beam of excitation light to a plurality of locations (e.g., discrete excitation locations) within a scan region of the object plane via reflection by the one or more rotating galvanometer mirrors, such that as the one or more galvanometer mirrors is/are rotated, the beam of excitation light is scanned across the scan region [e.g., directed towards a plurality of discrete excitation locations within the scan region (e.g., one at a time)], thereby providing for illumination of the one or more subjects positioned across the object plane; (c) one or more detectors aligned and operable to detect fluorescent light emitted from one or more fluorescent species within the one or more subjects as a result of excitation by the excitation light [e.g., as a result of excitation by the beam of excitation light directed towards each of the plurality of discrete excitation locations, e.g., one or more detectors aligned and operable to detect a fluorescence emission image (e.g., 2D image) corresponding to each of the discrete excitation locations]; (d) a processor; and (e) a memory having instructions stored thereon, wherein the instructions, when executed by the processor cause the processor to: receive and/or access data corresponding to the detected fluorescent light [e.g., the data comprising a fluorescence emission signal (e.g., image, e.g., 2D image) detected following excitation by excitation light directed towards each of a plurality of discrete excitation locations across the scan region]; and obtain (e.g., compute) one or more tomographic images of the one or more subjects using the data corresponding to the detected fluorescent light (e.g., by performing tomographic reconstruction).

In certain embodiments, the galvanometer optical scanner is positioned a specific distance, measured along a minimal length optical path from the galvanometer optical scanner to a location within the scan region (e.g., a central location of the scan region), to produce a scan region of a desired size, based on one or more maximal rotational angles of the one or more galvanometer mirrors.

In certain embodiments, the desired size of the scan region along a first dimension and/or a second dimension is at least 100 mm (e.g., at least 150 mm; e.g., at least 200 mm). In certain embodiments, the desired size of the scan region along a first dimension and/or a second dimension is from 100 to 200 mm (e.g., from 100 to 150 mm; e.g., approximately 140 mm).

In certain embodiments, a minimal distance along a minimal length optical path from the galvanometer optical scanner to a location within the scan region at least 100 mm (e.g., at least 150 mm; e.g., at least 200 mm). In certain embodiments, the minimal distance along the minimal length optical path from the galvanometer optical scanner to a location within the scan region is from 150 to 250 mm (e.g., approximately 200 mm).

In certain embodiments, the excitation source is operable to emit the beam of excitation light from its output as a focused beam that converges as it travels (i) towards the galvanometer optical scanner and (ii) from the galvanometer optical scanner to the object plane [e.g., such that a spot size (e.g., diameter) of the beam of excitation light at the object plane is smaller than an initial spot size (e.g., diameter) of the beam of excitation light at the output of the excitation source].

In certain embodiments, the focused beam of excitation light emitted from the output of the excitation source has a spot size less than or approximately equal to 1 mm at all locations within the scan region.

In certain embodiments, the focused beam of excitation light emitted from the output of the excitation source has a half-angle divergence, φ, such that $$\tan(\varphi) < \frac{w_{max} - w_{bw}}{d_2 - d_1},$$

wherein: $w_{max}$ is an upper bound for a desired spot size of the beam of excitation light within the scan region (e.g., approximately 1 mm, e.g., a scattering length of the excitation light within a diffuse media (e.g., tissue) of a subject to be imaged), $w_{bw}$ is a spot size of the beam of excitation light at its beam waist location, $d_1$ is a minimal distance measured along a minimal length optical path from the galvanometer optical scanner to a location within the scan region (e.g., measured from the galvanometer optical scanner to a central location of the scan region), and $d_2$ is a maximal distance along a maximal length optical path from the galvanometer optical scanner to a location within the scan region (e.g., measured from the galvanometer optical scanner to a location at a corner of the scan region; e.g., wherein $d_2$ is greater than $d_1$).

In certain embodiments, $d_1$ is at least 100 mm (e.g., at least 150 mm; e.g., at least 200 mm). In certain embodiments, $d_1$ is less than 300 mm (e.g., less than 250 mm). In certain embodiments, $d_1$ is from 100 mm to 500 mm (e.g., from 150 to 250 mm; e.g. from 200 to 250 mm; e.g. from 220 to 250 mm). In certain embodiments, $d_2$ is at least 100 mm (e.g., at least 150 mm; e.g., at least 200 mm) and greater than $d_1$. In certain embodiments, $d_2$ is less than 500 mm (e.g., less than 250 mm) and greater than $d_1$. In certain embodiments, $d_2$ is from 50 to 500 mm (e.g., from 100 to 250 mm; e.g. from 150 to 250 mm; e.g., from 220 to 250 mm) and greater than $d_1$. In certain embodiments, $w_{max}$ is less than or equal to 2 mm (e.g., less than or equal to 1.5 mm; e.g., less than or equal to 1 mm). In certain embodiments, $w_{max}$ is approximately 1 mm. In certain embodiments, $w_{max}$ is approximately 0.5 mm.

In certain embodiments, a half-angle divergence of the focused beam of excitation light emitted from the output of the excitation source is less than or equal to 25 mrad (e.g., less than or equal to 20 mrad; e.g., less than or equal to 15 mrad).

In certain embodiments, the excitation source is operable to emit the beam of excitation light from its output as a collimated beam that diverges (e.g., diverges slowly) as it travels (i) towards the galvanometer optical scanner and (ii) from the galvanometer optical scanner to the object plane.

In certain embodiments, the collimated beam of excitation light emitted from the output of the excitation source has a spot size less than or approximately equal to 1 mm in diameter at all locations within the scan region.

In certain embodiments, the collimated beam of excitation light emitted from the output of the excitation source has a half-angle divergence, φ, such that $$\tan(\varphi) < \frac{w_{max} - w_{bw}}{2(d_0^{(1)} + d_2)},$$

wherein: $w_{max}$ is an upper bound for a desired spot size of the collimated beam of excitation light within the scan region (e.g., approximately 1 mm, e.g., a scattering length of the excitation light within a diffuse media (e.g., tissue) of a subject to be imaged), $w_{bw}$ is a spot size of the beam of the collimated beam of excitation light its beam waist location [e.g., wherein the beam waist location lies at the output of the excitation source (e.g., a laser aperture of a free space laser)], $d_0^{(1)}$ is a distance along the optical path from the output of the excitation source to the galvanometer optical scanner, and $d_2$ is a maximal distance along a maximal length optical path from the galvanometer optical scanner to a location within the scan region (e.g., measured from the galvanometer optical scanner to a location at a corner of the scan region).

In certain embodiments, $d_0^{(1)}$ is at least 50 mm (e.g., at least 100 mm). In certain embodiments, $d_0^{(1)}$ is less than or equal to 250 mm (e.g., less than or equal to 200 mm). In certain embodiments, $d_0^{(1)}$ is from 50 mm to 200 mm (e.g., from 50 to 180 mm). In certain embodiments, $d_2$ is at least 100 mm (e.g., at least 150 mm). In certain embodiments, $d_2$ is less than or equal to 500 mm (e.g., less than or equal to 250 mm). In certain embodiments, $d_2$ is from 50 to 500 mm (e.g., from 100 to 250 mm; e.g. from 150 to 250 mm). In certain embodiments, $w_{max}$ is less than or equal to 2 mm (e.g., less than or equal to 1.5 mm; e.g., less than or equal to 1 mm). In certain embodiments, $w_{max}$ is approximately 1 mm. In certain embodiments, $w_{max}$ is approximately 0.5 mm.

In certain embodiments, a half-angle divergence of the collimated beam of excitation light emitted from the output of the excitation source is less than or equal to 5 mrad (e.g., less than or equal to 2 mrad; e.g., less than or equal to 1.5 mrad; e.g., less than or equal to 1.25 mrad).

In certain embodiments, the system comprises a beam shaping optic positioned in the optical path from the output of the excitation source to the galvanometer optical scanner, wherein the beam shaping optic is at least one of: (A) a focusing optic, wherein the focusing optic is aligned such that after passing through the focusing optic, the beam of excitation light converges as it travels (i) towards the galvanometer optical scanner and (ii) from the galvanometer optical scanner to the object plane [e.g., such that a spot size (e.g., diameter) of the beam of excitation light at the object plane is smaller than an initial size (e.g., diameter) of the beam of excitation light at the focusing optic]; and (B) a collimating optic, wherein the collimating optic is aligned such that after passing through the collimating optic, the beam of excitation light diverges (e.g., diverges slowly) as it travels (i) towards the galvanometer optical scanner and (ii) from the galvanometer optical scanner to the object plane.

In certain embodiments, the beam shaping optic is the focusing optic.

In certain embodiments, the focusing optic is positioned [e.g., with respect to (i) the galvanometer optical scanner and (ii) the output of the excitation source (e.g., a distal end of a fiber of a fiber coupled excitation source or a fiber laser from which the beam excitation light is emitted; e.g., a laser aperture of a free space laser from which the beam of excitation light is emitted)] such that a spot size of the beam of excitation light is less than or approximately equal to 1 mm in diameter at all locations within the scan region.

In certain embodiments, a half-angle divergence, φ, of the beam of excitation light after passing through the focusing optic is such that $$\tan(\varphi) < \frac{w_{max} - w_{bw}}{d_2 - d_1},$$

wherein: $w_{max}$ is an upper bound for a desired spot size of the beam of excitation light (e.g., approximately 1 mm, e.g., a scattering length of the excitation light within a diffuse media (e.g., tissue) of a subject to be imaged), $w_{bw}$ is a spot size of the beam of excitation light at a beam waist, $d_1$ is a minimal distance along a minimal length optical path from the galvanometer optical scanner to a location within the scan region (e.g., measured from the galvanometer optical scanner to a central location of the scan region), and $d_2$ is a maximal distance along a maximal length optical path from the galvanometer optical scanner to a location within the scan region (e.g., measured from the galvanometer optical scanner to a location at a corner of the scan region; e.g., wherein $d_2$ is greater than $d_1$).

In certain embodiments, $d_1$ is at least 100 mm (e.g., at least 150 mm; e.g., at least 200 mm). In certain embodiments, $d_1$ is less than 300 mm (e.g., less than 250 mm). In certain embodiments, $d_1$ is from 100 mm to 500 mm (e.g., from 150 to 250 mm; e.g. from 200 to 250 mm; e.g. from 220 to 250 mm). In certain embodiments, $d_2$ is at least 100 mm (e.g., at least 150 mm; e.g., at least 200 mm) and greater than $d_1$. In certain embodiments, $d_2$ is less than 500 mm (e.g., less than 250 mm) and greater than $d_1$. In certain embodiments, $d_2$ is from 50 to 500 mm (e.g., from 100 to 250 mm; e.g. from 150 to 250 mm; e.g., from 220 to 250 mm) and greater than $d_1$. In certain embodiments, $w_{max}$ is less than or equal to 2 mm (e.g., less than or equal to 1.5 mm; e.g., less than or equal to 1 mm). In certain embodiments, $w_{max}$ is approximately 1 mm. In certain embodiments, $w_{max}$ is approximately 0.5 mm.

In certain embodiments, a half-angle divergence of the beam of excitation light after passing through the focusing optic is less than or equal to 25 mrad (e.g., less than or equal to 20 mrad; e.g., less than or equal to 15 mrad).

In certain embodiments, the beam shaping optic is the collimating optic.

In certain embodiments, the collimating optic is positioned [e.g., with respect to (i) the galvanometer optical scanner and (ii) the output of the excitation source (e.g., a distal end of a fiber of a fiber coupled excitation source or a fiber laser from which the beam of excitation light is emitted; e.g., a laser aperture of a free space laser from which the beam of excitation light is emitted] such that a spot size of the beam of excitation light is less than or approximately equal to 1 mm in diameter at all locations at the object plane within the scan region.

In certain embodiments, a half-angle divergence, of the beam of excitation light after passing through the collimating optic is such that $$\tan(\varphi) < \frac{w_{max} - w_{bw}}{2(d_0^{(2)} + d_2)},$$

wherein: $w_{max}$ is an upper bound for a desired spot size of the beam of excitation light within the scan region [e.g., approximately 1 mm, e.g., a scattering length of the excitation light within a diffuse media (e.g., tissue) of a subject to be imaged], $w_{bw}$ is a spot size of the beam of excitation light at a beam waist location [e.g., wherein the beam waist location lies at the output of the excitation source (e.g., a distal end of a fiber of a fiber coupled excitation source or a fiber laser from which excitation light is emitted; e.g., a laser aperture of a free space laser from which the beam of excitation light is emitted)], $d_0^{(2)}$ is a distance from the collimating optic to the galvanometer optical scanner measured along the optical path from the output of the excitation source to the galvanometer optical scanner, and $d_2$ is a maximal distance along a maximal length optical path from the galvanometer optical scanner to the scan region (e.g., measured from the galvanometer optical scanner to a location at a corner of the scan region).

In certain embodiments, $d_0^{(2)}$ is at least 50 mm (e.g., at least 100 mm). In certain embodiments, $d_0^{(2)}$ is less than or equal to 250 mm (e.g., less than or equal to 200 mm). In certain embodiments, $d_0^{(2)}$ is from 50 mm to 200 mm (e.g., from 50 to 180 mm). In certain embodiments, $d_2$ is at least 100 mm (e.g., at least 150 mm). In certain embodiments, $d_2$ is less than or equal to 500 mm (e.g., less than or equal to 250 mm). In certain embodiments, $d_2$ is from 50 to 500 mm (e.g., from 100 to 250 mm; e.g. from 150 to 250 mm). In certain embodiments, $w_{max}$ is less than or equal to 2 mm (e.g., less than or equal to 1.5 mm; e.g., less than or equal to 1 mm). In certain embodiments, $w_{max}$ is approximately 1 mm. In certain embodiments, $w_{max}$ is approximately 0.5 mm.

In certain embodiments, a half-angle divergence of the beam of excitation light after passing through the collimating optic is less than or equal to 5 mrad (e.g., less than or equal to 2 mrad; e.g., less than or equal to 1.5 mrad; e.g., less than or equal to 1.25 mrad).

In certain embodiments, a power of the excitation source is greater than or approximately equal to 100 mW (e.g., greater than or approximately equal to 200 mW; e.g., greater than or approximately equal to 200 mW; e.g., greater than or approximately equal to 300 mW).

In certain embodiments, the excitation source is a fiber coupled laser or a fiber laser and the output of the excitation source from which the beam of excitation light is emitted is a distal end an optical fiber of the fiber coupled laser or fiber laser.

In certain embodiments, a core diameter of the optical fiber of the fiber coupled laser or fiber laser is from 5 µm to 400 µm (e.g., wherein the optical fiber is a single mode optical fiber having a core diameter from 5 to 10 µm; e.g. wherein the optical fiber is a multi-mode optical fiber having a core diameter from 50 to 400 µm). In certain embodiments, a numerical aperture (NA) of the optical fiber is from 0.1 to 0.3 (e.g., from 0.1 to 0.25; e.g., from 0.15 to 0.25).

In certain embodiments, the excitation source is a free space laser, wherein the output of the excitation source from which the beam of excitation light is emitted is a laser aperture of the free space laser.

In certain embodiments, the one or more detectors comprises a focal plane array (FPA) detector (e.g., a CCD camera; e.g., a CMOS camera) comprising a plurality of pixels, wherein the FPA detector is aligned to image the scan region (e.g., such that a field of view of the FPA detector comprises the scan region).

In certain embodiments, the one or more detectors comprises a fiber bundle comprising a plurality of fibers, each of which is aligned to collect light emitted from a different location within the scan region and guides the collected light to a corresponding single element detector (e.g., a Si PD).

In certain embodiments, the one or more detectors are aligned and operable to detect the fluorescent light emitted from the fluorescent species in a transillumination geometry, wherein the beam of excitation light is directed towards the object plane from a first side of the object plane and the one or more detectors are aligned and operable to detect fluorescent light emitted in directions outwards from an opposite second side (e.g., opposite to the first side) of the object plane (e.g., wherein the one or more detectors are on an opposite side of the object plane from the galvanometer optical scanner).

In certain embodiments, the one or more subjects is a small animal (e.g., mice, rats, voles, rabbits, hamsters, and similarly-sized animals).

In certain embodiments, a thickness of at least one of the one or more subjects is approximately 1 cm.

In certain embodiments, the system comprises an animal holder operable to secure a plurality of small animals (e.g., wherein the animal holder comprises a plurality of mounts, each mount operable to secure a small animal during imaging).

In certain embodiments, the animal holder comprises one or more optical baffles [e.g., each of the one or more baffles corresponding to a structure protruding outwards from the animal holder in a direction substantially perpendicular to the object plane forwards (e.g., in the direction from which the beam of excitation light is incident on the object plane) and/or backwards (e.g., in the opposite direction from which the beam of excitation light is incident on the object plane), each baffle substantially opaque to light having a wavelength of the excitation light and/or the emitted fluorescent light and located in between two positions where small animals are secured by the animal holder (e.g., in order to reduce/eliminate cross talk)].

In certain embodiments, the tomographic imaging is performed in vivo.

In certain embodiments, the one or more detectors are aligned and operable to detect excitation light transmitted through or reflected from the one or more subjects [e.g., the one or more detectors are aligned and operable to detect an excitation image (e.g., a 2D image) corresponding to each of the discrete excitation locations], and the instructions cause the processor to: receive and/or access data corresponding to the detected excitation light [e.g., the data comprising an excitation signal (e.g., an excitation image (e.g., a 2D image)) detected following transmission of the excitation light through or reflection of the excitation light by the one or more subjects when the excitation light is directed towards each of a plurality of discrete excitation locations across the scan region]; and obtain (e.g., compute) one or more tomographic images of the one or more subjects using the data corresponding to the detected excitation light and the data corresponding to the detected fluorescent light (e.g., by performing tomographic reconstruction).

In certain embodiments, the galvanometer optical scanner is aligned and operable to scan the beam of excitation light across the scan region by directing the beam of excitation light to a plurality of discrete excitation locations within the scan region, wherein, for each discrete excitation location, a given subject of the one or more subjects that is positioned in the path of the beam of excitation light directed towards the discrete excitation location is illuminated by the beam of excitation light at a corresponding illumination location on a surface of the subject, such that the beam of excitation light is incident on the surface of the given subject at the corresponding illumination location and diffuses within the subject, thereby providing for excitation of a fluorescent species (e.g., of the one or more fluorescent species) within the given subject (e.g., as a result of diffusion of excitation light from the corresponding illumination location; e.g., thereby providing for excitation of a fluorescent species located within a corresponding diffusion volume beneath the surface of the subject into which excitation light incident onto the subject at the corresponding illumination location diffuses), the one or more detectors are aligned and operable to detect, for each discrete excitation location, a corresponding fluorescence emission image (e.g., a 2D image) representing detected fluorescent light emitted by the fluorescent species within a given subject that is positioned in the path of the beam of excitation light directed to the discrete excitation location, thereby providing for detection of a plurality of fluorescence emission images, each corresponding to a discrete excitation location, and the instructions cause the processor to: receive and/or access data corresponding to the detected fluorescent light, the data corresponding to the detected fluorescent light comprising the plurality of fluorescence emission images; and obtain (e.g., compute) the one or more tomographic images of the one or more subjects using the plurality of fluorescence emission images.

In certain embodiments, the one or more detectors are aligned and operable to detect, for each discrete excitation location, a corresponding excitation image representing excitation light transmitted through or reflected by the given subject when the beam of excitation light incident on the surface of the given subject at the corresponding illumination location, such that a plurality of excitation images, each corresponding to a discrete excitation location, are detected, and the instructions cause the processor to: receive and/or access data corresponding to the detected excitation light, the data corresponding to the detected excitation light comprising the plurality of excitation images; and obtain (e.g., compute) the one or more tomographic images of the one or more subjects using the plurality of fluorescence emission images and the plurality of excitation images.

In certain embodiments, the galvanometer optical scanner is operable to scan the beam of excitation light across the scan region by directing it to a plurality of discrete excitation locations within the scan region, wherein: the discrete excitation locations are arranged in sets, each set comprising a plurality of discrete excitation locations, each discrete excitation location of a given set corresponding to a different subject of the one or more subjects (e.g., wherein each set comprises a discrete excitation location corresponding each subject of the one or more subjects), the galvanometer optical scanner is operable to scan the beam of excitation light one set at a time, directing the beam of excitation light to each discrete excitation location within a given set before proceeding on to a next set (e.g., directing the beam of excitation light to each discrete excitation location within a first set before directing the beam of excitation light to each discrete excitation location within a second set), and the galvanometer optical scanner is operable to scan the beam of excitation light through all the discrete excitation locations of given set within a time corresponding to an exposure window of the one or more detectors, and the one or more detectors are aligned and operable to detect, for each set of discrete excitation locations, a corresponding fluorescence emission image representing detected fluorescent light emitted during the exposure window of the one or more detectors as a result of excitation of the one or more fluorescent species within the one or more subjects by excitation light directed to each excitation location within a given set (e.g., such that each fluorescence emission image is a multi-subject fluorescence emission image that represents detected fluorescent light emitted from within each of the one or more subjects, by a fluorescent species within each subject).

In certain embodiments, the data corresponding to the detected fluorescent light comprises, for each set of discrete excitation locations, the corresponding fluorescence emission image, and the instructions cause the processor to obtain (e.g., compute) a tomographic image for each subject of the one or more subjects using the data fluorescence emission images (e.g., each corresponding to a set of discrete excitation locations) (e.g., by performing tomographic reconstruction).

In certain embodiments, the instructions cause the processor to, for each subject of the one or more subjects: for each fluorescence emission image corresponding to a set of discrete excitation locations, determine a portion of the fluorescence emission image associated with the subject (e.g., the determined portion representing detected fluorescent light emitted from within the subject; e.g., using a co-registered bright field image to identify a spatial region of the fluorescence emission image corresponding to the subject), thereby determining a single subject fluorescence emission image associated with the subject and corresponding to the set of discrete excitation locations, thereby determining a plurality of single subject fluorescence emission images associated with the subject, wherein each single subject fluorescence image corresponds to a set of discrete excitation locations; and obtain (e.g., compute) a tomographic image (e.g., a 3D tomographic image) of the subject using the plurality of single subject fluorescence emission images associated with the subject.

In certain embodiments, the one or more detectors are aligned and operable to detect, for each set of discrete excitation locations, a corresponding excitation image representing excitation light transmitted through or reflected by the one or more subjects detected during the exposure window of the one or more detectors as a result of illumination of the one or more subjects by the beam of excitation light directed to each excitation location within a given set (e.g., such that each excitation image is a multi-subject excitation image that represents detected excitation light transmitted through or reflected by each of the one or more subjects), and the instructions cause the processor to: receive and/or access data corresponding to the detected excitation light, the data corresponding to the detected excitation light comprising, for each set of discrete excitation locations, the corresponding excitation image; and obtain (e.g., compute) a tomographic image for each subject of the one or more subjects using the fluorescence emission images and the excitation images (e.g., by performing tomographic reconstruction; e.g., using the fluorescence emission images and the excitation images, each of which corresponds to a set of discrete excitation locations).

In certain embodiments, the instructions cause the processor to, for each subject of the one or more subjects: for each fluorescence emission image corresponding to a set of discrete excitation locations, determine a portion of the fluorescence emission image associated with the subject (e.g., the determined portion representing detected fluorescent light emitted from within the subject; e.g., using a co-registered bright field image to identify a spatial region of the fluorescence emission image corresponding to the subject), thereby determining a single subject fluorescence emission image associated with the subject and corresponding to the set of discrete excitation locations, thereby determining a plurality of single subject fluorescence emission images associated with the subject, wherein each single subject fluorescence emission image corresponds to a set of discrete excitation locations; and for each excitation image corresponding to a set of discrete excitation locations, determine a portion of the excitation image associated with the subject (e.g., the determined portion representing detected excitation light transmitted through or reflected by the subject; e.g., using a co-registered bright field image to identify a spatial region of the excitation image corresponding to the subject), thereby determining a single subject excitation image associated with the subject and corresponding to the set of discrete excitation locations, thereby determining a plurality of single subject excitation images associated with the subject, wherein each single subject excitation image corresponds to a set of discrete excitation locations; and obtain (e.g., compute) a tomographic image (e.g., a 3D tomographic image) of the subject using the plurality of single subject fluorescence emission images associated with the subject and the plurality of single subject excitation images associated with the subject.

In another aspect, the invention is directed to a system for fast scanning of excitation light from a plurality of excitation sources over a wide field of view for tomographic imaging of one or more subjects positioned across an object plane, the system comprising: (a) a plurality of excitation sources, wherein: each excitation source is operable to emit a respective beam of excitation light (e.g., for excitation of fluorescent species within the one or more subjects), a first excitation source is aligned to direct its respective beam of excitation light along a first optical path from an output of the first excitation source to a galvanometer optical scanner comprising one or more rotating galvanometer mirrors, and each excitation source other than the first excitation source is aligned to direct its respective beam of excitation light along a respective optical path from its output to the galvanometer optical scanner at a corresponding offset angle with respect to the first optical path; (b) the galvanometer optical scanner, wherein the galvanometer optical scanner is aligned and operable to, for each excitation source, direct the respective beam of excitation light emitted by the excitation source to a respective plurality of locations (e.g., discrete excitation locations) within a respective scan region of the object plane via reflection by the one or more rotating galvanometer mirrors, such that as the one or more galvanometer mirrors is/are rotated, the respective beam of excitation light emitted by the excitation source is scanned across the respective scan region (e.g., directed towards a plurality of discrete excitation locations within the respective scan region) (e.g., each respective scan region associated with an excitation source of the plurality of excitation sources), thereby providing for illumination of the one or more subjects positioned across the object plane; (c) one or more detectors aligned and operable to detect fluorescence light emitted from one or more fluorescent species within the one or more subjects as a result of excitation by the excitation light from at least one of the plurality of excitation sources [e.g., as a result of excitation by the excitation light emitted from the at least one excitation source directed towards each of the plurality of discrete excitation locations within the respective scan region for the excitation source, e.g., one or more detectors aligned and operable to detect a fluorescence emission image (e.g., 2D image) corresponding to each of the discrete excitation locations]; (d) a processor; and (e) a memory having instructions stored thereon, wherein the instructions, when executed by the processor cause the processor to: receive and/or access data corresponding to the detected fluorescent light (e.g., the data comprising a fluorescence emission signal (e.g., image; e.g., 2D image) detected following excitation by excitation light directed towards each of the plurality of excitation locations across the respective scan region of the at least one excitation source); and obtain (e.g., compute) one or more tomographic images of the one or more subjects using the data corresponding to the detected fluorescent light (e.g., by performing tomographic reconstruction).

In certain embodiments, each excitation source emits excitation light having a distinct excitation wavelength within an excitation (absorption) band of a corresponding fluorescent species within the one or more subjects (e.g., wherein each distinct excitation wavelength is a wavelength in the range from 400 nm to 1300 nm).

In certain embodiments, the one or more detectors are aligned and operable to detect fluorescence light emitted from the one or more fluorescent species within the one or more subjects as a result of excitation by the excitation light from each of two or more excitation sources of the plurality of excitation sources [e.g., for each of the two or more excitation sources, the one or more detectors are aligned and operable to detect fluorescent light emitted by an associated fluorescent species (e.g., wherein the associated fluorescent species emits fluorescent light in response to excitation by the excitation light from the excitation source) of the one or more fluorescent species as a result of excitation by the excitation light emitted from the excitation source].

In certain embodiments, the data corresponding to the detected fluorescent light comprises, for each of two or more excitation sources of the plurality of excitation sources, a set of associated fluorescence emission signals (e.g., an image; e.g., a 2D image) detected following excitation by excitation light directed towards each of a plurality of excitation locations across the respective scan region of the excitation source, and the instructions cause the processor to, for each of the two or more excitation sources, obtain (e.g., compute) a respective set of one or more tomographic images of the one or more subjects using the associated fluorescence emission signals (e.g., by performing tomographic reconstruction), thereby obtaining a set of one or more tomographic images for each of the two or more excitation sources.

In certain embodiments, at least a portion of each of the respective scan regions of each of the excitation sources overlap with each other to produce a shared scan region.

In certain embodiments, the galvanometer optical scanner is positioned a specific distance, measured along a minimal length optical path from the galvanometer to a location within the shared scan region, to produce a shared scan region of a desired size, based on one or more maximal rotational angles of the one or more galvanometer mirrors.

In certain embodiments, the desired size of the shared scan region along a first dimension and/or a second dimension is at least 100 mm (e.g., at least 150 mm; e.g., at least 200 mm). In certain embodiments, the desired size of the shared scan region along a first dimension and/or a second dimension is from 100 to 200 mm (e.g., from 100 to 150 mm; e.g., approximately 140 mm).

In certain embodiments, a minimal distance along a minimal length optical path from the galvanometer optical scanner to a location within the shared scan region is from 150 to 250 mm (e.g., approximately 200 mm).

In certain embodiments, at least one excitation source of the plurality of excitation sources is a focused excitation source that is operable to emit its respective beam of excitation light from its output as a focused beam that converges as it travels (i) towards the galvanometer optical scanner and (ii) from the galvanometer optical scanner to the object plane [e.g., such that a spot size (e.g., diameter) of the beam of excitation light at the object plane is smaller than an initial spot size (e.g., diameter) of the beam of excitation light at the output of the excitation source].

In certain embodiments, the focused beam of excitation light emitted from the output of the focused excitation source has a spot size less than or approximately equal to 1 mm at all locations within the scan region.

In certain embodiments, the focused beam of excitation light emitted from the output of the focused excitation source has a half-angle divergence, $\varphi$, such that $$\tan(\varphi) < \frac{w_{max} - w_{bw}}{d_2 - d_1},$$

wherein: $w_{max}$ is an upper bound for a desired spot size of the focused beam of excitation light within the respective scan region of the focused excitation source (e.g., approximately 1 mm, e.g., a scattering length of the excitation light within a diffuse media (e.g., tissue) of a subject to be imaged), $w_{bw}$ is a spot size of the focused beam of excitation light at its beam waist location, $d_1$ is a minimal distance measured along a minimal length optical path from the galvanometer optical scanner to a location within the respective scan region of the focused excitation source (e.g., measured from the galvanometer optical scanner to a central location of the respective scan region of the focused excitation source), and $d_2$ is a maximal distance along a maximal length optical path from the galvanometer optical scanner to a location within the respective scan region of the focused source (e.g., measured from the galvanometer optical scanner to a location at a corner of the respective scan region of the focused excitation source; e.g., wherein $d_2$ is greater than $d_1$).

In certain embodiments, $d_1$ is at least 100 mm (e.g., at least 150 mm; e.g., at least 200 mm). In certain embodiments, $d_1$ is less than 300 mm (e.g., less than 250 mm). In certain embodiments, $d_1$ is from 100 mm to 500 mm (e.g., from 150 to 250 mm; e.g. from 200 to 250 mm; e.g. from 220 to 250 mm). In certain embodiments, $d_2$ is at least 100 mm (e.g., at least 150 mm; e.g., at least 200 mm) and greater than $d_1$. In certain embodiments, $d_2$ is less than 500 mm (e.g., less than 250 mm) and greater than $d_1$. In certain embodiments, $d_2$ is from 50 to 500 mm (e.g., from 100 to 250 mm; e.g. from 150 to 250 mm; e.g. from 220 to 250 mm) and greater than $d_1$. In certain embodiments, $w_{max}$ is less than or equal to 2 mm (e.g., less than or equal to 1.5 mm; e.g., less than or equal to 1 mm). In certain embodiments, $w_{max}$ is approximately 1 mm. In certain embodiments, $w_{max}$ is approximately 0.5 mm.

In certain embodiments, a half-angle divergence of the focused beam of excitation light emitted from the output of the focused excitation source is less than or equal to 25 mrad (e.g., less than or equal to 20 mrad; e.g., less than or equal to 15 mrad).

In certain embodiments, at least one excitation source of the plurality of excitation sources is a collimated excitation source that is operable to emit its respective beam of excitation light from its output as a collimated beam that diverges (e.g., diverges slowly) as it travels (i) towards the galvanometer optical scanner and (ii) from the galvanometer optical scanner to the object plane.

In certain embodiments, the collimated beam of excitation light emitted from the output of the collimated excitation source has a spot size less than or approximately equal to 1 mm in diameter at all locations within the scan region.

In certain embodiments, the collimated beam of excitation light emitted from the output of the collimated excitation source has a half-angle divergence, $\varphi$, such that $$\tan(\varphi) < \frac{w_{max} - w_{bw}}{2(d_0^{(1)} + d_2)},$$

wherein: $w_{max}$ is an upper bound for a desired spot size of the collimated beam of excitation light within the respective scan region of the collimated excitation source (e.g., approximately 1 mm, e.g., a scattering length of the excitation light within a diffuse media (e.g., tissue) of a subject to be imaged), $w_{bw}$ is a spot size of the beam of the collimated beam of excitation light its beam waist location [e.g., wherein the beam waist location lies at the output of the excitation source (e.g., a laser aperture of a free space laser)], $d_0^{(1)}$ is a distance along the optical path from the output of the collimated excitation source to the galvanometer optical scanner, and $d_2$ is a maximal distance along a maximal length optical path from the galvanometer optical scanner to a location within the respective scan region of the collimated excitation source (e.g., measured from the galvanometer optical scanner to a location at a corner of the respective scan region of the collimated source).

In certain embodiments, $d_0^{(1)}$ is at least 50 mm (e.g., at least 100 mm). In certain embodiments, $d_0^{(1)}$ is less than or equal to 250 mm (e.g., less than or equal to 200 mm). In certain embodiments, $d_0^{(1)}$ is from 50 mm to 200 mm (e.g., from 50 to 180 mm). In certain embodiments, $d_2$ is at least 100 mm (e.g., at least 150 mm). In certain embodiments, $d_2$ is less than or equal to 500 mm (e.g., less than or equal to 250 mm). In certain embodiments, $d_2$ is from 50 to 500 mm (e.g., from 100 to 250 mm; e.g. from 150 to 250 mm). In certain embodiments, $w_{max}$ is less than or equal to 2 mm (e.g., less than or equal to 1.5 mm; e.g., less than or equal to 1 mm). In certain embodiments, $w_{max}$ is approximately 1 mm. In certain embodiments, $w_{max}$ is approximately 0.5 mm.

In certain embodiments, a half-angle divergence of the collimated beam of excitation light emitted from the output of the collimated excitation source is less than or equal to 5 mrad (e.g., less than or equal to 2 mrad; e.g., less than or equal to 1.5 mrad; e.g., less than or equal to 1.25 mrad).

In certain embodiments, the system comprises, for at least one excitation source of the plurality of excitation sources, a beam shaping optic associated with the excitation source and positioned in the respective optical path from the output of the associated excitation source to the galvanometer optical scanner, and wherein the beam shaping optic is at least one of: (A) a focusing optic, wherein the focusing optic is aligned such that after passing through the focusing optic, an associated beam of excitation light emitted from the output of the associated excitation source converges as it travels (i) towards the galvanometer optical scanner and (ii) from the galvanometer optical scanner to the object plane [e.g., such that a spot size (e.g., diameter) of the associated beam of excitation light at the object plane is smaller than an initial size (e.g., diameter) of the associated beam of excitation light at the focusing optic]; and (B) a collimating optic, wherein the collimating optic is aligned such that after passing through the collimating optic, an associated beam of excitation light emitted from the output of associated excitation source diverges (e.g., diverges slowly) as it travels (i) towards the galvanometer optical scanner and (ii) from the galvanometer optical scanner to the object plane.

In certain embodiments, the beam shaping optic is a focusing optic.

In certain embodiments, the focusing optic is positioned [e.g., with respect to (i) the galvanometer optical scanner and (ii) the output of the associated excitation source (e.g., a distal end of a fiber of a fiber coupled excitation source or a fiber laser from which the associated beam excitation light is emitted; e.g., a laser aperture of a free space laser from which the associated beam of excitation light is emitted)] such that a spot size of the associated beam of excitation light is less than or approximately equal to 1 mm in diameter at all locations within the respective scan region of the associated excitation source.

In certain embodiments, a half-angle divergence, $\varphi$, of the associated beam of excitation light after passing through the focusing optic is such that $$\tan(\varphi) < \frac{w_{max} - w_{bw}}{d_2 - d_1},$$

wherein: $w_{max}$ is an upper bound for a desired spot size of the associated beam of excitation light (e.g., approximately 1 mm, e.g., a scattering length of the excitation light within a diffuse media (e.g., tissue) of a subject to be imaged), $w_{bw}$ is a spot size of the associated beam of excitation light at a beam waist location, $d_1$ is a minimal distance along an minimal length optical path from the galvanometer optical scanner to a location within the respective scan region of the associated excitation source (e.g., wherein the minimal distance, $d_1$ is measured from the galvanometer optical scanner to a central location of the respective scan region of the associated excitation source), and $d_2$ is a maximal distance along an maximal length optical path from the galvanometer optical scanner to a location within the respective scan region of the associated excitation source (e.g., wherein $d_2$ is measured from the galvanometer optical scanner to a location at a corner of the respective scan region of the associated excitation source; e.g., wherein $d_2$ is greater than $d_1$).

In certain embodiments, $d_1$ is at least 100 mm (e.g., at least 150 mm; e.g., at least 200 mm). In certain embodiments, $d_1$ is less than 300 mm (e.g., less than 250 mm). In certain embodiments, $d_1$ is from 100 mm to 500 mm (e.g., from 150 to 250 mm; e.g. from 200 to 250 mm; e.g. from 220 to 250 mm). In certain embodiments, $d_2$ is at least 100 mm (e.g., at least 150 mm; e.g., at least 200 mm) and greater than $d_1$. In certain embodiments, $d_2$ is less than 500 mm (e.g., less than 250 mm) and greater than $d_1$. In certain embodiments, $d_2$ is from 50 to 500 mm (e.g., from 100 to 250 mm; e.g. from 150 to 250 mm; e.g., from 220 to 250 mm) and greater than $d_1$. In certain embodiments, $w_{max}$ is less than or equal to 2 mm (e.g., less than or equal to 1.5 mm; e.g., less than or equal to 1 mm). In certain embodiments, $w_{max}$ is approximately 1 mm. In certain embodiments, $w_{max}$ is approximately 0.5 mm.

In certain embodiments, a half-angle divergence of the associated beam of excitation light after passing through the focusing optic is less than or equal to 25 mrad (e.g., less than or equal to 20 mrad; e.g., less than or equal to 15 mrad).

In certain embodiments, the beam shaping optic is the collimating optic.

In certain embodiments, the collimating optic is positioned [e.g., with respect to (i) the galvanometer optical scanner and (ii) the output of the associated excitation source (e.g., a distal end of a fiber of a fiber coupled excitation source or a fiber laser from which the beam of excitation light is emitted; e.g., a laser aperture of a free space laser from which the beam of excitation light is emitted] such that a spot size of the associated beam of excitation light is less than or approximately equal to 1 mm in diameter at all locations at the object plane within the respective scan region of the associated excitation source.

In certain embodiments, a half-angle divergence, $\varphi$, of the associated beam of excitation light after passing through the collimating optic is such that $$\tan(\varphi) < \frac{w_{max} - w_{bw}}{2(d_0^{(2)} + d_2)},$$

wherein: $w_{max}$ is an upper bound for a desired spot size of the associated beam of excitation light within the respective scan region of the associated excitation source [e.g., approximately 1 mm, e.g., a scattering length of the excitation light within a diffuse media (e.g., tissue) of a subject to be imaged], $w_{bw}$ is a spot size of the associated beam of excitation light at a beam waist location [e.g., wherein the beam waist location lies at the output of the associated excitation source (e.g., a distal end of a fiber of a fiber coupled excitation source or a fiber laser from which excitation light is emitted; e.g., a laser aperture of a free space laser from which the respective beam of excitation light is emitted)], $d_0^{(2)}$ is a distance from the collimating optic to the galvanometer optical scanner measured along the optical path from the output of the associated excitation source to the galvanometer optical scanner, and $d_2$ is a maximal distance along a maximal length optical path from the galvanometer optical scanner to the respective scan region of the associated excitation source (e.g., wherein $d_2$ is measured from the galvanometer optical scanner to a location at a corner of the respective scan region of the associated excitation source).

In certain embodiments, $d_0^{(2)}$ is at least 50 mm (e.g., at least 100 mm). In certain embodiments, $d_0^{(2)}$ is less than or equal to 250 mm (e.g., less than or equal to 200 mm). In certain embodiments, $d_0^{(2)}$ is from 50 mm to 200 mm (e.g., from 50 to 180 mm). In certain embodiments, $d_2$ is at least 100 mm (e.g., at least 150 mm). In certain embodiments, $d_2$ is less than or equal to 500 mm (e.g., less than or equal to 250 mm). In certain embodiments, $d_2$ is from 50 to 500 mm (e.g., from 100 to 250 mm; e.g. from 150 to 250 mm). In certain embodiments, $w_{max}$ is less than or equal to 2 mm (e.g., less than or equal to 1.5 mm; e.g., less than or equal to 1 mm). In certain embodiments, $w_{max}$ is approximately 1 mm. In certain embodiments, $w_{max}$ is approximately 0.5 mm.

In certain embodiments, a half-angle divergence of the associated beam of excitation light after passing through the collimating optic is less than or equal to 5 mrad (e.g., less than or equal to 2 mrad; e.g., less than or equal to 1.5 mrad; e.g., less than or equal to 1.25 mrad).

In certain embodiments, a power of at least one excitation source of the plurality of excitation sources is greater than or approximately equal to 100 mW (e.g., greater than or approximately equal to 200 mW; e.g., greater than or approximately equal to 200 mW; e.g., greater than or approximately equal to 300 mW).

In certain embodiments, at least one excitation source of the plurality of excitation sources is a fiber coupled laser or a fiber laser and the output of the at least one excitation source from which the beam of excitation light is emitted is a distal end an optical fiber of the fiber coupled laser or fiber laser.

In certain embodiments, a core diameter of the optical fiber of the fiber coupled laser or fiber laser is from 5 μm to 400 μm (e.g., wherein the optical fiber is a single mode optical fiber having a core diameter from 5 to 10 μm; e.g. wherein the optical fiber is a multi-mode optical fiber having a core diameter from 50 to 400 μm). In certain embodiments, a numerical aperture (NA) of the optical fiber is from 0.1 to 0.3 (e.g., from 0.1 to 0.25; e.g., from 0.15 to 0.25).

In certain embodiments, at least one excitation source of the plurality of excitation sources is a free space laser, wherein the output of the at least one excitation source from which the beam of excitation light is emitted is a laser aperture of the free space laser.

In certain embodiments, the one or more detectors comprises a focal plane array (FPA) detector (e.g., a CCD camera; e.g., a CMOS camera) comprising a plurality of pixels, wherein the FPA detector is aligned to image at least a portion of each respective scan region of each of the excitation sources (e.g., such that a field of view of the FPA detector comprises at least a portion of each respective scan region).

In certain embodiments, the one or more detectors comprises a fiber bundle comprising a plurality of fibers, each of which is aligned to collect light emitted from a different location within the scan region and guides the collected light to a corresponding single element detector (e.g., a Si PD).

In certain embodiments, the one or more detectors are aligned and operable to detect the fluorescent light emitted from the fluorescent species in a transillumination geometry, wherein each respective beam of excitation light is directed towards the object plane from a first side of the object plane and the one or more detectors are aligned and operable (e.g., aligned) to detect fluorescent light emitted in directions outwards from an opposite second side (e.g., opposite to the first side) of the object plane (e.g., wherein the one or more detectors are on an opposite side of the object plane from the galvanometer optical scanner).

In certain embodiments, the one or more subjects is a small animal (e.g., mice, rats, voles, rabbits, hamsters, and similarly-sized animals).

In certain embodiments, a thickness of at least one of the one or more subjects is approximately 1 cm.

In certain embodiments, the system comprises an animal holder operable to secure a plurality of small animals (e.g., wherein the animal holder comprises a plurality of mounts, each mount operable to secure a small animal during imaging).

In certain embodiments, the animal holder comprises one or more optical baffles [e.g., each of the one or more baffles corresponding to a structure protruding outwards from the animal holder in a direction substantially perpendicular to the object plane forwards (e.g., in the direction from which the beam of excitation light is incident on the object plane) and/or backwards (e.g., in the opposite direction from which the beam of excitation light is incident on the object plane), each baffle substantially opaque to light having a wavelength of the excitation light and/or the emitted fluorescent light and located in between two positions where small animals are secured by the animal holder (e.g., in order to reduce/eliminate cross talk)].

In certain embodiments, the tomographic imaging is performed in vivo.

In certain embodiments, the one or more detectors are aligned and operable to detect, for at least one excitation source of the plurality of excitation sources, excitation light emitted by the at least one excitation source that is transmitted through or reflected from the one or more subjects [e.g., the one or more detectors are aligned and operable to detect an excitation image (e.g., a 2D image) corresponding to each of the discrete excitation locations within the respective scan region of the at least one excitation source], and the instructions cause the processor to: receive and/or access data corresponding to the detected excitation light [e.g., the data comprising an excitation signal (e.g., an excitation image (e.g., a 2D image)) detected following transmission of the excitation light through or reflection of the excitation light by the one or more subjects when the excitation light is directed towards each of a plurality of discrete excitation locations across the respective scan region of the at least one excitation source]; and obtain (e.g., compute) one or more tomographic images of the one or more subjects using the data corresponding to the detected excitation light and the data corresponding to the detected fluorescent light (e.g., by performing tomographic reconstruction).

In certain embodiments, for at least one excitation source of the plurality of excitation sources: the galvanometer optical scanner is aligned and operable to scan the respective beam of excitation light emitted by the excitation source across the respective scan region of the excitation source by directing the respective beam of excitation light to a plurality of discrete excitation locations within the respective scan region, wherein, for each discrete excitation location, a given subject of the one or more subjects that is positioned in the path of the respective beam of excitation light directed towards the discrete excitation location is illuminated by the respective beam of excitation light at a corresponding illumination location on a surface of the subject, such that the respective beam of excitation light is incident on the surface of the given subject at the corresponding illumination location and diffuses within the subject, thereby providing for excitation of a fluorescent species (e.g., of the one or more fluorescent species) within the given subject (e.g., as a result of diffusion of excitation light from the corresponding illumination location; e.g., thereby providing for excitation of a fluorescent species located within a corresponding diffusion volume beneath the surface of the subject into which excitation light incident onto the subject at the corresponding illumination location diffuses), the one or more detectors are aligned and operable to detect, for each discrete excitation location, a corresponding fluorescence emission image (e.g., a 2D image) representing detected fluorescent light emitted by the fluorescent species within a given subject that is positioned in a path of the respective beam of excitation light directed to the discrete excitation location, thereby providing for detection of a plurality of fluorescence emission images, each corresponding to a discrete excitation location within the respective scan region of the excitation source, and the instructions cause the processor to: receive and/or access data corresponding to the detected fluorescent light, the data corresponding to the detected fluorescent light comprising the plurality of fluorescence emission images detected for the excitation source; and obtain (e.g., compute) the one or more tomographic images of the one or more subjects using the plurality of fluorescence emission images detected for the excitation source.

In certain embodiments, for at least one excitation source of the plurality of excitation sources: the one or more detectors are aligned and operable to detect, for each discrete excitation location within the respective scan region of the excitation source, a corresponding excitation image representing excitation light emitted by the excitation source that is transmitted through or reflected by the given subject when the respective beam of excitation light is incident on the surface of the given subject at the corresponding illumination location, thereby providing for detection of a plurality of excitation images, each corresponding to a discrete excitation location within the respective scan region of the excitation source, and the instructions cause the processor to: receive and/or access data corresponding to the detected excitation light, the data corresponding to the detected excitation light comprising the plurality of excitation images detected for the excitation source; and obtain (e.g., compute) the one or more tomographic images of the one or more subjects using the plurality of fluorescence emission images detected for the excitation source and the plurality of excitation images detected for the excitation source.

In certain embodiments, for at least one excitation source of the plurality of excitation sources (e.g., for each excitation source of the plurality of excitation sources): the galvanometer optical scanner is operable to scan the respective beam of excitation light across the respective scan region by directing it to a plurality of discrete excitation locations within the respective scan region of the excitation source, wherein: the discrete excitation locations are arranged in sets, each set comprising a plurality of discrete excitation locations, each discrete excitation location of a given set corresponding to a different subject of the one or more subjects (e.g., wherein each set comprises a discrete excitation location corresponding each subject of the one or more subjects), the galvanometer optical scanner is operable to scan the respective beam of excitation light one set at a time, directing the respective beam of excitation light to each discrete excitation location within a given set before proceeding on to a next set (e.g., directing the respective beam of excitation light to each discrete excitation location within a first set before directing the respective beam of excitation light to each discrete excitation location within a second set), and the galvanometer optical scanner is operable to scan the respective beam of excitation light through all the discrete excitation locations of given set within a time corresponding to an exposure window of the one or more detectors, and the one or more detectors are aligned and operable to detect, for each set of discrete excitation locations, a corresponding fluorescence emission image representing detected fluorescent light emitted during the exposure window of the one or more detectors as a result of excitation of the one or more fluorescent species within the one or more subjects by excitation light emitted by the excitation source and directed to each excitation location within a given set (e.g., such that each fluorescence emission image is a multi-subject fluorescence emission image that represents detected fluorescent light emitted from within each of the one or more subjects, by the fluorescent species within each subject).

In certain embodiments, the data corresponding to the detected fluorescent light comprises, for each set of discrete excitation locations, the corresponding fluorescence emission image, and the instructions cause the processor to obtain (e.g., compute) a tomographic image for each subject of the one or more subjects using the fluorescence emission images (e.g., each corresponding to a set of discrete excitation locations) (e.g., by performing tomographic reconstruction).

In certain embodiments, the instructions cause the processor to, for each subject of the one or more subjects: for each fluorescence emission image corresponding to a set of discrete excitation locations, determine a portion of the fluorescence emission image associated with the subject (e.g., the determined portion representing detected fluorescent light emitted from within the subject; e.g., using a co-registered bright field image to identify a spatial region of the fluorescence emission image corresponding to the subject), thereby determining a single subject fluorescence emission image associated with the subject and corresponding to the set of discrete excitation locations, thereby determining a plurality of single subject fluorescence emission images associated with the subject, wherein each single subject fluorescence image corresponds to a set of discrete excitation locations; and obtain (e.g., compute) a tomographic image (e.g., a 3D tomographic image) of the subject using the plurality of single subject fluorescence emission images associated with the subject.

In certain embodiments, the one or more detectors are aligned and operable to detect, for each set of discrete excitation locations, a corresponding excitation image excitation light transmitted through or reflected by the one or more subjects detected during the exposure window of the one or more detectors as a result of illumination of the one or more subjects by the respective beam of excitation light directed to each excitation location within a given set (e.g., such that each excitation image is a multi-subject excitation image that represents detected excitation light transmitted through or reflected by each of the one or more subjects), and the instructions cause the processor to: receive and/or access data corresponding to the detected excitation light, the data corresponding to the detected excitation light comprising, for each set of discrete excitation locations, the corresponding excitation image; and obtain (e.g., compute) a tomographic image for each subject of the one or more subjects using fluorescence emission images and the excitation images (e.g., by performing tomographic reconstruction; e.g., using the fluorescence emission images and the excitation images, each of which corresponds to a set of discrete excitation locations).

In certain embodiments, the instructions cause the processor to, for each subject of the one or more subjects: for each fluorescence emission image corresponding to a set of discrete excitation locations, determine a portion of the fluorescence emission image associated with the subject (e.g., the determined portion representing detected fluorescent light emitted from within the subject; e.g., using a co-registered bright field image to identify a spatial region of the fluorescence emission image corresponding to the subject), thereby determining a single subject fluorescence emission image associated with the subject and corresponding to the set of discrete excitation locations, thereby determining a plurality of single subject fluorescence emission images associated with the subject, wherein each single subject fluorescence emission image corresponds to a set of discrete excitation locations; and for each excitation image corresponding to a set of discrete excitation locations, determine a portion of the excitation image associated with the subject (e.g., the determined portion representing detected excitation light transmitted through or reflected by the subject; e.g., using a co-registered bright field image to identify a spatial region of the excitation image corresponding to the subject), thereby determining a single subject excitation image associated with the subject and corresponding to the set of discrete excitation locations, thereby determining a plurality of single subject excitation images associated with the subject, wherein each single subject excitation image corresponds to a set of discrete excitation locations; and obtain (e.g., compute) a tomographic image (e.g., a 3D tomographic image) of the subject using the plurality of single subject fluorescence emission images associated with the subject and the plurality of single subject excitation images associated with the subject.

In another aspect, the invention is directed to a method for fast scanning of excitation light over a wide field of view for tomographic imaging of one or more subjects positioned across an object plane, the method comprising: (a) illuminating the one or more subjects with a beam of excitation light from an excitation source, wherein the excitation source is aligned to direct the beam of excitation light along an optical path from an output of the excitation source to a galvanometer optical scanner comprising one or more rotating galvanometer mirrors, wherein the galvanometer optical scanner is aligned and operable to direct the beam of excitation light to a plurality of locations (e.g., a plurality of discrete excitation locations) within a scan region of the object plane via reflection by the one or more rotating galvanometer mirrors, such that as the one or more galvanometer mirrors is/are rotated, the beam of excitation light is scanned across the scan region (e.g., directed towards a plurality of discrete excitation locations), thereby providing for illumination of the one or more subjects positioned across the object plane, and (b) detecting, with one or more detectors, fluorescent light emitted from a fluorescent species within the one or more subjects as a result of excitation by the excitation light [e.g., as a result of excitation by the excitation light directed towards each of the plurality of discrete excitation locations, e.g., one or more detectors configured to detect a fluorescence emission image (e.g., 2D image) corresponding to each of the discrete excitation locations]; (c) receiving and/or accessing, by a processor of a computing device, data corresponding to the detected fluorescent light (e.g., the data comprising a fluorescence emission signal (e.g., image, e.g., 2D image) detected following excitation by excitation light directed towards each of a plurality of excitation locations within the scan region); and (d) obtaining (e.g., computing), by the processor, one or more tomographic images of the one or more subjects using the data corresponding to the detected fluorescent light (e.g., by performing tomographic reconstruction).

In certain embodiments, the galvanometer optical scanner is positioned a specific distance, measured along a minimal length optical path from the galvanometer optical scanner to a location within the scan region (e.g., a central location of the scan region), to produce a scan region of a desired size, based on one or more maximal rotational angles of the one or more galvanometer mirrors.

In certain embodiments, the desired size of the scan region along a first dimension and/or a second dimension is at least 100 mm (e.g., at least 150 mm; e.g., at least 200 mm).

In certain embodiments, the desired size of the scan region along a first dimension and/or a second dimension is from 100 to 200 mm (e.g., from 100 to 150 mm; e.g., approximately 140 mm).

In certain embodiments, a minimal distance along a minimal length optical path from the galvanometer optical scanner to a location within the scan region is from 150 to 250 mm (e.g., approximately 200 mm).

In certain embodiments, the excitation source is operable to emit the beam of excitation light from its output as a focused beam that converges as it travels (i) towards the galvanometer optical scanner and (ii) from the galvanometer optical scanner to the object plane [e.g., such that a spot size (e.g., diameter) of the beam of excitation light at the object plane is smaller than an initial spot size (e.g., diameter) of the beam of excitation light at the output of the excitation source].

In certain embodiments, the focused beam of excitation light emitted from the output of the excitation source has a spot size less than or approximately equal to 1 mm at all locations within the scan region.

In certain embodiments, the focused beam of excitation light emitted from the output of the excitation source has a half-angle divergence, φ, such that $$\tan(\varphi) < \frac{w_{max} - w_{bw}}{d_2 - d_1},$$

wherein: $w_{max}$ is an upper bound for a desired spot size of the beam of excitation light within the scan region (e.g., approximately 1 mm, e.g., a scattering length of the excitation light within a diffuse media (e.g., tissue) of a subject to be imaged), $w_{bw}$ is a spot size of the beam of excitation light at its beam waist location, $d_1$ is a minimal distance measured along a minimal length optical path from the galvanometer optical scanner to a location within the scan region (e.g., measured from the galvanometer optical scanner to a central location of the scan region), and $d_2$ is a maximal distance along a maximal length optical path from the galvanometer optical scanner to a location within the scan region (e.g., measured from the galvanometer optical scanner to a location at a corner of the scan region; e.g., wherein $d_2$ is greater than $d_1$).

In certain embodiments, $d_1$ is at least 100 mm (e.g., at least 150 mm; e.g., at least 200 mm). In certain embodiments, $d_1$ is less than 300 mm (e.g., less than 250 mm). In certain embodiments, $d_1$ is from 100 mm to 500 mm (e.g., from 150 to 250 mm; e.g. from 200 to 250 mm; e.g. from 220 to 250 mm). In certain embodiments, $d_2$ is at least 100 mm (e.g., at least 150 mm; e.g., at least 200 mm) and greater than $d_1$. In certain embodiments, $d_2$ is less than 500 mm (e.g., less than 250 mm) and greater than $d_1$. In certain embodiments, $d_2$ is from 50 to 500 mm (e.g., from 100 to 250 mm; e.g. from 150 to 250 mm; e.g. from 220 to 250 mm) and greater than $d_1$. In certain embodiments, $w_{max}$ is less than or equal to 2 mm (e.g., less than or equal to 1.5 mm; e.g., less than or equal to 1 mm). In certain embodiments, $w_{max}$ is approximately 1 mm. In certain embodiments, $w_{max}$ is approximately 0.5 mm.

In certain embodiments, a half-angle divergence of the focused beam of excitation light emitted from the output of the excitation source is less than or equal to 25 mrad (e.g., less than or equal to 20 mrad; e.g., less than or equal to 15 mrad).

In certain embodiments, the excitation source is operable to emit the beam of excitation light from its output as a collimated beam that diverges (e.g., diverges slowly) as it travels (i) towards the galvanometer optical scanner and (ii) from the galvanometer optical scanner to the object plane.

In certain embodiments, the collimated beam of excitation light emitted from the output of the excitation source has a spot size less than or approximately equal to 1 mm in diameter at all locations within the scan region.

In certain embodiments, the collimated beam of excitation light emitted from the output of the excitation source has a half-angle divergence, φ, such that $$\tan(\varphi) < \frac{w_{max} - w_{bw}}{2(d_0^{(1)} + d_2)},$$

wherein: $w_{max}$ is an upper bound for a desired spot size of the collimated beam of excitation light within the scan region (e.g., approximately 1 mm, e.g., a scattering length of the excitation light within a diffuse media (e.g., tissue) of a subject to be imaged), $w_{bw}$ is a spot size of the beam of the collimated beam of excitation light its beam waist location [e.g., wherein the beam waist location lies at the output of the excitation source (e.g., a laser aperture of a free space laser)], $d_0^{(1)}$ is a distance along the optical path from the output of the excitation source to the galvanometer optical scanner, and $d_2$ is a maximal distance along a maximal length optical path from the galvanometer optical scanner to a location within the scan region (e.g., measured from the galvanometer optical scanner to a location at a corner of the scan region).

In certain embodiments, $d_0^{(1)}$ is at least 50 mm (e.g., at least 100 mm). In certain embodiments, $d_0^{(1)}$ is less than or equal to 250 mm (e.g., less than or equal to 200 mm). In certain embodiments, $d_0^{(1)}$ is from 50 mm to 200 mm (e.g., from 50 to 180 mm). In certain embodiments, $d_2$ is at least 100 mm (e.g., at least 150 mm). In certain embodiments, $d_2$ is less than or equal to 500 mm (e.g., less than or equal to 250 mm). In certain embodiments, $d_2$ is from 50 to 500 mm (e.g., from 100 to 250 mm; e.g. from 150 to 250 mm). In certain embodiments, $w_{max}$ is less than or equal to 2 mm (e.g., less than or equal to 1.5 mm; e.g., less than or equal to 1 mm). In certain embodiments, $w_{max}$ is approximately 1 mm. In certain embodiments, $w_{max}$ is approximately 0.5 mm.

In certain embodiments, a half-angle divergence of the collimated beam of excitation light emitted from the output of the excitation source is less than or equal to 5 mrad (e.g., less than or equal to 2 mrad; e.g., less than or equal to 1.5 mrad; e.g., less than or equal to 1.25 mrad).

In certain embodiments, a beam shaping optic is positioned in the optical path from the output of the excitation source to the galvanometer optical scanner, wherein the beam shaping optic is at least one of: (A) a focusing optic, wherein the focusing optic is aligned such that after passing through the focusing optic, the beam of excitation light converges as it travels (i) towards the galvanometer optical scanner and (ii) from the galvanometer optical scanner to the object plane [e.g., such that a spot size (e.g., diameter) of the beam of excitation light at the object plane is smaller than an initial size (e.g., diameter) of the beam of excitation light at the focusing optic]; and (B) a collimating optic, wherein the collimating optic is aligned such that after passing through the collimating optic, the beam of excitation light diverges (e.g., diverges slowly) as it travels (i) towards the galvanometer optical scanner and (ii) from the galvanometer optical scanner to the object plane.

In certain embodiments, the beam shaping optic is the focusing optic.

In certain embodiments, the focusing optic is positioned [e.g., with respect to (i) the galvanometer optical scanner and (ii) the output of the excitation source (e.g., a distal end of a fiber of a fiber coupled excitation source or a fiber laser from which the beam excitation light is emitted; e.g., a laser aperture of a free space laser from which the beam of excitation light is emitted)] such that a spot size of the beam of excitation light is less than or approximately equal to 1 mm in diameter at all locations within the scan region.

In certain embodiments, a half-angle divergence, φ, of the beam of excitation light after passing through the focusing optic is such that $$\tan(\varphi) < \frac{w_{max} - w_{bw}}{d_2 - d_1},$$

wherein: $w_{max}$ is an upper bound for a desired spot size of the beam of excitation light (e.g., approximately 1 mm, e.g., a scattering length of the excitation light within a diffuse media (e.g., tissue) of a subject to be imaged), $w_{bw}$ is a spot size of the beam of excitation light at a beam waist, $d_1$ is a minimal distance along a minimal length optical path from the galvanometer optical scanner to a location within the scan region (e.g., measured from the galvanometer optical scanner to a central location of the scan region), and $d_2$ is a maximal distance along a maximal length optical path from the galvanometer optical scanner to a location within the scan region (e.g., measured from the galvanometer optical scanner to a location at a corner of the scan region; e.g., wherein $d_2$ is greater than $d_1$).

In certain embodiments, $d_1$ is at least 100 mm (e.g., at least 150 mm; e.g., at least 200 mm). In certain embodiments, $d_1$ is less than 300 mm (e.g., less than 250 mm). In certain embodiments, $d_1$ is from 100 mm to 500 mm (e.g., from 150 to 250 mm; e.g. from 200 to 250 mm; e.g. from 220 to 250 mm). In certain embodiments, $d_2$ is at least 100 mm (e.g., at least 150 mm; e.g., at least 200 mm) and greater than $d_1$. In certain embodiments, $d_2$ is less than 500 mm (e.g., less than 250 mm) and greater than $d_1$. In certain embodiments, $d_2$ is from 50 to 500 mm (e.g., from 100 to 250 mm; e.g. from 150 to 250 mm; e.g., from 220 to 250 mm) and greater than $d_1$. In certain embodiments, $w_{max}$ is less than or equal to 2 mm (e.g., less than or equal to 1.5 mm; e.g., less than or equal to 1 mm). In certain embodiments, $w_{max}$ is approximately 1 mm. In certain embodiments, $w_{max}$ is approximately 0.5 mm.

In certain embodiments, a half-angle divergence of the beam of excitation light after passing through the focusing optic is less than or equal to 25 mrad (e.g., less than or equal to 20 mrad; e.g., less than or equal to 15 mrad).

In certain embodiments, the beam shaping optic is the collimating optic.

In certain embodiments, the collimating optic is positioned [e.g., with respect to (i) the galvanometer optical scanner and (ii) the output of the excitation source (e.g., a distal end of a fiber of a fiber coupled excitation source or a fiber laser from which the beam of excitation light is emitted; e.g., a laser aperture of a free space laser from which the beam of excitation light is emitted] such that a spot size of the beam of excitation light is less than or approximately equal to 1 mm in diameter at all locations at the object plane within the scan region.

In certain embodiments, a half-angle divergence, $\varphi$, of the beam of excitation light after passing through the collimating optic is such that $$\tan(\varphi) < \frac{w_{max} - w_{bw}}{2(d_0^{(2)} + d_2)},$$

wherein: $w_{max}$ is an upper bound for a desired spot size of the beam of excitation light within the scan region [e.g., approximately 1 mm, e.g., a scattering length of the excitation light within a diffuse media (e.g., tissue) of a subject to be imaged], $w_{bw}$ is a spot size of the beam of excitation light at a beam waist location [e.g., wherein the beam waist location lies at the output of the excitation source (e.g., a distal end of a fiber of a fiber coupled excitation source or a fiber laser from which excitation light is emitted; e.g., a laser aperture of a free space laser from which the beam of excitation light is emitted)], $d_0^{(2)}$ is a distance from the collimating optic to the galvanometer optical scanner measured along the optical path from the output of the excitation source to the galvanometer optical scanner, and $d_2$ is a maximal distance along a maximal length optical path from the galvanometer optical scanner to the scan region (e.g., measured from the galvanometer optical scanner to a location at a corner of the scan region).

In certain embodiments, $d_0^{(2)}$ is at least 50 mm (e.g., at least 100 mm). In certain embodiments, $d_0^{(2)}$ is less than or equal to 250 mm (e.g., less than or equal to 200 mm). In certain embodiments, $d_0^{(2)}$ is from 50 mm to 200 mm (e.g., from 50 to 180 mm). In certain embodiments, $d_2$ is at least 100 mm (e.g., at least 150 mm). In certain embodiments, $d_2$ is less than or equal to 500 mm (e.g., less than or equal to 250 mm). In certain embodiments, $d_2$ is from 50 to 500 mm (e.g., from 100 to 250 mm; e.g. from 150 to 250 mm). In certain embodiments, $w_{max}$ is less than or equal to 2 mm (e.g., less than or equal to 1.5 mm; e.g., less than or equal to 1 mm). In certain embodiments, $w_{max}$ is approximately 1 mm. In certain embodiments, $w_{max}$ is approximately 0.5 mm.

In certain embodiments, a half-angle divergence of the beam of excitation light after passing through the collimating optic is less than or equal to 5 mrad (e.g., less than or equal to 2 mrad; e.g., less than or equal to 1.5 mrad; e.g., less than or equal to 1.25 mrad).

In certain embodiments, a power of the excitation source is greater than or approximately equal to 100 mW (e.g., greater than or approximately equal to 200 mW; e.g., greater than or approximately equal to 200 mW; e.g., greater than or approximately equal to 300 mW).

In certain embodiments, the excitation source is a fiber coupled laser or a fiber laser and the output of the excitation source from which the beam of excitation light is emitted is a distal end an optical fiber of the fiber coupled laser or fiber laser.

In certain embodiments, a core diameter of the optical fiber of the fiber coupled laser or fiber laser is from 5 µm to 400 µm (e.g., wherein the optical fiber is a single mode optical fiber having a core diameter from 5 to 10 µm; e.g. wherein the optical fiber is a multi-mode optical fiber having a core diameter from 50 to 400 µm). In certain embodiments, a numerical aperture (NA) of the optical fiber is from 0.1 to 0.3 (e.g., from 0.1 to 0.25; e.g., from 0.15 to 0.25).

In certain embodiments, the excitation source is a free space laser, wherein the output of the excitation source from which the beam of excitation light is emitted is a laser aperture of the free space laser.

In certain embodiments, the one or more detectors comprises a focal plane array (FPA) detector (e.g., a CCD camera; e.g., a CMOS camera) comprising a plurality of pixels, wherein the FPA detector is aligned to image the scan region (e.g., such that a field of view of the FPA detector comprises the scan region).

In certain embodiments, the one or more detectors comprises a fiber bundle comprising a plurality of fibers, each of which is aligned to collect light emitted from a different location within the scan region and guides the collected light to a corresponding single element detector (e.g., a Si PD).

In certain embodiments, the one or more detectors are aligned and operable to detect the fluorescent light emitted from the fluorescent species in a transillumination geometry, wherein the beam of excitation light is directed towards the object plane from a first side of the object plane and the one or more detectors are aligned and operable to detect fluorescent light emitted in directions outwards from an opposite second side (e.g., opposite to the first side) of the object plane (e.g., wherein the one or more detectors are on an opposite side of the object plane from the galvanometer optical scanner).

In certain embodiments, the one or more subjects is a small animal (e.g., mice, rats, voles, rabbits, hamsters, and similarly-sized animals).

In certain embodiments, a thickness of at least one of the one or more subjects is approximately 1 cm.

In certain embodiments, the one or more subjects are positioned across the object plane using an animal holder operable to secure a plurality of small animals (e.g., wherein the animal holder comprises a plurality of mounts, each mount operable to secure a small animal during imaging).

In certain embodiments, the animal holder comprises one or more optical baffles [e.g., each of the one or more baffles corresponding to a structure protruding outwards from the animal holder in a direction substantially perpendicular to the object plane forwards (e.g., in the direction from which the beam of excitation light is incident on the object plane) and/or backwards (e.g., in the opposite direction from which the beam of excitation light is incident on the object plane), each baffle substantially opaque to light having a wavelength of the excitation light and/or the emitted fluorescent light and located in between two positions where small animals are secured by the animal holder (e.g., in order to reduce/eliminate cross talk)].

In certain embodiments, the tomographic imaging is performed in vivo.

In certain embodiments, the method comprises: detecting, with the one or more detectors, excitation light transmitted through or reflected from the one or more subjects [e.g., detecting an excitation image (e.g., a 2D image) corresponding to each of the discrete excitation locations], and receiving and/or accessing, by the processor, data corresponding to the detected excitation light [e.g., the data comprising an excitation signal (e.g., an excitation image (e.g., a 2D image)) detected following transmission of the excitation light through or reflection of the excitation light by the one or more subjects when the excitation light is directed towards each of a plurality of discrete excitation locations across the scan region]; and obtaining (e.g., computing), by the processor, the one or more tomographic images of the one or more subjects using the data corresponding to the detected excitation light and the data corresponding to the detected fluorescent light (e.g., by performing tomographic reconstruction).

In certain embodiments, step (a) comprises using the galvanometer optical scanner to direct the beam of excitation light to a plurality of discrete excitation locations within the scan region, wherein, for each discrete excitation location, a given subject of the one or more subjects that is positioned in the path of the beam of excitation light directed towards the discrete excitation location is illuminated by the beam of excitation light at a corresponding illumination location on a surface of the subject, such that the beam of excitation light is incident on the surface of the given subject at the corresponding illumination location and diffuses within the subject, thereby exciting a fluorescent species (e.g., of the one or more fluorescent species) within the given subject (e.g., as a result of diffusion of excitation light from the corresponding illumination location; e.g., thereby exciting a fluorescent species located within a corresponding diffusion volume beneath the surface of the subject into which excitation light incident onto the subject at the corresponding illumination location diffuses), step (b) comprises, for each discrete excitation location, detecting a corresponding fluorescence emission image (e.g., a 2D image) representing detected fluorescent light emitted from within a given subject positioned in the path of the beam of excitation light directed towards the discrete excitation location, as a result of excitation of the fluorescent species within the given subject, thereby detecting a plurality of fluorescence emission images, each corresponding to a discrete excitation location, step (c) comprises receiving and/or accessing data corresponding to the detected fluorescent light, the data corresponding to the detected fluorescent light comprising the plurality of fluorescence emission images, and step (d) comprises obtaining (e.g., computing) the one or more tomographic images of the one or more subjects using the plurality of fluorescence emission images.

In certain embodiments, step (b) comprises, for each discrete excitation location, detecting, with the one or more detectors, a corresponding excitation image representing excitation light transmitted through or reflected by the given subject positioned in the path of the beam of excitation light directed towards the discrete excitation location when the beam of excitation light incident on the surface of the given subject at the corresponding illumination location, thereby detecting a plurality of excitation images, each corresponding to a discrete excitation location, step (c) comprises receiving and/or accessing data corresponding to the detected excitation light, the data corresponding to the detected excitation light comprising the plurality of excitation images, and step (d) comprises obtaining (e.g., computing) the one or more tomographic images of the one or more subjects using the plurality of fluorescence emission images and the plurality of excitation images.

In certain embodiments, step (a) comprising using the galvanometer optical scanner to direct the beam of excitation light to a plurality of discrete excitation locations within the scan region, wherein: the discrete excitation locations are arranged in sets, each set comprising a plurality of discrete excitation locations, each discrete excitation location of a given set corresponding to a different subject of the one or more subjects (e.g., wherein each set comprises a discrete excitation location corresponding each subject of the one or more subjects), the galvanometer optical scanner is operable to scan the beam of excitation light one set at a time, directing the beam of excitation light to each discrete excitation location within a given set before proceeding on to a next set (e.g., directing the beam of excitation light to each discrete excitation location within a first set before directing the beam of excitation light to each discrete excitation location within a second set), and the galvanometer optical scanner is operable to scan the beam of excitation light through all the discrete excitation locations of given set within a time corresponding to an exposure window of the one or more detectors, and step (b) comprises, for each set of discrete excitation locations, detecting a fluorescence emission image, each fluorescence emission image representing detected fluorescent light emitted during the exposure window of the one or more detectors as a result of excitation of the one or more fluorescent species within the one or more subjects by excitation light directed to each excitation location within a given set (e.g., such that each fluorescence emission image is a multi-subject fluorescence emission image that represents detected fluorescent light emitted from within each of the one or more subjects, by the fluorescent species within each subject).

In certain embodiments, the data corresponding to the detected fluorescent light comprises, for each set of discrete excitation locations, the corresponding fluorescence emission image, and step (d) comprises obtaining (e.g., computing) a tomographic image for each subject of the one or more subjects using the fluorescence emission images (e.g., by performing tomographic reconstruction; e.g. using the fluorescence emission images, each corresponding to a set of discrete excitation locations).

In certain embodiments, step (d) comprises, for each subject of the one or more subjects: for each fluorescence emission image corresponding to each set of discrete excitation locations, determining a portion of the fluorescence emission image associated with the subject (e.g., the determined portion representing detected fluorescent light emitted from within the subject; e.g., using a co-registered bright field image to identify a spatial region of the fluorescence emission image corresponding to the subject), thereby determining a single subject fluorescence emission image associated with the subject and corresponding to the set of discrete excitation locations, thereby determining a plurality of single subject fluorescence emission images associated with the subject, wherein each single subject fluorescence image corresponds to a set of discrete excitation locations; and obtaining (e.g., computing) a tomographic image (e.g., a 3D tomographic image) of the subject using the plurality of single subject fluorescence emission images associated with the subject.

In certain embodiments, step (b) comprises, for each set of discrete excitation locations, detecting a corresponding excitation image, each excitation image representing detected excitation light transmitted through or reflected by the one or more subjects during the exposure window of the one or more detectors as a result of illumination of the one or more subjects by the beam of excitation light directed to each excitation location within a given set (e.g., such that each excitation image is a multi-subject excitation image that represents detected excitation light transmitted through or reflected by each of the one or more subjects), step (c) comprises receiving and/or accessing data corresponding to the detected excitation light, the data corresponding to the detected excitation light comprising, for each set of discrete excitation locations, the corresponding excitation image, and step (d) comprises obtaining (e.g., computing) a tomographic image for each subject of the one or more subjects using the fluorescence emission images and the excitation images (e.g., by performing tomographic reconstruction; e.g., using the fluorescence emission images and the excitation images, each of which corresponds to a set of discrete excitation locations).

In certain embodiments, step (d) comprises: for each fluorescence emission image corresponding to each set of discrete excitation locations, determining a portion of the fluorescence emission image associated with the subject (e.g., the determined portion representing detected fluorescent light emitted from within the subject; e.g., using a co-registered bright field image to identify a spatial region of the fluorescence emission image corresponding to the subject), thereby determining a single subject fluorescence emission image associated with the subject and corresponding to the set of discrete excitation locations, thereby determining a plurality of single subject fluorescence emission images associated with the subject, wherein each single subject fluorescence emission image corresponds to a set of discrete excitation locations; for each excitation image corresponding to each set of discrete excitation locations, determining a portion of the excitation image associated with the subject (e.g., the determined portion representing detected excitation light transmitted through or reflected by the subject; e.g., using a co-registered bright field image to identify a spatial region of the excitation image corresponding to the subject), thereby determining a single subject excitation image associated with the subject and corresponding to the set of discrete excitation locations, thereby determining a plurality of single subject excitation images associated with the subject, wherein each single subject excitation image corresponds to a set of discrete excitation locations; and obtaining (e.g., computing) a tomographic image (e.g., a 3D tomographic image) of the subject using the plurality of single subject fluorescence emission images associated with the subject and the plurality of single subject excitation images associated with the subject.

In another aspect, the invention is directed to a method for fast scanning of excitation light from a plurality of excitation sources over a wide field of view for tomographic imaging of one or more subjects positioned across an object plane, the method comprising: (a) illuminating the one or more subjects with at least one beam of excitation light emitted by a respective one of a plurality of excitation sources, wherein: (i) a first excitation source is aligned to direct its respective beam of excitation light along a first optical path from the first excitation source to a galvanometer optical scanner comprising one or more rotating galvanometer mirrors, (ii) each excitation source other than the first excitation source is aligned to direct its respective beam of excitation light along an respective optical path towards the galvanometer optical scanner at a corresponding offset angle with respect to the first optical path from the first excitation source to the galvanometer optical scanner, (iii) the galvanometer optical scanner is aligned and operable to, for each excitation source, direct the respective beam of excitation light emitted by the excitation source to a respective plurality of locations within a respective scan region of the object plane via reflection by the one or more rotating galvanometer mirrors, such that as the one or more galvanometer mirrors are rotated, the respective beam of excitation light emitted by the excitation source is scanned across the respective scan region (e.g., directed towards a plurality of discrete excitation locations within the respective scan region) (e.g., each respective scan region associated with an excitation source of the plurality of excitation sources), thereby providing for illumination of the one or more subjects positioned across the object plane [e.g., wherein a given subject positioned in proximity to (e.g., in front of; e.g., at) the scan region in the path of excitation light directed towards a given discrete excitation location behind the subject is illuminated by the excitation light, such that the excitation light directed towards the given discrete excitation location behind the subject impinges on a surface of the subject at an associated illumination location, and diffuses within the subject, thereby providing for excitation of a fluorescent species located within a volume beneath the surface of the subject associated (e.g., defined by) with diffusion of excitation light from associated illumination location]; (b) detecting, with one or more detectors, fluorescence light emitted from one or more fluorescent species within the one or more subjects as a result of excitation by the excitation light from at least one of the plurality of excitation sources [e.g., as a result of excitation by the excitation light emitted from the at least one excitation source at each of the plurality of discrete excitation locations within the respective scan region for the excitation source, e.g., one or more detectors configured to detect a fluorescence emission image (e.g., 2D image) corresponding to each of the discrete excitation locations]; (c) receiving and/or accessing, by a processor of a computing device, data corresponding to the detected fluorescent light (e.g., the data comprising a fluorescence emission signal (e.g., image; e.g., 2D image) detected following excitation at each of at least a portion of the plurality of excitation locations across the respective scan region of the at least one excitation source); and (d) obtaining (e.g., computing), by the processor, one or more tomographic images of the one or more subjects using the data corresponding to the detected fluorescent light (e.g., by performing tomographic reconstruction).

In certain embodiments, each excitation source emits excitation light having a distinct excitation wavelength within an excitation (absorption) band of a corresponding fluorescent species within the one or more subjects (e.g., wherein each distinct excitation wavelength is a wavelength in the range from 400 nm to 1300 nm).

In certain embodiments, step (b) comprises detecting fluorescence light emitted from the one or more fluorescent species within the one or more subjects as a result of excitation by the excitation light from each of two or more excitation sources of the plurality of excitation sources [e.g., detecting, for each of the two or more fluorescent light emitted by an associated fluorescent species (e.g., wherein the associated fluorescent species emits fluorescent light in response to excitation by the excitation light from the associated excitation source) of the one or more fluorescent species as a result of excitation by the excitation light emitted from the excitation source].

In certain embodiments, the data corresponding to the detected fluorescent light comprises, for each of two or more excitation sources of the plurality of excitation sources, a set of associated fluorescence emission signals (e.g., an image; e.g., a 2D image) detected following excitation by excitation light directed towards each of a plurality of excitation locations across the respective scan region of the excitation source, and step (c) comprises, for each of the two or more excitation sources, obtaining (e.g., computing) a respective set of one or more tomographic images of the one or more subjects using the associated fluorescence emission signals (e.g., by performing tomographic reconstruction), thereby obtaining a set of one or more tomographic images for each of the two or more excitation sources.

In certain embodiments, at least a portion of each of the respective scan regions of each of the excitation sources overlap with each other to produce a shared scan region.

In certain embodiments, the galvanometer optical scanner is positioned a specific distance, measured along a minimal length optical path from the galvanometer to a location within the shared scan region, to produce a shared scan region of a desired size, based on one or more maximal rotational angles of the one or more galvanometer mirrors.

In certain embodiments, the desired size of the shared scan region along a first dimension and/or a second dimension is at least 100 mm (e.g., at least 150 mm; e.g., at least 200 mm). In certain embodiments, the desired size of the shared scan region along a first dimension and/or a second dimension is from 100 to 200 mm (e.g., from 100 to 150 mm; e.g., approximately 140 mm).

In certain embodiments, a minimal distance along a minimal length optical path from the galvanometer optical scanner to a location within the shared scan region is from 150 to 250 mm (e.g., approximately 200 mm).

In certain embodiments, at least one excitation source of the plurality of excitation sources is a focused excitation source that is operable to emit its respective beam of excitation light from its output as a focused beam that converges as it travels (i) towards the galvanometer optical scanner and (ii) from the galvanometer optical scanner to the object plane [e.g., such that a spot size (e.g., diameter) of the beam of excitation light at the object plane is smaller than an initial spot size (e.g., diameter) of the beam of excitation light at the output of the excitation source].

In certain embodiments, the focused beam of excitation light emitted from the output of the focused excitation source has a spot size less than or approximately equal to 1 mm at all locations within the scan region.

In certain embodiments, the focused beam of excitation light emitted from the output of the focused excitation source has a half-angle divergence, $\varphi$, such that $$\tan(\varphi) < \frac{w_{max} - w_{bw}}{d_2 - d_1},$$

wherein: $w_{max}$ is an upper bound for a desired spot size of the focused beam of excitation light within the respective scan region of the focused excitation source (e.g., approximately 1 mm, e.g., a scattering length of the excitation light within a diffuse media (e.g., tissue) of a subject to be imaged), $w_{bw}$ is a spot size of the focused beam of excitation light at its beam waist location, $d_1$ is a minimal distance measured along a minimal length optical path from the galvanometer optical scanner to a location within the respective scan region of the focused excitation source (e.g., measured from the galvanometer optical scanner to a central location of the respective scan region of the focused excitation source), and $d_2$ is a maximal distance along a maximal length optical path from the galvanometer optical scanner to a location within the respective scan region of the focused source (e.g., measured from the galvanometer optical scanner to a location at a corner of the respective scan region of the focused excitation source; e.g., wherein $d_2$ is greater than $d_1$).

In certain embodiments, $d_1$ is at least 100 mm (e.g., at least 150 mm; e.g., at least 200 mm). In certain embodiments, $d_1$ is less than 300 mm (e.g., less than 250 mm). In certain embodiments, $d_1$ is from 100 mm to 500 mm (e.g., from 150 to 250 mm; e.g. from 200 to 250 mm; e.g. from 220 to 250 mm). In certain embodiments, $d_2$ is at least 100 mm (e.g., at least 150 mm; e.g., at least 200 mm) and greater than $d_1$. In certain embodiments, $d_2$ is less than 500 mm (e.g., less than 250 mm) and greater than $d_1$. In certain embodiments, $d_2$ is from 50 to 500 mm (e.g., from 100 to 250 mm; e.g. from 150 to 250 mm; e.g., from 220 to 250 mm) and greater than $d_1$. In certain embodiments, $w_{max}$ is less than or equal to 2 mm (e.g., less than or equal to 1.5 mm; e.g., less than or equal to 1 mm). In certain embodiments, $w_{max}$ is approximately 1 mm. In certain embodiments, $w_{max}$ is approximately 0.5 mm.

In certain embodiments, a half-angle divergence of the focused beam of excitation light emitted from the output of the focused excitation source is less than or equal to 25 mrad (e.g., less than or equal to 20 mrad; e.g., less than or equal to 15 mrad).

In certain embodiments, at least one excitation source of the plurality of excitation sources is a collimated excitation source that is operable to emit its respective beam of excitation light from its output as a collimated beam that diverges (e.g., diverges slowly) as it travels (i) towards the galvanometer optical scanner and (ii) from the galvanometer optical scanner to the object plane.

In certain embodiments, the collimated beam of excitation light emitted from the output of the collimated excitation source has a spot size less than or approximately equal to 1 mm in diameter at all locations within the scan region.

In certain embodiments, the collimated beam of excitation light emitted from the output of the collimated excitation source has a half-angle divergence, φ, such that $$\tan(\varphi) < \frac{w_{max} - w_{bw}}{2(d_0^{(1)} + d_2)},$$

wherein: $w_{max}$ is an upper bound for a desired spot size of the collimated beam of excitation light within the respective scan region of the collimated excitation source (e.g., approximately 1 mm, e.g., a scattering length of the excitation light within a diffuse media (e.g., tissue) of a subject to be imaged), $w_{bw}$ is a spot size of the beam of the collimated beam of excitation light its beam waist location [e.g., wherein the beam waist location lies at the output of the excitation source (e.g., a laser aperture of a free space laser)], $d_0^{(1)}$ is a distance along the optical path from the output of the collimated excitation source to the galvanometer optical scanner, and $d_2$ is a maximal distance along a maximal length optical path from the galvanometer optical scanner to a location within the respective scan region of the collimated excitation source (e.g., measured from the galvanometer optical scanner to a location at a corner of the respective scan region of the collimated source).

In certain embodiments, $d_0^{(1)}$ is at least 50 mm (e.g., at least 100 mm). In certain embodiments, $d_0^{(1)}$ is less than or equal to 250 mm (e.g., less than or equal to 200 mm). In certain embodiments, $d_0^{(1)}$ is from 50 mm to 200 mm (e.g., from 50 to 180 mm). In certain embodiments, $d_2$ is at least 100 mm (e.g., at least 150 mm). In certain embodiments, $d_2$ is less than or equal to 500 mm (e.g., less than or equal to 250 mm). In certain embodiments, $d_2$ is from 50 to 500 mm (e.g., from 100 to 250 mm; e.g. from 150 to 250 mm). In certain embodiments, $w_{max}$ is less than or equal to 2 mm (e.g., less than or equal to 1.5 mm; e.g., less than or equal to 1 mm). In certain embodiments, $w_{max}$ is approximately 1 mm. In certain embodiments, $w_{max}$ is approximately 0.5 mm.

In certain embodiments, a half-angle divergence of the collimated beam of excitation light emitted from the output of the collimated excitation source is less than or equal to 5 mrad (e.g., less than or equal to 2 mrad; e.g., less than or equal to 1.5 mrad; e.g., less than or equal to 1.25 mrad).

In certain embodiments, for at least one excitation source of the plurality of excitation sources, a beam shaping optic associated with the excitation source is positioned in the respective optical path from the output of the associated excitation source to the galvanometer optical scanner, and wherein the beam shaping optic is at least one of: (A) a focusing optic, wherein the focusing optic is aligned such that after passing through the focusing optic, an associated beam of excitation light emitted from the output of the associated excitation source converges as it travels (i) towards the galvanometer optical scanner and (ii) from the galvanometer optical scanner to the object plane [e.g., such that a spot size (e.g., diameter) of the associated beam of excitation light at the object plane is smaller than an initial size (e.g., diameter) of the associated beam of excitation light at the focusing optic]; and (B) a collimating optic, wherein the collimating optic is aligned such that after passing through the collimating optic, an associated beam of excitation light emitted from the output of associated excitation source diverges (e.g., diverges slowly) as it travels (i) towards the galvanometer optical scanner and (ii) from the galvanometer optical scanner to the object plane.

In certain embodiments, the beam shaping optic is a focusing optic.

In certain embodiments, the focusing optic is positioned [e.g., with respect to (i) the galvanometer optical scanner and (ii) the output of the associated excitation source (e.g., a distal end of a fiber of a fiber coupled excitation source or a fiber laser from which the associated beam excitation light is emitted; e.g., a laser aperture of a free space laser from which the associated beam of excitation light is emitted)] such that a spot size of the associated beam of excitation light is less than or approximately equal to 1 mm in diameter at all locations within the respective scan region of the associated excitation source.

In certain embodiments, a half-angle divergence, φ, of the associated beam of excitation light after passing through the focusing optic is such that $$\tan(\varphi) < \frac{w_{max} - w_{bw}}{d_2 - d_1},$$

wherein: $w_{max}$ is an upper bound for a desired spot size of the associated beam of excitation light (e.g., approximately 1 mm, e.g., a scattering length of the excitation light within a diffuse media (e.g., tissue) of a subject to be imaged), $w_{bw}$ is a spot size of the associated beam of excitation light at a beam waist location, $d_1$ is a minimal distance along a minimal length optical path from the galvanometer optical scanner to a location within the respective scan region of the associated excitation source (e.g., wherein the minimal distance, $d_1$ is measured from the galvanometer optical scanner to a central location of the respective scan region of the associated excitation source), and $d_2$ is a maximal distance along an maximal length optical path from the galvanometer optical scanner to a location within the respective scan region of the associated excitation source (e.g., wherein $d_2$ is measured from the galvanometer optical scanner to a location at a corner of the respective scan region of the associated excitation source; e.g., wherein $d_2$ is greater than $d_1$).

In certain embodiments, $d_1$ is at least 100 mm (e.g., at least 150 mm; e.g., at least 200 mm). In certain embodiments, $d_1$ is less than 300 mm (e.g., less than 250 mm). In certain embodiments, $d_1$ is from 100 mm to 500 mm (e.g., from 150 to 250 mm; e.g. from 200 to 250 mm; e.g. from 220 to 250 mm). In certain embodiments, $d_2$ is at least 100 mm (e.g., at least 150 mm; e.g., at least 200 mm) and greater than $d_1$. In certain embodiments, $d_2$ is less than 500 mm (e.g., less than 250 mm) and greater than $d_1$. In certain embodiments, $d_2$ is from 50 to 500 mm (e.g., from 100 to 250 mm; e.g. from 150 to 250 mm; e.g., from 220 to 250 mm) and greater than $d_1$. In certain embodiments, $w_{max}$ is less than or equal to 2 mm (e.g., less than or equal to 1.5 mm; e.g., less than or equal to 1 mm). In certain embodiments, $w_{max}$ is approximately 1 mm. In certain embodiments, $w_{max}$ is approximately 0.5 mm.

In certain embodiments, a half-angle divergence of the associated beam of excitation light after passing through the focusing optic is less than or equal to 25 mrad (e.g., less than or equal to 20 mrad; e.g., less than or equal to 15 mrad).

In certain embodiments, the beam shaping optic is the collimating optic.

In certain embodiments, the collimating optic is positioned [e.g., with respect to (i) the galvanometer optical scanner and (ii) the output of the associated excitation source (e.g., a distal end of a fiber of a fiber coupled excitation source or a fiber laser from which the beam of excitation light is emitted; e.g., a laser aperture of a free space laser from which the beam of excitation light is emitted] such that a spot size of the associated beam of excitation light is less than or approximately equal to 1 mm in diameter at all locations at the object plane within the respective scan region of the associated excitation source.

In certain embodiments, a half-angle divergence, $\varphi$, of the associated beam of excitation light after passing through the collimating optic is such that $$\tan(\varphi) < \frac{w_{max} - w_{bw}}{2(d_0^{(2)} + d_2)},$$

wherein: $w_{max}$ is an upper bound for a desired spot size of the associated beam of excitation light within the respective scan region of the associated excitation source [e.g., approximately 1 mm, e.g., a scattering length of the excitation light within a diffuse media (e.g., tissue) of a subject to be imaged], $w_{bw}$ is a spot size of the associated beam of excitation light at a beam waist location [e.g., wherein the beam waist location lies at the output of the associated excitation source (e.g., a distal end of a fiber of a fiber coupled excitation source or a fiber laser from which excitation light is emitted; e.g., a laser aperture of a free space laser from which the respective beam of excitation light is emitted)], $d_0^{(2)}$ is a distance from the collimating optic to the galvanometer optical scanner measured along the optical path from the output of the associated excitation source to the galvanometer optical scanner, and $d_2$ is a maximal distance along a maximal length optical path from the galvanometer optical scanner to the respective scan region of the associated excitation source (e.g., wherein $d_2$ is measured from the galvanometer optical scanner to a location at a corner of the respective scan region of the associated excitation source).

In certain embodiments, $d_0^{(2)}$ is at least 50 mm (e.g., at least 100 mm). In certain embodiments, $d_0^{(2)}$ is less than or equal to 250 mm (e.g., less than or equal to 200 mm). In certain embodiments, $d_0^{(2)}$ is from 50 mm to 200 mm (e.g., from 50 to 180 mm). In certain embodiments, $d_2$ is at least 100 mm (e.g., at least 150 mm). In certain embodiments, $d_2$ is less than or equal to 500 mm (e.g., less than or equal to 250 mm). In certain embodiments, $d_2$ is from 50 to 500 mm (e.g., from 100 to 250 mm; e.g. from 150 to 250 mm). In certain embodiments, $w_{max}$ is less than or equal to 2 mm (e.g., less than or equal to 1.5 mm; e.g., less than or equal to 1 mm). In certain embodiments, $w_{max}$ is approximately 1 mm. In certain embodiments, $w_{max}$ is approximately 0.5 mm In certain embodiments, a half-angle divergence of the associated beam of excitation light after passing through the collimating optic is less than or equal to 5 mrad (e.g., less than or equal to 2 mrad; e.g., less than or equal to 1.5 mrad; e.g., less than or equal to 1.25 mrad).

In certain embodiments, a power of at least one excitation source of the plurality of excitation sources is greater than or approximately equal to 100 mW (e.g., greater than or approximately equal to 200 mW; e.g., greater than or approximately equal to 200 mW; e.g., greater than or approximately equal to 300 mW).

In certain embodiments, at least one excitation source of the plurality of excitation sources is a fiber coupled laser or a fiber laser and the output of the at least one excitation source from which the beam of excitation light is emitted is a distal end an optical fiber of the fiber coupled laser or fiber laser.

In certain embodiments, a core diameter of the optical fiber of the fiber coupled laser or fiber laser is from 5 µm to 400 µm (e.g., wherein the optical fiber is a single mode optical fiber having a core diameter from 5 to 10 µm; e.g. wherein the optical fiber is a multi-mode optical fiber having a core diameter from 50 to 400 µm). In certain embodiments, a numerical aperture (NA) of the optical fiber is from 0.1 to 0.3 (e.g., from 0.1 to 0.25; e.g., from 0.15 to 0.25).

In certain embodiments, at least one excitation source of the plurality of excitation sources is a free space laser, wherein the output of the at least one excitation source from which the beam of excitation light is emitted is a laser aperture of the free space laser.

In certain embodiments, the one or more detectors comprises a focal plane array (FPA) detector (e.g., a CCD camera; e.g., a CMOS camera) comprising a plurality of pixels, wherein the FPA detector is aligned to image at least a portion of each respective scan region of each excitation source (e.g., such that a field of view of the FPA detector comprises at least a portion of each respective scan region).

In certain embodiments, the one or more detectors comprises a fiber bundle comprising a plurality of fibers, each of which is aligned to collect light emitted from a different location within the scan region and guides the collected light to a corresponding single element detector (e.g., a Si PD).

In certain embodiments, the one or more detectors are aligned and operable to detect the fluorescent light emitted from the fluorescent species in a transillumination geometry, wherein each respective beam of excitation light is directed towards the object plane from a first side of the object plane and the one or more detectors are aligned and operable (e.g., aligned) to detect fluorescent light emitted in directions outwards from an opposite second side (e.g., opposite to the first side) of the object plane (e.g., wherein the one or more detectors are on an opposite side of the object plane from the galvanometer optical scanner).

In certain embodiments, the one or more subjects is a small animal (e.g., mice, rats, voles, rabbits, hamsters, and similarly-sized animals).

In certain embodiments, a thickness of at least one of the one or more subjects is approximately 1 cm.

In certain embodiments, the one or more subjects are positioned across the object plane using an animal holder operable to secure a plurality of small animals (e.g., wherein the animal holder comprises a plurality of mounts, each mount operable to secure a small animal during imaging).

In certain embodiments, the animal holder comprises one or more optical baffles [e.g., each of the one or more baffles corresponding to a structure protruding outwards from the animal holder in a direction substantially perpendicular to the object plane forwards (e.g., in the direction from which the beam of excitation light is incident on the object plane) and/or backwards (e.g., in the opposite direction from which the beam of excitation light is incident on the object plane), each baffle substantially opaque to light having a wavelength of the excitation light and/or the emitted fluorescent light and located in between two positions where small animals are secured by the animal holder (e.g., in order to reduce/eliminate cross talk)].

In certain embodiments, the tomographic imaging is performed in vivo.

In certain embodiments, step (b) comprises detecting, with the one or more detectors, for at least one excitation source of the plurality of excitation sources, excitation light emitted by the at least one excitation source that is transmitted through or reflected from the one or more subjects [e.g., detecting an excitation image (e.g., a 2D image) corresponding to each of the discrete excitation locations within the respective scan region of the at least one excitation source], step (c) comprises receiving and/or accessing data corresponding to the detected excitation light [e.g., the data comprising an excitation signal (e.g., an excitation image (e.g., a 2D image)) detected following transmission of the excitation light through or reflection of the excitation light by the one or more subjects when the excitation light is directed towards each of a plurality of discrete excitation locations across the respective scan region of the at least one excitation source], and step (d) comprises obtaining (e.g., computing) the one or more tomographic images of the one or more subjects using the data corresponding to the detected excitation light and the data corresponding to the detected fluorescent light (e.g., by performing tomographic reconstruction).

In certain embodiments, for at least one excitation source of the plurality of excitation sources: step (a) comprises using the galvanometer optical scanner to direct the respective beam of excitation light to a plurality of discrete excitation locations within the respective scan region, wherein, for each discrete excitation location, a given subject of the one or more subjects that is positioned in the path of the respective beam of excitation light directed towards the discrete excitation location is illuminated by the respective beam of excitation light at a corresponding illumination location on a surface of the subject, such that the respective beam of excitation light is incident on the surface of the given subject at the corresponding illumination location and diffuses within the subject, thereby exciting of a fluorescent species (e.g., of the one or more fluorescent species) within the given subject (e.g., as a result of diffusion of excitation light from the corresponding illumination location; e.g., thereby exciting a fluorescent species located within a corresponding diffusion volume beneath the surface of the subject into which excitation light incident onto the given subject at the corresponding illumination location diffuses), step (b) comprises, for each discrete excitation location, detecting a corresponding fluorescence emission image (e.g., a 2D image) representing detected fluorescent light emitted from within a given subject positioned in the path of the respective beam of excitation light directed towards the discrete excitation location, as a result of excitation of the fluorescent species within the given subject, thereby detecting a plurality of fluorescence emission images, each corresponding to a discrete excitation location within the respective scan region of the excitation source, step (c) comprises receiving and/or accessing data corresponding to the detected fluorescent light, the data corresponding to the detected fluorescent light comprising the plurality of fluorescence emission images detected for the excitation source, and step (d) comprises obtaining (e.g., computing) the one or more tomographic images of the one or more subjects using the plurality of fluorescence emission images detected for the excitation source.

In certain embodiments, for at least one excitation source of the plurality of excitation sources: step (b) comprises, for each discrete excitation location within the respective scan region of the excitation source, detecting, with the one or more detectors, a corresponding excitation image representing excitation light emitted by the excitation source that is transmitted through or reflected by the given subject when the respective beam of excitation light is incident on the surface of the given subject at the corresponding illumination location, thereby detecting a plurality of excitation images, each corresponding to a discrete excitation location within the respective scan region of the excitation source, step (c) comprises receiving and/or accessing data corresponding to the detected excitation light, the data corresponding to the detected excitation light comprising the plurality of fluorescence emission images detected for the excitation source, and step (d) comprises obtaining (e.g., computing) the one or more tomographic images of the one or more subjects using the plurality of fluorescence emission images detected for the excitation source and the plurality of excitation images detected for the excitation source.

In certain embodiments, for at least one excitation source of the plurality of excitation sources (e.g., for each excitation source of the plurality of excitation sources): step (a) comprises using the galvanometer optical scanner to direct the respective beam of excitation light emitted by the excitation source to a plurality of discrete excitation locations within the respective scan region of the excitation source, wherein: the discrete excitation locations are arranged in sets, each set comprising a plurality of discrete excitation locations, each discrete excitation location of a given set corresponding to a different subject of the one or more subjects (e.g., wherein each set comprises a discrete excitation location corresponding each subject of the one or more subjects), the galvanometer optical scanner is operable to scan the respective beam of excitation light one set at a time, directing the respective beam of excitation light to each discrete excitation location within a given set before proceeding on to a next set (e.g., directing the respective beam of excitation light to each discrete excitation location within a first set before directing the respective beam of excitation light to each discrete excitation location within a second set), and the galvanometer optical scanner is operable to scan the respective beam of excitation light through all the discrete excitation locations of given set within a time corresponding to an exposure window of the one or more detectors, and step (b) comprises, for each set of discrete excitation locations, detecting a corresponding fluorescence emission image representing detected fluorescent light emitted during the exposure window of the one or more detectors as a result of excitation of the one or more fluorescent species within the one or more subjects by excitation light emitted by the excitation source and directed to each excitation location within a given set (e.g., such that each fluorescence emission image is a multi-subject fluorescence emission image that represents detected fluorescent light emitted from within each of the one or more subjects, by a fluorescent species within each subject).

In certain embodiments, the data corresponding to the detected fluorescent light comprises, for each set of discrete excitation locations, the corresponding fluorescence emission image, and step (d) comprises obtaining (e.g., computing) a tomographic image for each subject of the one or more subjects using the fluorescence emission images (e.g., each corresponding to a set of discrete excitation locations) (e.g., by performing tomographic reconstruction).

In certain embodiments, step (d) comprises, for each subject of the one or more subjects: for each fluorescence emission image corresponding to each set of discrete excitation locations, determining a portion of the fluorescence emission image associated with the subject (e.g., the determined portion representing detected fluorescent light emitted from within the subject; e.g., using a co-registered bright field image to identify a spatial region of the fluorescence emission image corresponding to the subject), thereby determining a single subject fluorescence emission image associated with the subject and corresponding to the set of discrete excitation locations, thereby determining a plurality of single subject fluorescence emission images associated with the subject, wherein each single subject fluorescence image corresponds to a set of discrete excitation locations; and obtaining (e.g., computing) a tomographic image (e.g., a 3D tomographic image) of the subject using the plurality of single subject fluorescence emission images associated with the subject.

In certain embodiments, step (b) comprises, for each set of discrete excitation locations, detecting a corresponding excitation image representing detected excitation light transmitted through or reflected by the one or more subjects during the exposure window of the one or more detectors as a result of illumination of the one or more subjects by the respective beam of excitation light directed to each excitation location within a given set (e.g., such that each excitation image is a multi-subject excitation image that represents detected excitation light transmitted through or reflected by each of the one or more subjects), step (c) comprises receiving and/or accessing data corresponding to the detected excitation light, the data corresponding to the detected excitation light comprising, for each set of discrete excitation locations, the corresponding excitation image, and step (d) comprises obtaining (e.g., computing) a tomographic image for each subject of the one or more subjects using the fluorescence emission images and the excitation images (e.g., by performing tomographic reconstruction; e.g., using the fluorescence emission images and the excitation images, each of which corresponds to a set of discrete excitation locations).

In certain embodiments, step (d) comprises, for each subject of the one or more subjects: for each fluorescence emission image corresponding to each set of discrete excitation locations, determining a portion of the fluorescence emission image associated with the subject (e.g., the determined portion representing detected fluorescent light emitted from within the subject; e.g., using a co-registered bright field image to identify a spatial region of the fluorescence emission image corresponding to the subject), thereby determining a single subject fluorescence emission image associated with the subject and corresponding to the set of discrete excitation locations, thereby determining a plurality of single subject fluorescence emission images associated with the subject, wherein each single subject fluorescence emission image corresponds to a set of discrete excitation locations; for each excitation image corresponding to each set of discrete excitation locations, determining a portion of the excitation image associated with the subject (e.g., the determined portion representing detected excitation light transmitted through or reflected by the subject; e.g., using a co-registered bright field image to identify a spatial region of the excitation image corresponding to the subject), thereby determining a single subject excitation image associated with the subject and corresponding to the set of discrete excitation locations, thereby determining a plurality of single subject excitation images associated with the subject, wherein each single subject excitation image corresponds to a set of discrete excitation locations; and obtaining (e.g., computing) a tomographic image (e.g., a 3D tomographic image) of the subject using the plurality of single subject fluorescence emission images associated with the subject and the plurality of single subject excitation images associated with the subject.

BRIEF DESCRIPTION OF THE FIGURES

The file of this patent contains at least one drawing executed in color. Copies of this patent with color drawing(s) will be provided by the Patent and Trademark Office upon request and payment of the necessary fee.

The foregoing and other objects, aspects, features, and advantages of the present disclosure will become more apparent and better understood by referring to the following description taken in conjunction with the accompanying drawings, in which:

FIG. 1A is a schematic showing a layout of a system for rapidly scanning a beam of excitation light across a large field of view, according to an illustrative embodiment.

FIG. 3A is a schematic showing a layout of a system for simultaneously aligning multiple lasers to a galvanometer optical scanner, according to an illustrative embodiment.

Figure 1B:
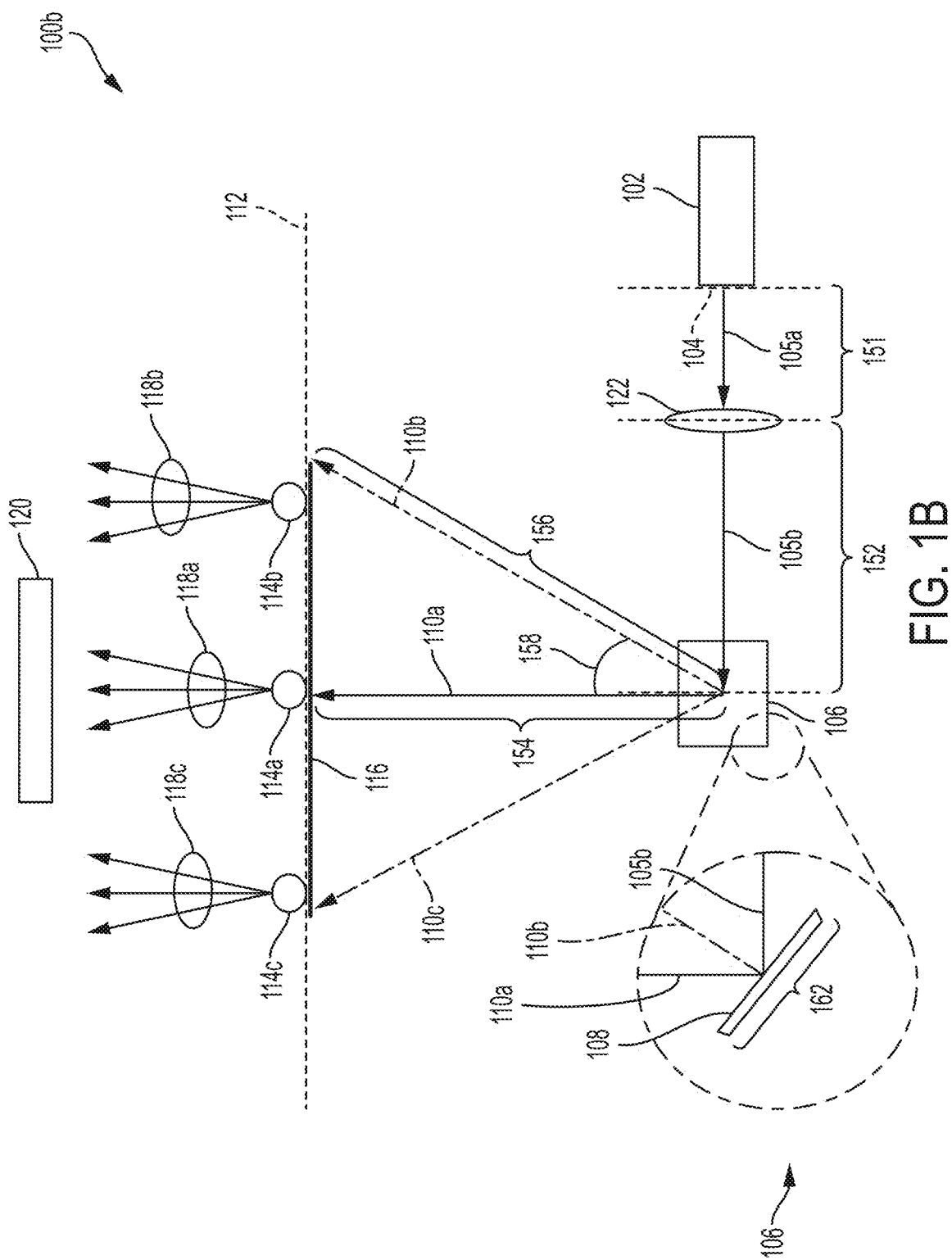
FIG. 1B is a schematic showing a layout of a system for rapidly scanning a beam of excitation light across a large field of view, including a beam shaping optic, according to an illustrative embodiment.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

Definitions

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context and except where such number would exceed 100% of a possible value.

Image: As used herein, the term "image"—for example, a 3-D image of mammal—includes any visual representation, such as a photo, a video frame, streaming video, as well as any electronic, digital or mathematical analogue of a photo, video frame, or streaming video. Any apparatus described herein, in certain embodiments, includes a display for displaying an image or any other result produced by the processor. Any method described herein, in certain embodiments, includes a step of displaying an image or any other result produced via the method.

3-D, three-dimensional: As used herein, the terms "3-D" or "three-dimensional" with reference to an "image" means conveying information about three dimensions. A 3-D image may be rendered as a dataset in three dimensions and/or may be displayed as a set of two-dimensional representations, or as a three-dimensional representation. In certain embodiments, a 3-D image is represented as voxel (e.g., volumetric pixel) data.

Map: As used herein, the term "map" is understood to mean a visual display, or any data representation that may be interpreted for visual display, which contains spatially-correlated information. For example, a three-dimensional map of a given volume may include a dataset of values of a given quantity that varies in three spatial dimensions throughout the volume. A three-dimensional map may be displayed in two-dimensions (e.g., on a two-dimensional screen, or on a two-dimensional printout).

Fluorescence image, emission image: As used herein, the terms "fluorescence image" and "emission image" are understood to mean an image acquired at a wavelength corresponding to an emission wavelength of a fluorescent agent or probe.

Excitation image: As used herein, the term "excitation image" is understood to mean an image acquired at a wavelength corresponding to a wavelength of excitation light emitted by an excitation source.

Electromagnetic radiation, radiation: As used herein, the terms "electromagnetic radiation" and "radiation" is understood to mean self-propagating waves in space of electric and magnetic components that oscillate at right angles to each other and to the direction of propagation, and are in phase with each other. Electromagnetic radiation includes: radio waves, microwaves, red, infrared, and near-infrared light, visible light, ultraviolet light, X-rays and gamma rays.

Optical path: As used herein, the term "optical path" refers to the path that a beam of light travels as it propagates and is directed by various optical elements (e.g., lenses, mirrors, polarizers, beam-splitters, and the like) of an optical system. Optical elements may direct a beam of light by a variety of physical mechanisms, such as reflection, refraction, and the like. An optical path from a first point to a second point refers to the path that a beam of light travels from the first point to the second point, accounting for direction (e.g., via reflection, refraction, and the like) by any optical elements in between the first and second points.

Optical path length, distance along an optical path: As used herein, the term "optical path length" refers to the geometric length of the optical path a beam of light follows as it propagates between two points. Similarly, the term "distance", when referring to a distance along a particular optical path, refers to the geometric distance that a beam of light travels when propagating along the particular optical path.

Detector: As used herein the term "detector" includes any detector of electromagnetic radiation including, but not limited to, CCD cameras, photomultiplier tubes, photodiodes, and avalanche photodiodes.

Galvanometer optical scanner: As used herein, the term "galvanometer optical scanner" refers to an optical system component comprising one or more rotating galvanometer mirrors. A galvanometer optical scanner allows a beam of light to be scanned across a plurality of locations in a target plane a given distance away from the galvanometer optical scanner. This is achieved by directing a beam of light to the galvanometer optical scanner along an appropriately aligned optical path. The beam of light directed into the galvanometer optical scanner is reflected by the one or more galvanometer mirrors in succession and directed outwards, towards the target plane, in a direction defined by one or more optical scan angles. Typically, each optical scan angle is associated with a particular galvanometer mirror and determined by an angle at which the associated galvanometer mirror reflects the beam of light. Rotating a given galvanometer mirror varies the angle at which it reflects the beam of light, and thus varies the associated optical scan angle. Accordingly, rotating the galvanometer mirrors of the galvanometer optical scanner varies the one or more optical scan angles and, thus, the direction in which the beam of light is directed outwards from the galvanometer optical scanner. As a given galvanometer mirror is rotated, its associated optical scan angle is varied, and a location at which it intersects the target plane is varied along a particular direction.

In certain embodiments, a galvanometer optical scanner comprising a single galvanometer mirror, which can be used to scan a beam of light through a plurality of locations along a particular direction in a target plane. Rotation of the galvanometer mirror thus scans the beam of light across a one-dimensional scan region (e.g., a line) of the object plane.

In certain embodiments, a galvanometer optical scanner comprises two rotating galvanometer mirrors such that a beam of light can be scanned through a plurality of locations along two directions. Rotating the two galvanometer mirrors together thus allows a beam of light to be raster scanned across a two-dimensional region of the target plane. In certain embodiments, the galvanometer mirrors are aligned such that a first galvanometer mirror varies a first optical scan angle in a first direction and a second galvanometer mirror varies a second optical scan angle in a second direction that is substantially orthogonal to the first direction. Variation of the first optical scan angle (e.g., via rotation of the first galvanometer mirror) varies a position at which the beam of light directed outwards from the galvanometer optical scanner intersects the target plane in a first direction. Variation of the second optical scan angle (e.g., via rotation of the second galvanometer mirror) varies a position at which the beam of light directed outwards from the galvanometer optical scanner intersects the target plane in a second direction. Accordingly, the first and second galvanometer mirrors can be rotated together to raster scan a beam of light across a two dimensional scan region of the target plane.

As used herein, directing a beam of light "to a galvanometer optical scanner" is understood to mean directed the beam of light along an appropriately aligned optical path to the galvanometer optical scanner such that it is incident on, and reflected by each of the one or more galvanometer mirrors that the galvanometer optical scanner comprises. As used herein, a distance to a galvanometer optical scanner (e.g., along a particular optical path, from a particular location) is understood to mean a distance to a first galvanometer mirror on which the beam of light incident. As used herein, a distance from a galvanometer optical scanner (e.g., along a particular optical path, to a particular location) is understood to mean a distance from the first galvanometer mirror on which a beam of light directed to the galvanometer optical scanner is incident, including distance traveled as it is reflected by any other mirrors that the galvanometer optical scanner comprises.

Forward model: As used herein, the term "forward model" is understood to mean a physical model of light propagation (e.g., photon transport) in a given medium from a source to a detector.

Tomographic image: As used herein, the term "tomographic image" may refer, for example, to an optical tomographic image, an x-ray tomographic image, a tomographic image generated by magnetic resonance, positron emission tomography (PET), magnetic resonance, (MR) single photon emission computed tomography (SPECT), and/or ultrasound, and any combination of these.

Diffuse medium, diffusive medium: As used herein, the terms "diffuse medium" and "diffusive medium" are used interchangeably and are understood to mean media where waves suffer multiple scattering events with small particles (the scatterers) within an otherwise homogeneous medium, randomizing their phase; in this case it is the average wave intensity that is studied. The average wave intensity will follow the diffusion equation, behaving in itself as a "diffuse wave" and interacting with surfaces and boundaries.

Object plane: As used herein, the term "object plane" refers to an idealized two-dimensional imaging plane of an optical imaging system at, or in proximity to which, one or more objects (e.g., subjects) to be image are located.

Excitation source: As used herein, the term "excitation source" refers to a light source such as a laser that is used to provide light to an optical system for optical excitation of fluorescence. In certain embodiments, the excitation source emits a beam of excitation light from an output of the excitation source. Excitation light from the excitation source may then be provided to the optical system by directing the beam of excitation light from the output of the excitation source to various optical components (e.g., optics, mirrors, galvanometer optical scanners, and the like) of the optical system.

Optic: As used herein, the term "optic" refers to a collection of one or more optical elements that is used to shape a beam of light using one or more lenses. When various parameter of optics (e.g., focusing optics; e.g., collimating optics), such as focal length, clear aperture, and the like are described herein, they are understood to refer to a property of the optic—that is, a net effect of all the optical elements that the optic comprises, rather than a property of any one of the individual elements of the optic.

Spot size: As used herein, the term "spot size" refers to a measure of a diameter of a beam of light measured at a particular position and in an orthogonal plane that is substantially orthogonal to the direction of propagation of the beam of light. In certain embodiments, spot size refers to a measure of diameter of the beam of light corresponding to a distance measured along a line within the orthogonal plane between a first and second location along the line where a signal representing the intensity of the beam of light (e.g., as detected by a detector) falls to below a predefined fraction of the maximal intensity (e.g., half the maximal intensity; e.g., $1/e^2$ of the maximal intensity) of the beam of light. For example, spot size may correspond to a full-width at half maximum measured along a particular line in the orthogonal plane (e.g., line along an x-axis; e.g., a line alone ay-axis). In certain embodiments, spot size refers to a measure of the diameter of the beam of light corresponding to a function of two or more distances each measured along a different line within the orthogonal plane as described above. For example, spot size may be measured as a maximum value of a first distance, measured along a first line within the orthogonal plane and a second distance, measured along a second line within the orthogonal plane. In certain embodiments the second line is orthogonal to first line.

Subject: As used herein, the term "subject" refers to an individual that is imaged. In certain embodiments, the subject is a human. In certain embodiments, the subject is a small animal.

Small animal: As used herein, a "small animal" refers to small mammals that can be imaged with a microCT and/or micro-MR imager. In some embodiments, "small animal" refers to mice, rats, voles, rabbits, hamsters, and similarly-sized animals.

DETAILED DESCRIPTION

It is contemplated that systems, architectures, devices, methods, and processes of the claimed invention encompass variations and adaptations developed using information from the embodiments described herein. Adaptation and/or modification of the systems, architectures, devices, methods, and processes described herein may be performed, as contemplated by this description.

Throughout the description, where articles, devices, systems, and architectures are described as having, including, or comprising specific components, or where processes and methods are described as having, including, or comprising specific steps, it is contemplated that, additionally, there are articles, devices, systems, and architectures of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Documents are incorporated herein by reference as noted. Where there is any discrepancy in the meaning of a particular term, the meaning provided in the Definition section above is controlling.

Headers are provided for the convenience of the reader— the presence and/or placement of a header is not intended to limit the scope of the subject matter described herein.

Described herein are systems and methods that facilitate fast tomographic imaging over a wide field of view. In particular, in certain embodiments, the systems and methods described herein allow a beam of excitation light to be rapidly scanned through a plurality of locations across a large scan region of an object plane. In this manner, one or more subjects positioned across the object plane, in the path of the beam of excitation light as it is directed from the galvanometer optical scanner to various locations within the scan region, are illuminated at a plurality of illumination locations as the beam of excitation light is scanned from location to location.

In particular, in certain embodiments, the beam of excitation light is directed by the galvanometer optical scanner to a plurality of discrete excitation locations within the scan region. A given subject positioned within the optical path of the beam of excitation light directed to a given excitation location is illuminated by the beam of excitation light at an associated illumination location at the surface of the subject. The beam of excitation light is incident on the surface of the subject at the associated illumination location, and diffuses within the subject. As the excitation light diffuses within the subject, it excites fluorescent species within the subject (e.g., within a diffusion volume corresponding to the illumination location), and causes them to emit fluorescent light.

As the excitation beam is scanned from excitation location to excitation location the resulting fluorescent light associated with each excitation location is detected by one or more detectors. Data corresponding to the detected fluorescent light is then used to create tomographic images (e.g., three-dimensional tomographic images) of the one or more subjects.

In certain embodiments, the optical elements that direct the beam of excitation light to the object plane and the detectors are aligned in a transillumination geometry. In transillumination, the one or more subjects are illuminated from one side of the object plane and fluorescent light emitted outwards and away from the opposite side of the object plane is detected. In this manner, each of the one or more subjects is illuminated on one side (e.g., a dorsal side) and fluorescent light emitted on the other side of the subject (e.g., a ventral side) is detected.

In certain embodiments, the optical elements that direct the beam of excitation light to the object plane and the detectors are aligned in an epi-illumination (e.g., reflectance) geometry. In epi-illumination, the one or more subjects are illuminated one side of the object plane and fluorescent light emitted outwards on the same side of the object plane is detected.

In certain embodiments, this transillumination approach provides several advantages over epi-illumination or reflectance geometries. These advantages include improved imaging deep within tissue (depth sensitivity) and reduced excitation light leakage, which are particularly relevant for fluorescence optical tomography.

Conventional trans-illumination based fluorescence optical tomography systems use a scanning fiber to illuminate a subject to be imaged at multiple excitation locations. An excitation source is coupled to the scanning fiber such that excitation light is emitted out of its distal end. The distal end of the fiber is mounted on one or more linear translation stages and placed in close proximity to the object plane. In order to scan a plurality of locations across the object plane, the fiber is physically translated along directions parallel to the object plane (e.g., raster scanned along two dimensions) by the linear translation stages, maintaining a fixed distance between the distal end of the fiber and the object plane.

Focusing optics are attached to the distal end of the fiber to focus light emitted from the fiber to small (e.g., less than 1 mm in diameter) to a focused spot at the object plane. Because of the fixed and small (e.g., less than 115 mm) fiber end to object plane distance, optical requirements are relatively relaxed, and relatively short focal length (e.g., less than 30 mm) focusing optics are typically used to achieve required spot sizes at the object plane.

Accordingly, such conventional tomographic imaging systems are limited by the need to physically translate a fiber end across a scan region in order to illuminate multiple locations within a subject. Physical translation of a fiber end is a slow process. Moreover, in order to image over a large area, and for example, image multiple subjects, multiple scanning illumination fibers may be required (e.g., one for each subject). Such an approach dramatically increases system complexity.

The approaches described herein utilize an optical system design that addresses these limitations, and eliminates the need for motorized stages to translate a fiber end across a scan region, thereby significantly increasing scan speeds. As will be described in the following, in certain embodiments, the systems and methods described herein utilize beams of excitation light with specifically tailored shapes to maintain small spot sizes (e.g., less than or equal to 1 mm in diameter) of the beam of excitation light as it is scanned across the scan region. The ability to scan over a large region while still maintain small spot sizes allows for accurate, high-resolution tomographic imaging over a large field of view that can accommodate large and/or multiple subjects.

For example, in certain embodiments, the tomographic imaging systems and methods described herein allow for multiple subjects, such as multiple small animals to be quickly imaged together using a single scan. Additionally, as will be described in detail in the following, in certain embodiments, use of a fast scanning galvanometer optical scanner allows a tomographic imaging approach wherein the beam of excitation light is directed to multiple excitation locations during a single exposure of a detector (e.g., a CCD camera). This allows, for example fluorescent signal from each of a plurality of subjects to be detected during a single exposure of the detector, and reduces time required to obtain tomographic images of each of the subjects.

The described beam shaping approaches can also facilitate imaging of thick objects by reducing the amount that the size of the beam of excitation light varies away from the object plane, as well as allowing high powered lasers to be used.

Additionally, the systems and methods described herein include approaches that provide for multiple excitation sources to be incorporated into a single system and switched between in a robust and efficient manner. This approach removes the need to switch between different excitation sources that may be required for different measurements, eliminating time-consuming alignment required to switch between excitation sources, which also introduces variability (e.g., from measurement to measurement; e.g., due to the need to re-align excitation sources). In certain embodiments, the approaches for incorporating multiple excitation sources into a single system also facilitates multi-spectral imaging applications.

A. Beam Scanning with Rotating Galvanometer Mirrors

In certain embodiments, the systems and methods described herein utilize a galvanometer optical scanner to scan a beam of excitation light across multiple locations of an object plane. FIG. 1A shows an example of an optical system 100a layout for rapidly scanning a beam of excitation light across a scan region 116 of an object plane 112 using a galvanometer optical scanner 106. As shown in FIG. 1A, an excitation source 102 operable to emit a beam of excitation light is aligned to direct the beam of excitation light from its output 104 along an optical path 105 from the output 104 to the galvanometer optical scanner 106.

The galvanometer optical scanner 106 comprises one or more rotating galvanometer mirrors. The galvanometer optical scanner 106 is aligned and operable to direct the beam of excitation light to a plurality of locations within the scan region 116 of the object plane via reflection by the one or more rotating galvanometer mirrors (e.g., 108). The rotating galvanometer mirrors (e.g., 108) of the galvanometer optical scanner reflect the beam of excitation light towards the object plane 112 in a direction defined by one or more an optical scan angles. As the one or more galvanometer mirrors are rotated, the optical scan angles, and accordingly, the direction at which the beam of excitation light is directed towards the object plane is varied. In this manner, as the one or more galvanometer mirrors are rotated, the beam of excitation light is scanned across the scan region.

Galvanometer mirrors are capable of rotating at sufficient speeds to scan a beam of excitation light through a plurality of points in a scan region as large as 140 mm by 140 mm in times on the order of 100 µs Additionally, as will be described in the following, galvanometer mirrors can be rotated sufficiently quickly to direct a beam of excitation light to multiple excitation locations within a scan region during a single exposure window of a detector.

In certain embodiments, each scan angle is associated with, and determined by rotation of a particular galvanometer mirror. Typically, each galvanometer mirror rotates within a given rotational plane and, accordingly, varies its associated optical scan angle within a corresponding scan plane. Accordingly, by varying its associated optical scan angle within the corresponding scan plane, a given galvanometer mirror can be rotated to vary the position of the beam of excitation light along a particular direction across the object plane. Thus, each galvanometer mirror is associated with a specific direction across the object plane and controls (e.g., via its rotation) scanning of the beam of excitation light along that direction.

In certain embodiments, the beam scanning approaches described herein utilize a galvanometer optical scanner 106 comprising two galvanometer mirrors that are aligned so as to scan the beam of excitation light in two orthogonal directions across the object plane. A first galvanometer mirror scans the beam of excitation light along an associated first direction across the object plane (e.g., an x-direction). A second galvanometer mirror scans the beam of excitation light along an associated second direction across the object plane (e.g., ay-direction). In certain embodiments, rotation of the first and second galvanometer mirrors together raster scans the beam of excitation light across a two-dimensional scan region of the object plane. In certain embodiments, the size of the scan region is determined by the maximal rotational angles of the first and second galvanometer mirrors and the distance from the galvanometer optical scanner 106 to the object plane 112.

FIG. 1A illustrates how the optical system layout and the paths traveled by the beam of excitation light relate to the scan region size along the first direction, which is associated with (e.g., scanned by) the first galvanometer mirror. The first galvanometer mirror 108 is shown in the inset of FIG. 1A. As shown in FIG. 1A, at a minimal rotational angle of the first galvanometer mirror 108 the beam of excitation light is directed to the object plane 112 at a minimal first optical scan angle towards the object plane. The beam of excitation light travels a minimal distance, $d_1$ (154), along a minimal length optical path 110a from the galvanometer optical scanner 106 to the center of the scan region 116 within the object plane 112.

When the first galvanometer mirror 108 is rotated to produce a maximal first optical scan angle in a positive direction, the beam of excitation light is directed to a location within the object plane 112 at a maximal first optical scan angle, $\theta_{opt}$, (158) in the positive direction. When the beam of excitation light is directed to the object plane 112 at the maximal first optical scan angle (158) in the positive direction, it travels a maximal distance, $d_2$, (156) along a maximal length optical path 110b from the galvanometer optical scanner to a first edge of the scan region 116 in the positive direction along the first direction (e.g., the x-direction). The galvanometer mirror 108 may be rotated in the opposite (e.g., negative) direction, to a maximal angle to direct the beam of excitation light is directed along an optical path 110c to a second (e.g., opposite) edge of the scan region 116 along the first direction.

In certain embodiments, the minimal distance, $d_1$ (154), along the minimal length optical path 130a from the galvanometer optical scanner 106 to the object plane 112 and the maximal first optical scan angle that is produced by the first galvanometer mirror 108 determines the scan size along the first direction. Accordingly, based on the geometry shown in FIG. 1A, in order to produce a scan region having a desired size along the first direction, the galvanometer optical scanner 106 can be positioned such that $d_1 = X \tan \Theta_{opt}$, where X is a center to edge distance of the scan region 116 along the first dimension (e.g., such that the desired scan size along the given dimension is 2X) and $\Theta_{opt}$ is the maximal optical scan angle achievable by rotation of the first galvanometer mirror 108. Typically, a given optical scan angle is twice the rotational angle of the associated galvanometer mirror that controls the given optical scan angle. Accordingly, the maximal first optical scan angle is, in certain embodiments, twice the maximal rotational angle of the first galvanometer mirror.

In certain embodiments, the same considerations described above for determining a size of the scan region 116 along the first dimension produced by rotation of the first galvanometer mirror can be used to determine a size of the scan region 116 along a second direction that is scanned by a second galvanometer mirror of the galvanometer optical scanner 106. In this manner, the galvanometer optical scanner 106 can be positioned a specific distance, measured along a minimal length optical path from the galvanometer optical scanner to a location within the scan region, to produce a scan region of a desired size, based on one or more maximal rotational angles of the one or more (e.g., first and second) galvanometer mirrors. For a two-dimensional scan region, the minimal length optical path corresponds to an optical path from the galvanometer optical scanner to a central location of the two-dimensional scan region, as in the one dimensional example described above. The maximal length optical path, having length $d_2$, however, corresponds to an optical path from the galvanometer optical scanner to a location at a corner of the two dimensional scan region.

In certain embodiments, the desired scan size is set to allow multiple subjects positioned across the object plane small animals to be imaged in a single scan. For example, FIG. 1A shows three subjects 114a, 114b, and 114c position across the scan region. A size of the scan region may be set, based on a desired number of subjects to be imaged, their size, and the separation between subjects. For example, in order to image three mice, each of which is 25 mm wide, with 45 mm in between, a scan size of 140 mm by 140 mm is appropriate.

In certain embodiments, the size of the scan region (e.g., the desired scan size) along a first dimension and/or a second dimension is at least 100 mm. In certain embodiments the size of the scan region (e.g., the desired scan size) along a first dimension and/or a second dimension is at least 150 mm. In certain embodiments the size of the scan region (e.g., the desired scan size) along a first dimension and/or a second dimension is at least 200 mm. In certain embodiments the size of the scan region (e.g., the desired scan size) along a first dimension and/or a second dimension is from 100 to 500 mm. In certain embodiments the size of the scan region (e.g., the desired scan size) along a first dimension and/or a second dimension is from 100 to 200 mm. In certain embodiments the size of the scan region (e.g., the desired scan size) along a first dimension and/or a second dimension is from 100 to 150 mm.

In certain embodiments, the minimal distance, $d_1$, along the minimal length optical path from the galvanometer optical scanner to a location within the scan region is at least 100 mm. In certain embodiments, the minimal distance, $d_1$, along the minimal length optical path from the galvanometer optical scanner to a location within the scan region is at least 150 mm. In certain embodiments, the minimal distance, $d_1$, along the minimal length optical path from the galvanometer optical scanner to a location within the scan region is at least 200 mm. In certain embodiments, the minimal distance, $d_1$, along the minimal length optical path from the galvanometer optical scanner to a location within the scan region is from 150 mm to 250 mm. In certain embodiments, the minimal distance, $d_1$, along the minimal length optical path from the galvanometer optical scanner to a location within the scan region is approximately 200 mm.

In certain embodiments, the system comprises an animal holder for securing multiple small animals during imaging. The animal holder may be placed at the object plane, in the scan region to allow for the animals it holds to be scanned by the beam of excitation light, such that excitation light directed towards a given excitation location within the scan region is incident on a particular subject, causing excitation of fluorescent species within the as it diffuses below the surface and within the subject.

B. Excitation Source Beam Shaping

In certain embodiments, the beam of excitation light used in the beam scanning technology described herein is shaped such that a required spot size is maintained at all locations within the scan region. For example, for tomographic imaging in a diffuse media, such as tissue, spot sizes below the scattering length of the diffuse media are typically used. For typical tissues relevant for in vivo imaging of small animals, such as muscle, the scattering length is such that spot sizes of less than or equal to 1 mm are used. In certain embodiments, spot sizes of approximately 0.5 mm are used.

Maintaining such small object plane spot sizes throughout a large scan region is non-trivial. In particular, the galvanometer optical scanner based approach described above allows a beam of excitation light to be rapidly scanned through a large scan region extending across the object plane. However, as the beam of excitation light is scanned from location to location across the object plane, the distance that it travels from the galvanometer optical scanner to a given location at the object plane varies from location to location.

In order to ensure that spot size requirements are met, the systems and methods described herein may utilize one of two beam shaping approaches for maintaining a desired spot size throughout the scan region.

In a first approach, a collimated beam of excitation light is used. Ideally, a collimated beam of excitation light maintains a substantially fixed size as it propagates. In practice, the collimated beam diverges slowly as it propagates. In a second approach, a focused beam of excitation light is used. The focused beam converges as it propagates until it reaches a minimal size at its beam waist location, after which it diverges and increases in size.

Appropriately shaped collimated and/or focused beams of excitation light can be produced either directly be the excitation source itself or via use of a beam shaping optic. For example, in certain embodiments, the excitation source itself directly emits either a collimated or gently focused beam of excitation light that satisfies specific requirements, described in the following. This may be achieved via an excitation source that is specifically designed (e.g., by a laser manufacturer) to provide an appropriately shaped beam of excitation light. In certain embodiments, a beam shaping optic is positioned in the optical path from the output of the excitation source to the galvanometer optical scanner to shape the beam of excitation light. The beam shaping optic may be a collimating optic that collimates the beam of excitation light or a focusing optic that produces a gently focused beam of excitation light.

In certain embodiments, the choices of whether to use a collimated or focused beam of excitation light and whether either should be output directly from the excitation source or obtained through the use of a beam shaping optic (e.g., a collimating optic; e.g., a focusing optic) depend on the desired properties of the imaging system, such as an upper bound to a spot size of the excitation beam within the scan region, a desired scan size, and the like. Properties of specific excitation sources to be used are also relevant.

In particular, in certain embodiments, they systems and methods described herein use lasers such as free space lasers, fiber lasers, and fiber coupled lasers. Free space lasers emit excitation light directly into free space, such that an output 104 of a free space laser is a laser aperture from which the excitation light is emitted. Fiber lasers and fiber couple lasers output excitation light from a distal end of an optical fiber. An output 104 of an excitation source 102 corresponding to a fiber laser or an fiber coupled laser is the distal end of the optical fiber of the fiber laser or fiber coupled laser.

In certain embodiments, fiber lasers and fiber coupled lasers are especially compatible with the use of beam shaping optics, such as collimating optics and/or focusing optics.

B.i Direct Output of Shaped Beams of Excitation Light

FIG. 1A illustrates a beam of excitation light traveling directly from the output 104 of an excitation source 102 to the galvanometer optical scanner 106. In certain embodiments, the excitation source is designed such that it is operable to emit an appropriately shaped beam of excitation light directly from its output 104. Accordingly, in certain embodiments, no focusing or collimating optics are placed along the optical path from the excitation source to the galvanometer optical scanner, or along the optical path from the galvanometer optical scanner to the object plane.

In certain embodiments, a size of the galvanometer mirrors of the galvanometer optical scanner 106 sets, in part, an initial beam diameter of the beam of excitation light at the output 104 of the excitation source 102. In particular, the initial beam diameter at the output of the excitation source, along with a distance, $d_0^{(1)}$ (150), along an optical path 105 from the output 104 of the excitation source 102 to the galvanometer optical scanner 106 is set such that the spot size of the beam of excitation light at the galvanometer optical scanner 106 is smaller than the size, $w_{galvo}$ (162), of the galvanometer mirrors of the galvanometer optical scanner 106. In certain embodiments, the size of the galvanometer mirrors of the galvanometer optical scanner can accept a beam of excitation light having a spot size from 3 to 5 mm in diameter.

In certain embodiments, the beam of excitation light emitted from the excitation source is shaped such that its spot size at all locations within the scan region is below a minimum desired spot size. As discussed above, in certain embodiments the minimum spot size within the scan region is determined by a scattering length of the media in which imaging is to be performed. Accordingly, in certain embodiments, for imaging in diffuse media such as tissue, the beam of excitation light is shaped to achieve a spot size of below 1 mm in diameter at all locations within the scan region. In certain embodiments, the beam of excitation light is shaped to achieve a spot size of approximately 0.5 mm.

As the beam of excitation light is scanned across the scan region, a working distance, measured along an optical path from output of the excitation source to the galvanometer optical scanner and from the galvanometer optical scanner to the object plane varies. Appropriate shaping of the beam of excitation light allows spot size requirements to be met at all locations within the scan region, even as the working distance varies as the beam of excitation light is scanned. For example, the schematic of FIG. 1A illustrates the minimal and maximal working distances for a one dimensional scan wherein the beam of excitation light is scanned across a first dimension of the scan region. As shown in FIG. 1A, a minimal distance, $d_1$ (154), along a minimal length optical path from the galvanometer optical scanner 106 to the scan region 116 is determined by a maximum first optical scan angle, $\theta_{opt}$, produced by rotation of the first galvanometer mirror 108, and a desired scan size, 2X. Accordingly, a minimal working distance from the output of the excitation source 104 to the scan region 116 is given by equation (1) below.

$$\text{minimum laser working distance} = d_0^{(1)} + d_1 = d_0^{(1)} + X \tan(\theta_{opt}) \quad (1)$$

In equation (1) above, $d_0^{(1)}$ corresponds to the distance along the optical path from the excitation source to the galvanometer optical scanner. In certain embodiments, $d_0^{(1)}$ has a value in the range from 50 mm to 180 mm.

When the beam of excitation light is directed to a location at an edge of the scan region along the first dimension, the beam of excitation light travels a maximal distance, $d_2$ (156) along a maximal length optical path 110b from the galvanometer optical scanner to the location at the edge of the scan region. Accordingly, the beam of excitation light travels a maximal working distance, given by equation (2) below, from the output 104 of the excitation source to the object plane.

$$\text{maximum laser working distance} = d_0^{(1)} + d_2 = d_0 + X \sin(\theta_{opt}) \quad (2)$$

Equations (1) and (2) above, which are based on a one-dimensional scan across the first dimension of the scan region can readily be extended to describe the minimum and maximum laser working distances for a two-dimensional scan. Equations (3), (4), and (5) below are valid for a two-dimensional scan if both $d_1$ and $d_2$ are determined with respect to a two-dimensional scan, respectively. That is, such that $d_1$ is taken as a minimal distance measured along a minimal length optical path from the galvanometer optical scanner to a location within the two-dimensional scan region, and $d_2$ is a maximal distance along a maximal length optical path from the galvanometer optical scanner to a location within the two-dimension scan region. Accordingly, in certain embodiments, for a two-dimensional scan region the minimal length optical path along which $d_1$ is measured is an optical path from the galvanometer optical scanner to a central location of the two-dimensional scan region. In certain embodiments, for a two-dimensional scan region, the maximal length optical path along which $d_2$ is measured is an optical path from the galvanometer optical scanner to a corner of the two dimensional scan region. In certain embodiments, for a two dimensional scan, X is taken as a distance along a diagonal from the center of the scan region to a corner of the scan region. The distance, $d_0^{(1)}$, along the optical path from the output 104 of the excitation source 102 to the galvanometer optical scanner 106 is independent of whether the scan is along a single direction or within a two-dimensional scan region. In certain embodiments, in order to maintain spot sizes at all locations within the scan region, the excitation source outputs either a collimated or focused beam of excitation light. Both collimated and focused beams vary in size as they propagate through the optical system. The a rate at which a beam of light's size varies as it propagates is determined by a divergence angle, which is the angle at which the beam converges or diverges. The position at which beam has a smallest spot size is referred to as the beam waist location. The smallest spot size of the beam, at the beam waist location, is referred to as the beam waist diameter, $w_{bw}$.

Collimated Beams

In certain embodiments, a collimated beam of excitation light is output by the excitation source. Ideally, a collimated beam of excitation light maintains a substantially fixed size as it propagates. In practice, the collimated beam diverges slowly, such that the beam waist is located at the output 104 (e.g., a laser aperture of a free space laser; e.g., a distal end of an optical fiber of a fiber coupled laser or a fiber laser) of the excitation source 102.

In certain embodiments, in order for the spot size of the beam of excitation light to be less than a maximal desired spot size at all locations within the scan region, the excitation source is designed to emit a collimated beam having a half-angle divergence, $\varphi$, less than an upper bound, such that equation (3) below is satisfied. In equation (3) below, $w_{max}$ is an upper bound for a desired spot size of the beam of excitation light within the scan region (e.g., 1 mm, e.g., a scattering length of the excitation light within a diffuse media (e.g., tissue) of a subject to be imaged).

Figures 8A, 8B:
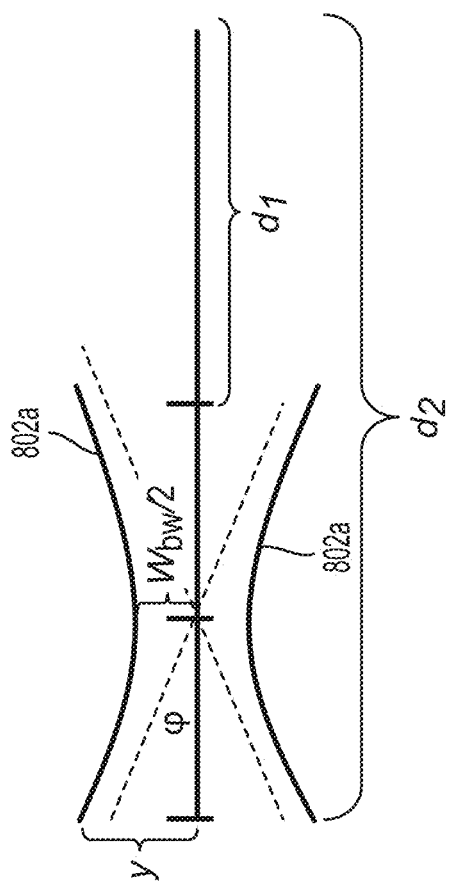
FIG. 8A is a schematic illustrating divergence of a focused beam of excitation light through the object plane, according to an illustrative embodiment.
FIG. 8B is a derivation of an equation for determining a half-angle divergence of a focused beam of excitation light, according to an illustrative embodiment.
Figures 8C, 8D:
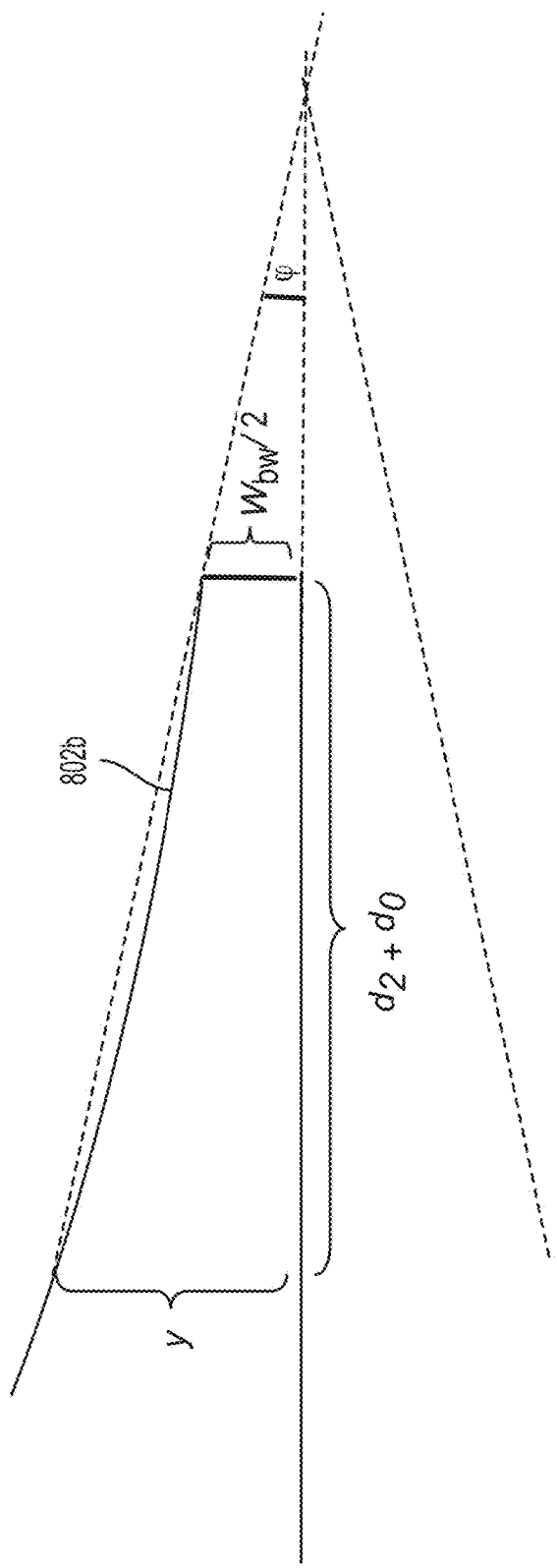
FIG. 8C is a schematic illustrating divergence of a collimated beam of excitation light through the object plane, according to an illustrative embodiment.
FIG. 8D is a derivation of an equation for determining a half-angle divergence of a collimated beam of excitation light, according to an illustrative embodiment.

FIG. 8C illustrates an example cross sectional geometry of a collimated beam of excitation light as it travels from its beam waist location (e.g., at the output of the excitation source), where it has a diameter of $w_{bw}$, along a maximal length working distance to the scan region. As shown in FIG. 8B, the collimated beam of excitation light 802b diverges as it propagates, and, in certain embodiments, reaches a maximal spot size when it travels the maximal distance, $d_0^{(1)}+d_2$ to the scan region. FIG. 8D shows an example derivation of equation (3) below. In certain embodiments, satisfying equation (3) below ensures that the maximal spot size is less than $w_{max}$ such that the spot size at all locations within the scan region is maintained below the $w_{max}$.

$$\tan(\varphi) < \frac{w_{max} - w_{bw}}{2(d_0^{(1)} + d_2)}, \text{ (linear units in mm)} \quad (3)$$

Focused Beams

In certain embodiments, a focused beam of excitation light is output by the excitation source. A focused beam converges as it propagates until it reaches its smallest size at its beam waist location, after which it diverges. In certain embodiments, the focused beam is shaped such that it reaches its beam waist near the object plane, at a location given by equation (4) below.

$$\text{distance from source output to the beam waist} = d_0^{(1)} + \frac{d_1 + d_2}{2} \quad (4)$$

This allows a smallest spot size of the focused beam to be reached near the object plane. Notably, however, since the working distance from the output 104 of the excitation source 102 to the object plane 112 varies as the beam of excitation light is scanned through the scan region 116, various locations in the scan region will be different distances before and after the beam waist location. Accordingly, in certain embodiments, the excitation source emits a focused beam of excitation light that converges (e.g., as it propagates in directions towards its beam waist location) and diverges (e.g., as it propagates away from its beam waist location) sufficiently slowly, such that the spot size of the beam of excitation light to be less than a maximal desired spot size at all locations within the scan region.

In particular, for a focused beam of excitation light that reaches its beam waist location at the location specified by equation (4) above, the excitation source is designed to emit a focused beam having a half-angle divergence, $\varphi$, less than an upper bound, such that equation (5) below is satisfied. As in equation (3) below, $w_{max}$ is an upper bound for a desired spot size of the beam of excitation light within the scan region (e.g., 1 mm, e.g., a scattering length of the excitation light within a diffuse media (e.g., tissue) of a subject to be imaged). FIG. 8A illustrates an example cross sectional geometry of a focused beam of excitation light 802a in the vicinity of its beam waist on which equation (5) below is based. An example derivation of equation (5) below is shown in FIG. 8B As shown in FIG. 8A, in certain embodiments, equation (5) ensures that a spot size of a beam of excitation light is maintained at less than $w_{max}$ both when it travels the minimal laser working distance to a location in the scan region and when it travels the maximal laser working distance to a location in the scan region.

$$\tan(\varphi) < \frac{w_{max} - w_{bw}}{d_2 - d_1}, \text{ (linear units in mm)} \quad (5)$$

Accordingly, excitation sources designed to emit collimated or focused beams of excitation light with the above described properties allow requisite spot sizes to be maintained for all locations within the scan region.

B.ii Beam Shaping Optics for Producing Shaped Beams of Excitation Light

In certain embodiments, a beam of excitation light with an appropriate shape is achieved via a beam shaping optic. For example, turning to FIG. 1B, an example of a layout of an optical system 100b utilizing beam shaping optics is shown. In certain embodiments, a beam shaping optic 122 is positioned in the optical path (105a and 105b together) from the excitation source to the galvanometer optical scanner. The beam shaping optic 122 is positioned a distance, 151, from the output 104 of the excitation source, and a distance, $d_0^{(2)}$ (152) from the galvanometer optical scanner. In this manner, the beam of excitation light emitted by the excitation source 102 travels along an optical path 105a from the output 104 of the excitation source to the beam shaping optic 122 and along an optical path 105b from the beam shaping optic 122 to the galvanometer optical scanner 106.

The beam shaping optic may be used to produce a collimated or focused beam of excitation light. In particular, in certain embodiments, the beam shaping optic is a collimating optic aligned such that after passing through the collimating optic, the beam of excitation light maintains a substantially fixed size, diverging slowly, as it travels (i) towards the galvanometer optical scanner and (ii) from the galvanometer optical scanner to the object plane. In certain embodiments, the beam shaping optic is a focusing optic, wherein the focusing optic is aligned such that after passing through the focusing optic, the beam of excitation light converges as it travels (i) towards the galvanometer optical scanner and (ii) from the galvanometer optical scanner to the object plane [e.g., such that a spot size (e.g., diameter) of the beam of excitation light at the object plane is smaller than an initial size (e.g., diameter) of the beam of excitation light at the focusing optic].

Parameters (e.g., focal lengths) of the beam shaping optic (e.g., a collimating optic, e.g., a focusing optic) and its position in the optical system (e.g., along the optical path from the output of the excitation source to the galvanometer optical scanner) are determined such that a collimated or focused beam of excitation light with appropriate properties is produced when the beam of excitation light passes through the beam shaping optic.

Properties of the beams of excitation light produced via use of a beam shaping optic are similar to those described above with respect to beams of excitation light that are output with desired shapes directly from the excitation source. As described in the following, however, working distances and initial beam diameter are measured with respect to the position of the beam shaping optic 122, as opposed to the output 104 of the excitation source 102.

In certain embodiments, similar to beams of excitation light shaped directly by the excitation source, a size of the galvanometer mirrors of the galvanometer optical scanner 106 sets, in part, an initial beam diameter of the beam of excitation light. Where a beam shaping optic is used, the initial beam diameter is measured at the position of the beam shaping optic 122. In particular, the initial beam diameter at the beam, along with a distance, $d_0^{(2)}$ (152), along an optical path 105b from the beam shaping optic to the galvanometer optical scanner 106 is set such that the spot size of the beam of excitation light at the galvanometer optical scanner 106 is smaller than the size, $w_{galvo}$ (162), of the galvanometer mirrors of the galvanometer optical scanner 106. In certain embodiments, the size of the galvanometer mirrors of the galvanometer optical scanner can accept a beam of excitation light having a spot size from 3 to 5 mm in diameter.

In certain embodiments, the beam shaping optic is used to produce an appropriately shaped beam of excitation light (e.g., after its passage through the beam shaping optic) such that its spot size at all locations within the scan region is below a minimum desired spot size, even as the beam of excitation light is scanned through the scan region. As discussed above, in certain embodiments the minimum spot size within the scan region is determined by a scattering length of the media in which imaging is to be performed. Accordingly, in certain embodiments, for imaging in diffuse media such as tissue, the beam of excitation light is shaped to achieve a spot size of below 1 mm in diameter at all locations within the scan region. In certain embodiments, the beam of excitation light is shaped to achieve a spot size of approximately 0.5 mm at all locations within the scan region.

Where a beam shaping optic is used to produce a collimated or focused beam of excitation light, working distance is measured along an optical path from the beam shaping optic to the galvanometer optical scanner and from the galvanometer optical scanner to the object plane. As the beam of excitation light is scanned across the scan region, the working distance from the beam shaping optic to the object plane varies. Like FIG. 1A, FIG. 1B illustrates the minimal and maximal working distances for a one dimensional scan wherein the beam of excitation light is scanned across a first dimension of the scan region A minimal distance, $d_1$ (154), along a minimal length optical path from the galvanometer optical scanner 106 to the scan region 116 is determined by a maximum first optical scan angle, $\theta_{opt}$, produced by rotation of the first galvanometer mirror 108, and a desired scan size, 2X. Accordingly, a minimal working distance from the beam shaping optic to the scan region 116 is given by equation (6) below.

minimum working distance from beam shaping
optic=$d_0^{(2)}+d_1=d_0^{(2)}+X\tan(\theta_{opt})$ (6)

When the beam of excitation light is directed to a location at an edge of the scan region along a first dimension, the beam of excitation light travels a maximal distance, $d_2$ (156) along a maximal length optical path from the galvanometer optical scanner to the location at the edge of the scan region. Accordingly, the beam of excitation light travels a maximal working distance, given by equation (6) below, from the beam shaping optic 122 to the object plane 112.

maximum working distance from beam shaping
optic=$d_0^{(2)}+d_2=d_0^{(2)}+X\sin(\theta_{opt})$ (7)

Equations (6) and (7) above, which are based on a one-dimensional scan across the first dimension of the scan region can readily be extended to describe the minimum and maximum laser working distances for a two-dimensional scan. Equations (8) through (11) below are valid for a two-dimensional scan if both $d_1$ and $d_2$ are determined with respect to a two-dimensional scan, respectively. That is, such that $d_1$ is taken as a minimal distance measured along a minimal length optical path from the galvanometer optical scanner to a location within the two dimensional scan region, and $d_2$ is a maximal distance along a maximal length optical path from the galvanometer optical scanner to a location within the two dimensional scan region. In particular, as discussed above, in certain embodiments, for a two-dimensional scan region the minimal length optical path along which $d_1$ is measured is an optical path from the galvanometer optical scanner to a central location of the two-dimensional scan region. In certain embodiments, for a two-dimensional scan region, the maximal length optical path along which $d_2$ is measured is an optical path from the galvanometer optical scanner to a corner of the two dimensional scan region. In certain embodiments, for a two dimensional scan, X is taken as a distance along a diagonal from the center of the scan region to a corner of the scan region. The distance, $d_0^{(1)}$, along the optical path from the output 104 of the excitation source 102 to the galvanometer optical scanner 106 is independent of whether the scan is along a single direction or within a two-dimensional scan region.

In certain embodiments, beam shaping optics are used to produce an appropriately shaped beam of excitation light in order to maintain spot sizes at all locations within the scan region. A collimating optic can be used to produce a collimated beam of excitation light and a focusing optic can be used to produce a focused beam of excitation light. As discussed above, both collimated and focused beams vary in size as they propagate through the optical system, and the variation in size can be described by parameters such as a divergence angle, a beam waist location, and a beam waist diameter, $w_{bw}$.

Collimated Beams

In certain embodiments, the beam shaping optic is a collimating optic that collimates the beam of excitation light, thereby producing a collimated beam of excitation light. Ideally, a collimated beam of excitation light maintains a substantially fixed size as it propagates, while, in practice, the collimated beam diverges slowly as it propagates away from the collimating optic. Accordingly, the beam waist of the collimated beam of is located at the collimating optic 122, and the size of the collimated beam expands as it propagates towards the galvanometer optical scanner, and then towards the object plane. In certain embodiments, equation (8) below specifies an upper bound on a half angle divergence, φ, of the collimated beam of excitation light produced by the collimating optic in order for the spot size of the beam of excitation light to be less than a maximal desired spot size at all locations within the scan region. FIG. 8C and FIG. 8D, described above with respect to equation (3), similarly illustrates the basis of equation (8) below, with $d_0^{(1)}$ replaced with $d_0^{(2)}$.

$$\tan(\varphi) < \frac{w_{max} - w_{bw}}{2(d_0^{(2)} + d_2)}, \text{ (linear units in mm)} \quad (8)$$

In certain embodiments, parameter such as a focal length (e.g., an effective focal) of the collimating optic, along with properties of the excitation source such as an output divergence and an output area of the excitation source determine initial beam diameters and a half-angle divergence of collimated beams produced by a given collimating optic. For a free space laser used as an excitation source 102, the output divergence corresponds to an intrinsic divergence of the free space laser (e.g., the intrinsic divergence corresponding to a half-angle divergence of the beam of excitation light immediately after it exits the free space laser from the laser aperture) and the output area is an area of the laser aperture. When the excitation source 102 is a fiber laser or a fiber coupled laser, both of which output excitation light from a distal end of an optical fiber, the output divergence corresponds to a numerical aperture, NA, of the distal end of the optical fiber and the output area is determined by a core diameter, a, of the distal end of the optical fiber.

Focused Beams

In certain embodiments, the beam shaping optic 122 is a focusing optic that produces a focused beam of excitation light. A focused beam converges as it propagates until it reaches its smallest size at its beam waist location, after which it diverges. In certain embodiments, the focusing optic is used to shape the focused beam such that it reaches its beam waist near the object plane, at a location given by equation (9) below.

$$\text{distance from focusing optic to the beam waist} = d_0^{(2)} + \frac{d_1 + d_2}{2} \qquad (9)$$

As with focused beams produced directly from the output 104 of the excitation source, this allows a smallest spot size of the focused beam to be reached near the object plane. Considerations regarding the half-angle divergence of a focused beam produced by a focusing optic are similar to those discussed above with regard to focused beams output directly by the excitation source. In particular, for a focused beam of excitation light that reaches its beam waist location at the location specified by equation (9) above, the focusing optic is used to produce a focused beam having a half-angle divergence, $\varphi$, less than an upper bound, such that equation (10) (which is the same as equation (5)) below is satisfied. FIG. 8A and FIG. 8B, described above with respect to equation (5) are also illustrative for equation (10) below.

$$\tan(\varphi) < \frac{w_{max} - w_{bw}}{d_2 - d_1}, \text{ (linear units in mm)} \qquad (10)$$

In certain embodiments, parameters of the focusing optic, along with properties of the excitation source such as an output divergence and an output area of the excitation source determine initial beam diameters and a half-angle divergence of focused beams produced by a given focusing optic.

B.iii Example Optical System Design with Beam Shaping Optics

Example design considerations for use of collimating optics and focusing optics are described below. The example illustrates initial beam diameter and beam divergence considerations for using a collimating optic and a focusing optic to shape a beam of excitation light output from an optical fiber of a fiber coupled laser.

Figure 9:
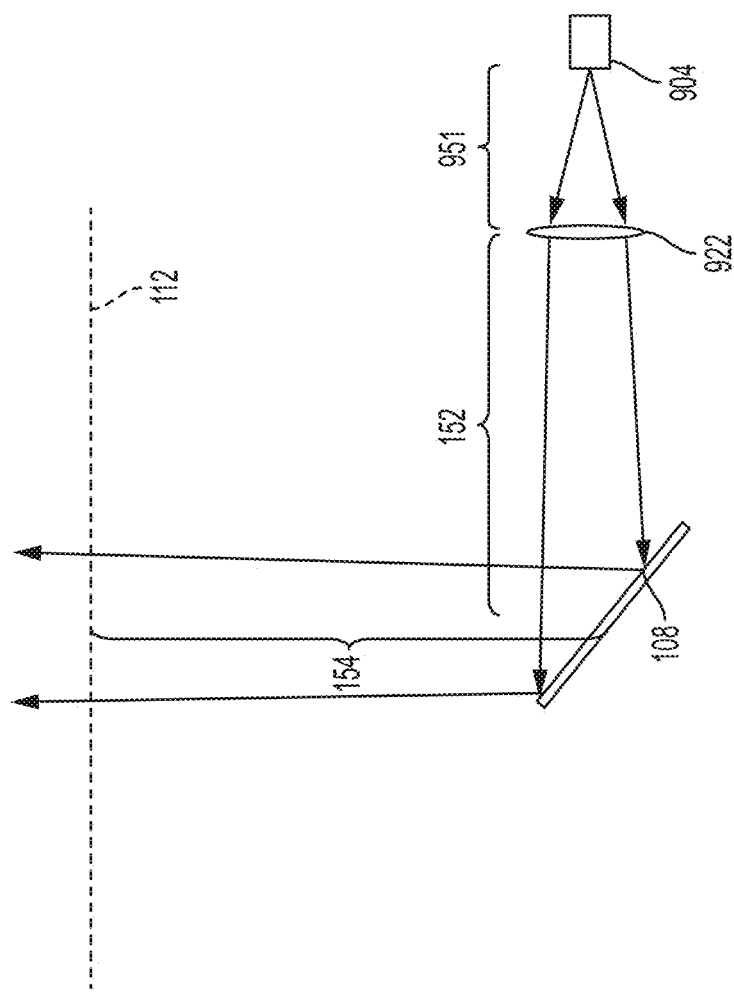
FIG. 9 is a schematic illustrating propagation of a collimated beam of excitation light, according to an illustrative embodiment.

As shown in FIG. 9, in a collimation approach, excitation light diverges as it exits the output 904 of the excitation source, and reaches an initial beam diameter at the collimating optic 922. In certain embodiments, in order to produce a collimated beam, the output of the excitation source (e.g., 904) is positioned at a focus of the collimating optic, such that a distance 951 from the output of the excitation source to the collimating optic 922 corresponds to an effective focal length (EFL) of the collimating optic. After passing through the collimating optic, it diverges at a slower rate as it travels from the collimating optic to the object plane, via reflection by one or more galvanometer mirrors of the galvanometer optical scanner. In FIG. 9 only a single galvanometer mirror is shown for clarity, and the collimated beam of excitation light propagates similarly when directed by two galvanometer mirrors.

Figure 10:
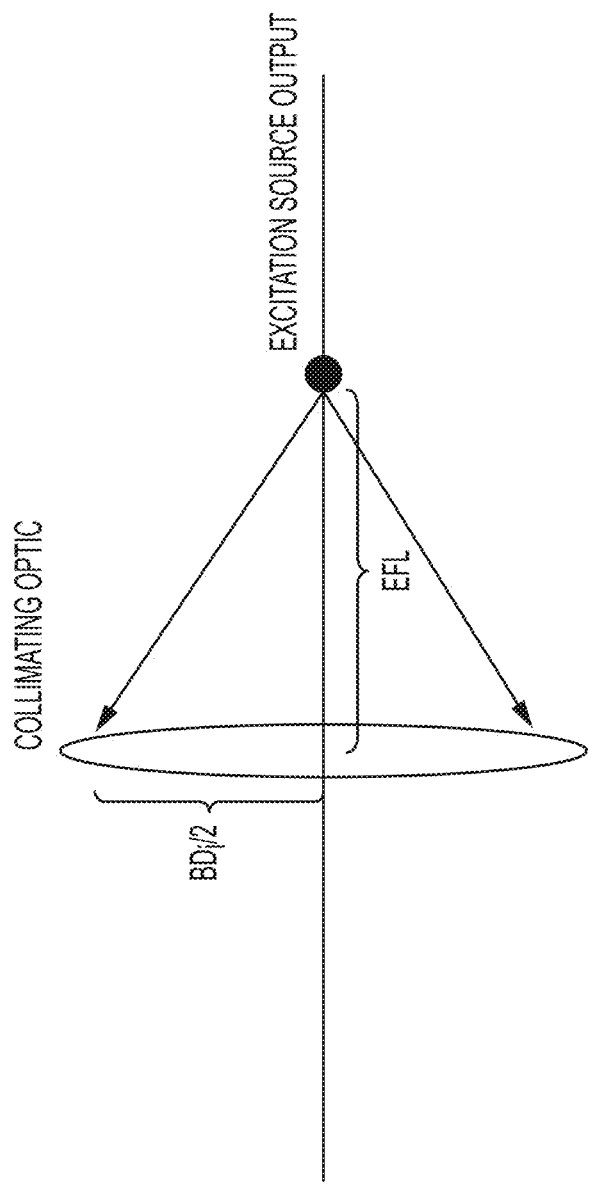
FIG. 10 is a schematic illustrating factors determining an initial diameter of a collimated beam of excitation light, according to an illustrative embodiment.

In certain embodiments, properties of the collimating optic, as well as the excitation source output determine the initial beam diameter and the divergence angle at which the collimated beam of excitation light propagates. For example, when a collimating optic is used to collimate a beam of excitation light output from a distal end an optical fiber of a fiber coupled laser or a fiber laser, the initial beam diameter, $BD_{initial}$, is determined by the EFL of the collimating optic and the numerical aperture, NA, of the optical fiber. The half-angle divergence of the collimated beam of excitation that is produced is determined by the EFL of the collimating optic and the diameter, a, of the core of the optical fiber at the distal end from which excitation light is emitted. The initial beam diameter, $BD_{initial}$, is determined via equation (11) below, as illustrated in FIG. 10, and the full-angle divergence is determined by equation (12) below (e.g., such that the half-angle divergence is half of the full angle divergence calculated via equation (12) below).

$$BD_{initial} = 2 \times EFL \times NA \qquad (11)$$

$$\varphi(mrad) = \frac{a(\mu m)}{EFL(mm)} \qquad (12)$$

In certain cases, the fiber core diameter and numerical aperture are sufficiently small and the EFL of the collimating optic is sufficiently large that the half-angle divergence and initial beam diameters determined via equations (11) and (12) above small enough that spot size requirements are met across the scan region. For example, for a fiber with a 5 μm diameter core and an NA of 0.12, a collimating optic with an EFL of 2 mm used for working distances of approximately 180 mm, a spot size of less than 1 mm across the scan region can be produced. In certain embodiments, for larger working distances, collimating optics are implemented to produce lower half-angle divergences. For example, for a for a fiber with a 5 μm diameter core and an NA of 0.1, a half-angle divergence of 1.25 mrad can be achieved using a 2 mm EFL collimating optic, appropriate for a maximal working distance of 200 mm.

In certain cases, properties of standard optical fibers that are used to output excitation light from fiber coupled sources are such that appropriately shaped collimated beams cannot be produced using standard fiber collimators as collimating optics. For example, a typical optical fiber NA is from 0.15 or 0.22 and standard focal lengths for fiber collimators range from 4 mm to 20 mm. A minimum beam diameter would be achieved with a short focal length fiber collimator and a small divergence optical fiber. The minimum values of NA=0.15 and EFL=4 mm result in an initial beam diameter of 1.2 mm as determined by equation (11) above. As discussed, for a collimated beam of excitation light, the beam waist is located at the collimating optic and the spot size increases as the collimated beam propagates (e.g., with increasing distance from the collimating optic).

Figure 11:
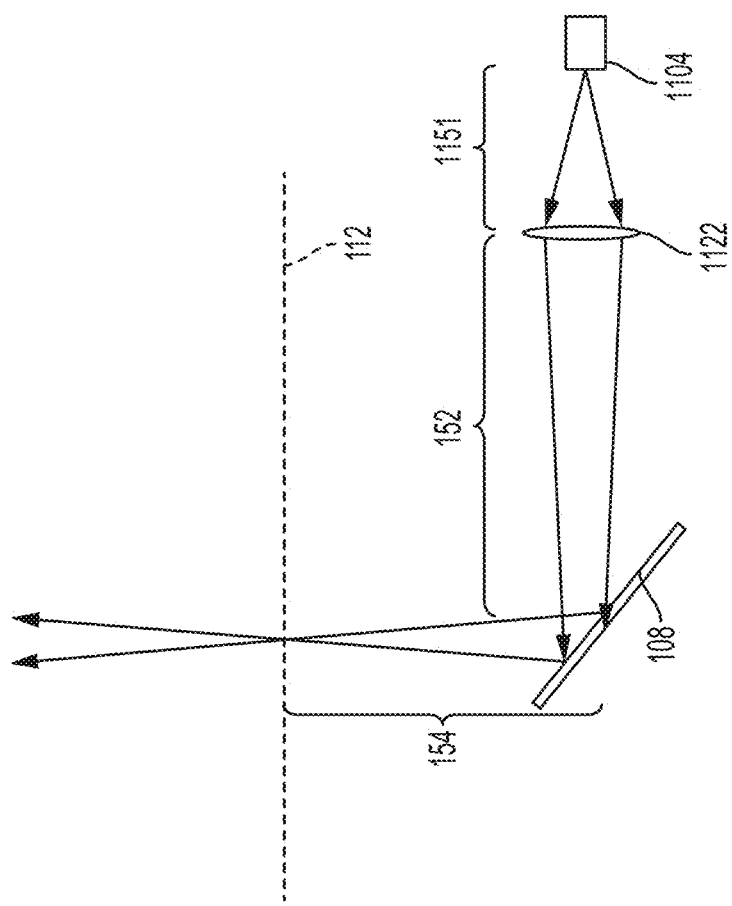
FIG. 11 is a schematic illustrating propagation of a focused beam of excitation light, according to an illustrative embodiment.

Accordingly, spot sizes at the object plane below 1 mm would not be achieved via such a configuration. In cases such as this, the approach described below, wherein a focusing optic is used to produce a gently focused beam of excitation light, allows use of excitation sources that have output properties that make collimation challenging. As shown in FIG. 11, in a focusing approach, excitation light diverges as it exits the output 1104 of the excitation source, and reaches an initial beam diameter at the focusing optic. After passing through the focusing optic 1122, it converges as it travels from the focusing optic to the beam waist location near the object plane, via reflection by one or more galvanometer mirrors of the galvanometer optical scanner. After passing through the beam waist location, the focused beam of excitation light diverges. As with FIG. 9, in FIG. 10 only a single galvanometer mirror is shown for clarity, and the collimated beam of excitation light propagates similarly when directed by two galvanometer mirrors In this example, a focusing optic provides advantages over the collimation approach in achieving small spot sizes over large working distances. In the example optical system, the optical layout parameters were as follows: $d_o^{(2)}$=100 mm, X=50 mm, $d_1$=200 mm, and $d_2$=206 mm.

Figure 12:
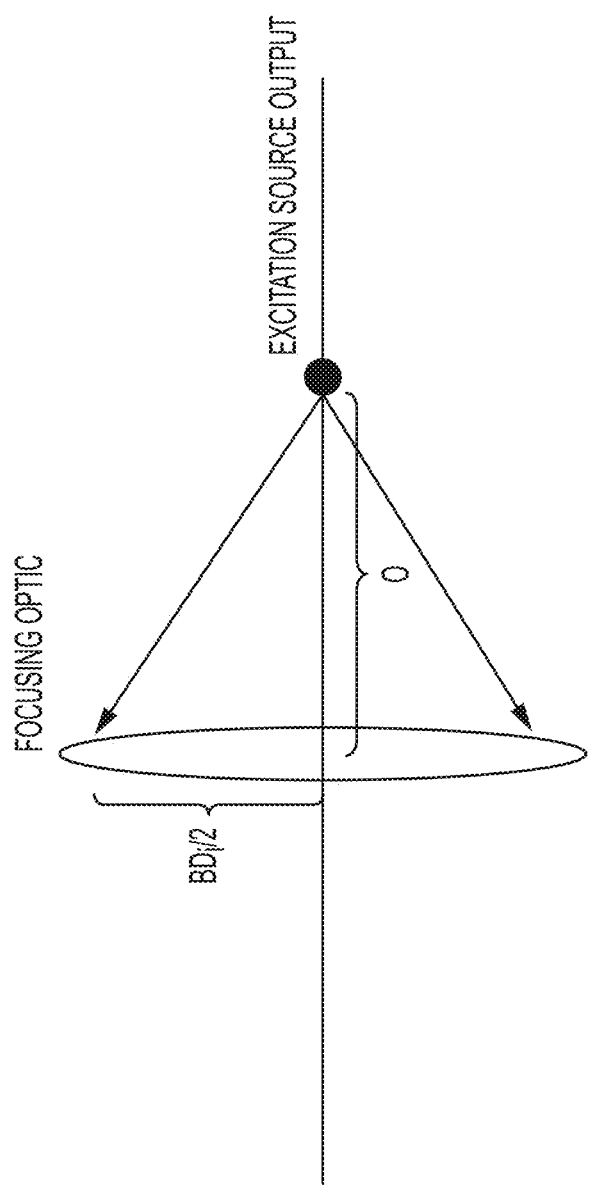
FIG. 12 is a schematic illustrating factors determining an initial diameter of a focused beam of excitation light, according to an illustrative embodiment.

Parameters relevant to a focusing optic include its effective focal length (EFL) and clear aperture (CA). The clear aperture defines the physical diameter of the area from which the focusing optic can collect light. In a focusing approach, a distance 1151 from the focusing optic 1122 to the output 104 of the excitation source is shifted from the focusing optic, and is referred to as an object distance, o (1151). The object distance, o (1151) can be determined based on a an initial beam diameter, $BD_i$, and parameters of the focusing optic, in a manner similar to that described above with respect to the collimating optic, as illustrated in FIG. 12. In the example optical system, a beam diameter of less than 3 mm was desired so that the beam could be coupled to the galvanometer optical scanner without overfilling the galvanometer mirrors. In certain embodiments, the clear aperture of the focusing optic must also be larger than the initial beam diameter.

$$o < \frac{BD_{initial}}{2NA} = \frac{3 \text{ mm}}{2 \times 0.15} = 10 \text{ mm} \quad (13)$$

In certain embodiments, an approximate range of from 10 to 15 mm for a required EFL of a focusing optic is determined using the object distance, o, and an approximate working distance of the system (e.g., approximately 200 mm). With a focusing optic lens, the beam of excitation light converges as it propagates towards the beam waist location. The optical system was aligned such that the beam waist location of the focused beam of excitation light produced by the focusing optic corresponded to the average working distance as described in equation (9). The average working distance given by equation (9) was 303 mm. The distance from the focusing optic to the output (e.g., the distal end of the optical fiber of the fiber coupled laser) of the fiber coupled laser, o, was calculated using the thin lens equation, shown in equation 9, where the image distance, i, was approximated as the working distance given by equation (9).

$$EFL = \left(\frac{1}{o} \mp \frac{1}{i}\right)^{-1} \quad (14)$$

Accordingly, for an object distance, o, of 10 mm, and an image distance, i, of 303 mm, a value for an EFL of 9.68 mm was found The spot size diameter at the beam waist was calculated based on the magnification of the focusing optic and the core diameter of the optical fiber of the fiber coupled laser. The magnification, M, was calculated as the ratio of average working distance to the distance from the output of the fiber laser to the focusing optic, o. Using the values above (e.g., an average working distance of 303 mm and a distance, o=10.34 mm, the magnification is approximately 30. The spot size diameter at the beam waist is calculated with Equation 10.

$$\text{Spot Diameter} = M \times \alpha \quad (15)$$

The magnification, M, along with the fiber core diameter, a, determines the spot size at the beam waist location. Single mode fibers have a standard fiber core diameter of approximately 8 μm while a multi-mode fiber can have a fiber core diameter ranging from 50 μm-200 μm at minimum. Accordingly, a single mode optical fiber used as the output of a fiber coupled source provides a spot size diameter at the beam waist location of approximately 0.24 mm, while a multi-mode fiber provides spot size diameter at the beam waist location of 1.5 mm at best (e.g., for a 50 μm core diameter).

Accordingly, with the long working distance of 300 mm and a small initial beam diameter (3 mm), the divergence requirements to maintain a <1 mm spot for all working distances is met.

B. iv Positioning of Optical Components Based on Excitation Beam Divergences

In certain embodiments, equations (16a), (16b) and (17) below reflect additional design considerations that relate positioning of various optical components to divergence properties of a beam of excitation light.

For example, equation (16a) below relates the distance from an output of an excitation source that produces a collimated beam of excitation light to a maximum viable working distance for the particular beam of collimated light. The maximal viable working distance is the distance from the beam waist at the output of the excitation source to a point at which the collimated beam of excitation light reaches the maximal desired spot size, $w_{max}$ (e.g., such that as the collimated beam of excitation light travels greater distances, the spot size of the beam exceeds $w_{max}$). In certain embodiments, the maximum viable working distance depends on an initial beam diameter, at the output of the excitation source, and the half-angle divergence of the beam of excitation light. In certain embodiments, a maximal optical path length, $d_2$, is dictated by a desired scan size and maximal rotational angles of the galvanometer mirrors of the galvanometer optical scanner. Accordingly, with the maximal viable working distance and $d_2$ fixed, equation (2) above becomes:

$$d_o^{(1)} < \text{maximum viable working distance} - d_2 \quad (16a)$$

Similarly, for a collimated beam of excitation light, equation (7) is used to determine equation (16b) below.

$$d_o^{(1)} < \text{maximum viable working distance} - d_2 \quad (16b)$$

Similar considerations can be used to determine (16b) possible values of $d_1$ for a focused beam configuration. In certain embodiments, a half-angle divergence of a focused beam, along with a spot size of the focused beam determine a depth of focus. The depth of focus refers to a distance in between the two locations on either side of the beam waist location at which a spot size of the beam waist reaches a value corresponding to the maximal desired spot size, $w_{max}$. In certain embodiments, if a difference between (i) the distance, $d_1$, the beam of excitation light travels along the minimal length optical path and (ii) the distance, $d_2$, that the beam of excitation light travels along the maximal length optical path is greater than the depth of focus, then a spot size of the beam of excitation light will exceed the desired maximal spot size at certain locations within the scan region. Accordingly, for a fixed desired scan size, equation (17) below provides guidance for positioning the galvanometer optical scanner a distance, $d_1$, from the object plane. In equation (17) below, the parameter X corresponds to a distance along a diagonal, measured from the center to a corner of a 2D scan region.

$$\sqrt{d_1^2 + X^2} - d_1 < \text{depth of focus} \quad (17)$$

C. Tomographic Imaging Via Beam Scanning

Figure 13:
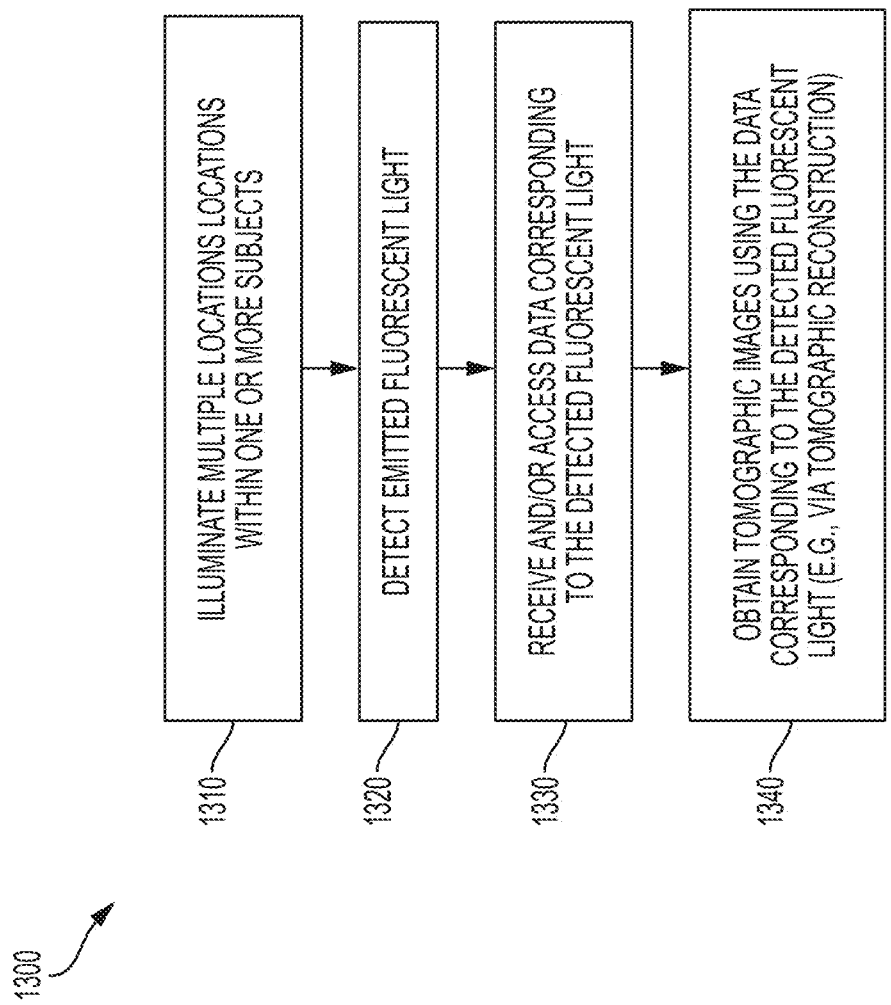
FIG. 13 is a block flow diagram of a process for obtaining a tomographic image of one or more objects via rapid scanning of a beam of excitation light, according to an illustrative embodiment.

In certain embodiments, by allowing a beam of excitation light to be scanned through a plurality of locations within a scan region while maintaining small spot sizes, the approaches described above provide for rapid tomographic imaging over a wide field of view. FIG. 13 shows an example process 1300 for imaging one or more subjects positioned across the object plane using the beam scanning approaches described herein. In certain embodiments, in a first step 1310, a beam of excitation light is scanned across the scan region 116 as described above with regard to FIG. 1A and FIG. 1B. The beam of excitation light may be appropriately shaped using any of the beam shaping approaches described in the previous sections in order to maintain a desired spot size across the scan region 116.

As the beam of excitation light is directed to a particular excitation location within the scan region, it illuminates a given subject positioned in the path of the beam of excitation light at a corresponding illumination location on the surface of the subject. As discussed previously, light incident on the surface of the subject diffuses within the subject, and excites fluorescent species within the subject, causing emission of fluorescent light.

In certain embodiments, as the beam of excitation light is directed from excitation location to excitation location across the scan region, one or more detectors detect fluorescent light emitted from within a given subject, as a result of excitation of fluorescent species within the subject (1320). The one or more detectors may be aligned in an epi-illumination geometry or in a transillumination geometry.

FIG. 1A and FIG. 1B illustrate an example of the transillumination geometry, showing a detector 120 positioned at an opposite side of the object plane from the scanning optical galvanometer. Fluorescent light is typically emitted in all directions, and the portion of the emitted fluorescent light 118a, 118b, 118c from each of three subjects 114a, 114b, 114c that is detected by the detector is illustrated.

In certain embodiments, the one or more detectors detect fluorescent light as the one or more subjects are illuminated. In certain embodiments, a focal plane array (FPA) comprising a plurality of pixels that is aligned to image the entire scan region is used. Examples of FPA detectors include CCD cameras, CMOS cameras, and other detectors comprising a plurality of pixels. Fluorescent light incident on FPA detectors is detected by the plurality of pixels, such that a fluorescence emission image that represents the intensity distribution of the fluorescent light incident across the detector area can be recorded. In certain embodiments, a bundle of fibers can be arranged to function similar to a FPA detector, and used to record a 2D emission image. Fibers of the bundle can be aligned such that their proximal (input) ends collect emitted fluorescent light at a plurality of locations. Each fiber can be aligned (e.g., attached) at is opposite, distal, end to a corresponding single element detector, which detects light that is collected by the fiber proximal end and guided along the length of the fiber to illuminate the active area of the detector. In this manner, each fiber of the bundle functions similarly to a pixel of an FPA detector, and the bundle, along with the multiple single element detectors, used to record a emission image.

In certain embodiments, as the beam of excitation light is scanned, a plurality of fluorescence emission images are recorded by the one or more detectors (e.g., using an FPA; e.g., using multiple detectors of a fiber bundle).

In certain embodiments, a fluorescence emission image is recorded for each discrete excitation location. Each fluorescence emission image recorded in this manner thus is associated with a distinct excitation location and represents fluorescent light emitted in response to illuminating one or the one or more subjects by directing the beam of excitation light to the associated excitation location.

In certain embodiments, data corresponding to the detected fluorescent light is received and/or accessed (1330) by a processor of a computing device and used to obtain (e.g., compute) one or more tomographic images of the one or more subjects (1340). For example, tomographic images may be computed (e.g., via tomographic reconstruction techniques) using the fluorescence emission images recorded for each of the discrete excitation locations. In particular, in certain embodiments, a tomographic image for each of one or more subjects positioned across the scan region can be obtained.

For example, wherein multiple subjects are imaged, each subject can be associated with a portion of the fluorescence emission images. In particular, when multiple subjects are positioned across the scan region, each subject can be associated with a different portion of the excitation locations within the scan region. For example, if three subjects are imaged, a first subject is positioned such that it is illuminated when the beam of excitation light is directed to each of a first portion of the plurality of excitation locations. Accordingly, the first subject is associated with the first portion of excitation locations. The second subject is similarly associated with a second portion of the excitation locations, and the third subject similarly associated with a third portion of the excitation locations.

Accordingly, for a given subject, the fluorescence emission images that are recorded for excitation locations associated with the subject can be identified, and used as input to tomographic reconstruction techniques in order to obtain a tomographic image of the given subject. This process can be repeated for each subject positioned across the scan region.

In certain embodiments, tomographic imaging is performed by detecting, in addition to fluorescent light, excitation light that is either transmitted through (e.g., as in a transillumination geometry) or reflected from (e.g., as in an epi-illumination geometry) the one or more subjects. Data corresponding to the detected excitation light can be used, along with the data corresponding to the detected fluorescent light, in tomographic reconstruction approaches to obtain tomographic images of the one or more subjects.

For example, as the beam of excitation light is scanned across the scan region, a plurality of excitation images representing detected excitation light transmitted through or reflected by the one or more subjects can be recorded by the one or more detectors, in a manner similar to that used to record fluorescence emission images. In particular, as the beam of excitation light is directed to a particular excitation location within the scan region, it illuminates a given subject positioned in the path of the beam of excitation light at a corresponding illumination location on the surface of the subject. A portion of the excitation light may be transmitted through the subject, and a portion of the excitation light may be reflected. In certain embodiments, as the beam of excitation light is directed from excitation location to excitation location across the scan region, the one or more detectors detect excitation light transmitted through or reflected by the one or more subjects. The one or more detectors may be aligned in an epi-illumination geometry, so as to detect reflected excitation light, or in a transillumination geometry, so as to detect transmitted excitation light.

In certain embodiments, similar to detected fluorescence emission images, excitation images can be detected by focal plane array detectors (e.g., CCD cameras, CMOS cameras, and the like) or using multiple detectors of a fiber bundle as described above. In certain embodiments, as with fluorescence emission images, an excitation image can be recorded for each of a plurality of discrete excitation locations within the scan region. The recorded excitation images can be used in combination with the recorded fluorescence images to obtain tomographic images of the one or more subjects.

In certain embodiments, in order to detect fluorescent light, a fluorescence optical filter is placed in front of the one or more detectors. The fluorescence optical filter is substantially transparent to light having a wavelength corresponding to that of the emitted fluorescent light and substantially opaque to light at other wavelengths, including the wavelength of the excitation light. The fluorescence optical filter thus selectively passes emitted fluorescent light, allowing it to be detected by the one or more detectors, and blocks excitation light, allowing for selective detection of fluorescent light. In certain embodiments, in order to detect excitation light, the fluorescence optical filter is removed. This approach may be appropriate if the strength (e.g., intensity) of the transmitted or reflected excitation light to be detected is substantially larger than that of the emitted fluorescent light. In certain embodiments, excitation light is detected by placing a second optical filter—an excitation optical filter—in front of the one or more filters, wherein the excitation optical filter is substantially transparent to light having a wavelength of the excitation light, and substantially opaque to light having a wavelength of the emitted fluorescent light.

In certain embodiments, two scans are performed to detect both fluorescent light and excitation light. In a first scan, the fluorescence optical filter is placed in front of the one or more detectors and fluorescent light (e.g., a fluorescence emission image) is detected for each of the excitation locations within the scan region. In a second scan the fluorescence optical filter is removed, or an excitation optical filter that selectively passes excitation light is placed in front of the one or more detectors and excitation light (e.g., an excitation image) is detected for each of the excitation locations within the scan region. In certain embodiments, a single scan is performed and, for each excitation location within the scan region fluorescent light is detected with the fluorescence optical filter in place, after which excitation light is detected with either the fluorescence optical filter removed, or substituted with an excitation optical filter.

In certain embodiments, by virtue of the ability to rapidly scan the beam of excitation light using the beam scanning approach described herein, a multiplexed approach can be used, wherein each fluorescence emission image is associated with multiple excitation locations. In this approach, the discrete excitation locations are arranged in sets, with each set comprising multiple excitation locations. Rather than raster scan the beam of excitation light from excitation location to excitation location in a sequential fashion (e.g., directing the beam of excitation light to a first excitation location, then an adjacent excitation location, and so on), the beam of excitation light is scanned in a set-wise fashion. The galvanometer optical scanner scans the beam of excitation light through the discrete excitation locations one set at a time, directing the beam of excitation light to each discrete excitation location within a given set before proceeding on to a next set.

In certain embodiments, the fast scanning capability of the galvanometer optical scanner allows the beam of excitation light to be directed to each of the discrete excitation locations of a set, one after the other, during a time period corresponding to an exposure window of the one or more detectors. Each fluorescence emission image represents fluorescent light detected by the one or more detector, over a period of time corresponding to the exposure window. By scanning the beam of excitation light to multiple excitation locations during the exposure window of the one or more detectors, a fluorescence image associated with the set of excitation locations is recorded. Each fluorescence emission recorded in this manner is thus associated with a set of excitation locations and represents detected fluorescent light emitted in response to illuminating one or the one or more subjects by directing the beam of excitation light to each excitation location of the associated set.

In certain embodiments, this approach can be used reduce the amount of time and number of fluorescence emission images needed to obtain tomographic images of multiple subjects. As discussed above, each subject is associated with a portion of the excitation locations within the scan region.

The sets of excitation locations can be arranged such that each set comprises an excitation location associated with each subject. During a given exposure window used to record a fluorescence emission image, the beam of excitation light illuminates the first subject (e.g., during a first third of the exposure window), then the second subject (e.g., during a second third of the exposure window), and the third subject (e.g., during a final third of the exposure window). Multiple fluorescence emission images may be recorded in this manner, each corresponding to a different set. Accordingly, each fluorescence emission image is a multi-subject emission image representing fluorescent light emitted from within each of the different subjects. Accordingly, the number of fluorescence emission images recorded can be reduced by a multiple corresponding to the number of subjects imaged.

In certain embodiments, the spatial separation between the multiple subjects is used to determine, for each subject, a portion of each multi-subject fluorescence emission image that is associated with the subject (e.g., the portion that represents fluorescent light emitted as a result of illuminating the subject by directing the beam of excitation light to an excitation location associated with the subject). For example, in certain embodiments, a co-registered bright field image is used to identify a spatial region of the fluorescence emission image corresponding to the subject. In this manner, a plurality of single subject fluorescence emission images associated with the subject can be determined. For each subject, the determined single subject fluorescence emission images associated with the subject can be used as input to tomographic reconstruction techniques in order to obtain a tomographic image of the subject.

In certain embodiments, the multiplexed scanning approach described above can also be used for detection of excitation light, and data corresponding to the detected excitation light is also used, in combination with the data corresponding to the detected fluorescent light to obtain tomographic images of the one or more subjects.

D. Multi-Laser Wide Field Trans-Illumination Schemes

In certain embodiments, systems and methods described herein provide for use of multiple excitation sources to perform tomographic imaging using multiple beams of excitation light. Opto-mechanical alignment is used to direct multiple beams of excitation light to a galvanometer optical scanner to scan the beams of excitation light as described above. For each excitation source, any one of the beam shaping approaches described above can be used to provide a corresponding beam of excitation light that is appropriately shaped so as to maintain a desired spot size at all locations within the scan region.

Figure 2:
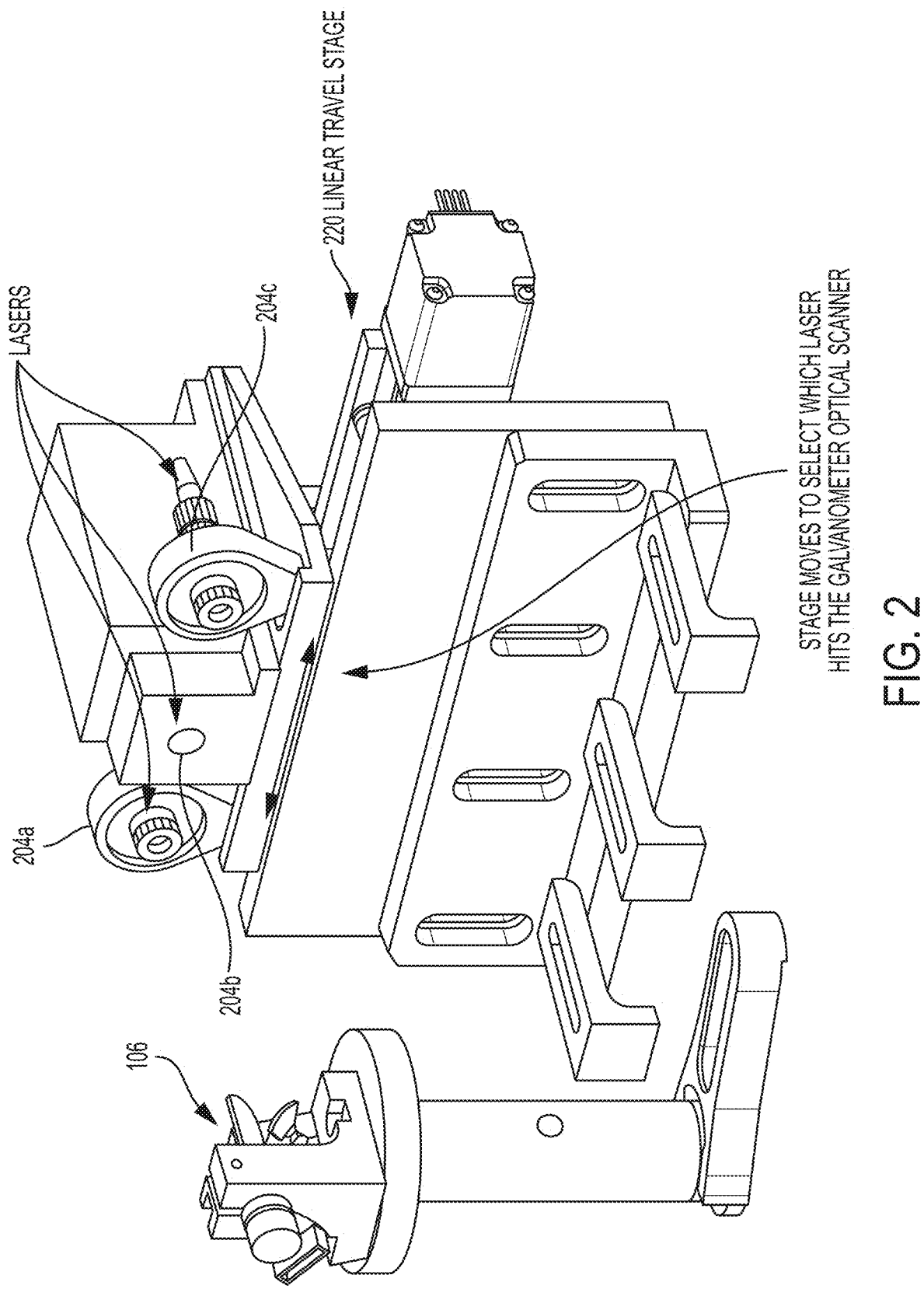
FIG. 2 is a schematic showing an system wherein multiple excitation sources are separately aligned to a galvanometer optical scanner via a linear stage, according to an illustrative embodiment.

In certain embodiments, multiple excitation sources are aligned to direct their respective beams of excitation light from their output to the galvanometer optical scanner one at a time using motorized stages. FIG. 2 shows an example of a system wherein the outputs of three excitation sources (e.g., lasers) 204a, 204b, and 204c are mounted side by side on a linear translation stage 220. Two of the excitation sources are fiber coupled lasers. The output of each of the fiber coupled lasers (204a and 204c), which is a distal end of an optical fiber coupled to the laser, are shown mounted on the linear translation stage. A free space laser, for which the output 204b is a laser aperture of the laser, is also shown mounted on the linear translation stage.

The linear translation stage can be moved to align the output of a given excitation source to direct a beam of excitation light from the output of the given source to the galvanometer optical scanner, such that it can be scanned across a scan region of the object plane as described above with respect to FIG. 1A. This approach allows the full angular capability of the galvanometer mirrors of the galvanometer optical scanner to be utilized by each excitation source.

In certain embodiments, the systems and methods described herein utilize a static design, wherein multiple excitation sources are simultaneously mounted in fixed positions and aligned to direct their respective beams of excitation light to the galvanometer optical scanner. The static design approach avoids the need for motorized stages, which can be slow, add complexity, and introduces risk of misalignment through vibrations, etc.

FIG. 3A is a schematic illustrating simultaneous alignment of three excitation sources (e.g., lasers) 102a, 102b, and 102c to a galvanometer optical scanner 106. A first excitation source 102a is aligned to direct a its beam of excitation light along a first optical path 305a from its output to the galvanometer optical scanner. Each of the other excitation sources 102b and 102c are aligned to direct their respective beam of excitation light along an optical path from their output to the galvanometer optical scanner 106 at a corresponding offset angle with respect to the first optical path 305a. Excitation source 102b directs the beam of excitation light emitted from its output to the galvanometer optical scanner 106 along optical path 305b, offset to the first optical path 305a at offset angle $\theta_2$. Excitation source 102c directs the beam of excitation light emitted from its output to the galvanometer optical scanner 106 along optical path 305c, offset to the first optical path at offset angle $\theta_3$.

The galvanometer optical scanner directs, via reflection by one or more galvanometer mirrors that it comprises, each of the beams of excitation light towards the object plane. Each beam of excitation light from a respective excitation source can thus be scanned across a respective scan region of the object plane via rotation of the galvanometer mirrors of the galvanometer optical scanner 106. Due to the offset angles at which each excitation source directs its respective beam of excitation light to the galvanometer optical scanner 106, the optical scan angles at which the galvanometer optical scanner directs the beams of excitation light towards the object plane 112 are offset from each other. In particular, as shown in FIG. 3A, for a given rotational angle of a first galvanometer mirror 108 of the galvanometer optical scanner 106, each of the three beams of excitation light is directed to the object plane at a distinct optical scan angle. In certain embodiments, for a given beam of excitation light, the optical scan angle at which it is directed to the object plane is determined by the offset angle at which it is directed from the output of its corresponding excitation source to the galvanometer optical scanner. As a result, for a given rotational angle of the one or more galvanometer mirrors of the galvanometer optical scanner, the beams of excitation light from the three excitation sources are directed towards the object plane along distinct optical paths.

For example, as shown in FIG. 3A, at a given rotational angle of the first galvanometer mirror 108, the first beam of excitation light from the first excitation source 102a is directed along a first optical path 310a from the galvanometer optical scanner 106 to the object plane 112. The beam of excitation light from the second excitation source 102b is directed to the object plane along a second optical path 310b that is offset from the from the first optical path from the galvanometer optical scanner to the object plane at offset angle $\theta_2$, which corresponds to the angle at which optical path 305b is offset from optical path 305a. Similarly, the beam of excitation light from the third excitation source 102c is directed to the object plane along a third optical path 310c that is offset from the from the first optical path from the galvanometer optical scanner to the object plane at offset angle $\theta_3$, which corresponds to the angle at which optical path 305c is offset from optical path 305a.

Accordingly, as the first galvanometer mirror 108 is rotated, each beam of excitation light is scanned across a distinct scan region that is shifted along the direction associated with the first galvanometer mirror 108 (e.g., the first direction) with respect to the scan regions of the other beams of excitation light from the other excitation sources. For example, as shown in FIG. 3A, the first beam of excitation light from the first excitation source is scanned across a first scan region 116a. The second beam of excitation light from the second excitation source is scanned across a second scan region 116b, which is shifted in along the first dimension, in a positive direction, with respect to the first scan region 116a. Similarly, the third beam of excitation light from the third excitation source is scanned across a third scan region 116c, also shifted with respect to the first scan region 116b along the first dimension. In FIG. 3A, the scan regions 116a, 116b, 116c are offset from each other in a direction perpendicular to the object plane (e.g., vertically with respect to the page) for clarity—each scan region actually lies on the object plane 112. A portion of the three scan regions overlap. This region of overlap corresponds to a shared scan region, across which each of the three beams of excitation light is scanned. Accordingly, one or more subjects positioned across the shared scan region can be illuminated by beams of excitation light from each of the three excitation sources.

Figure 3B:
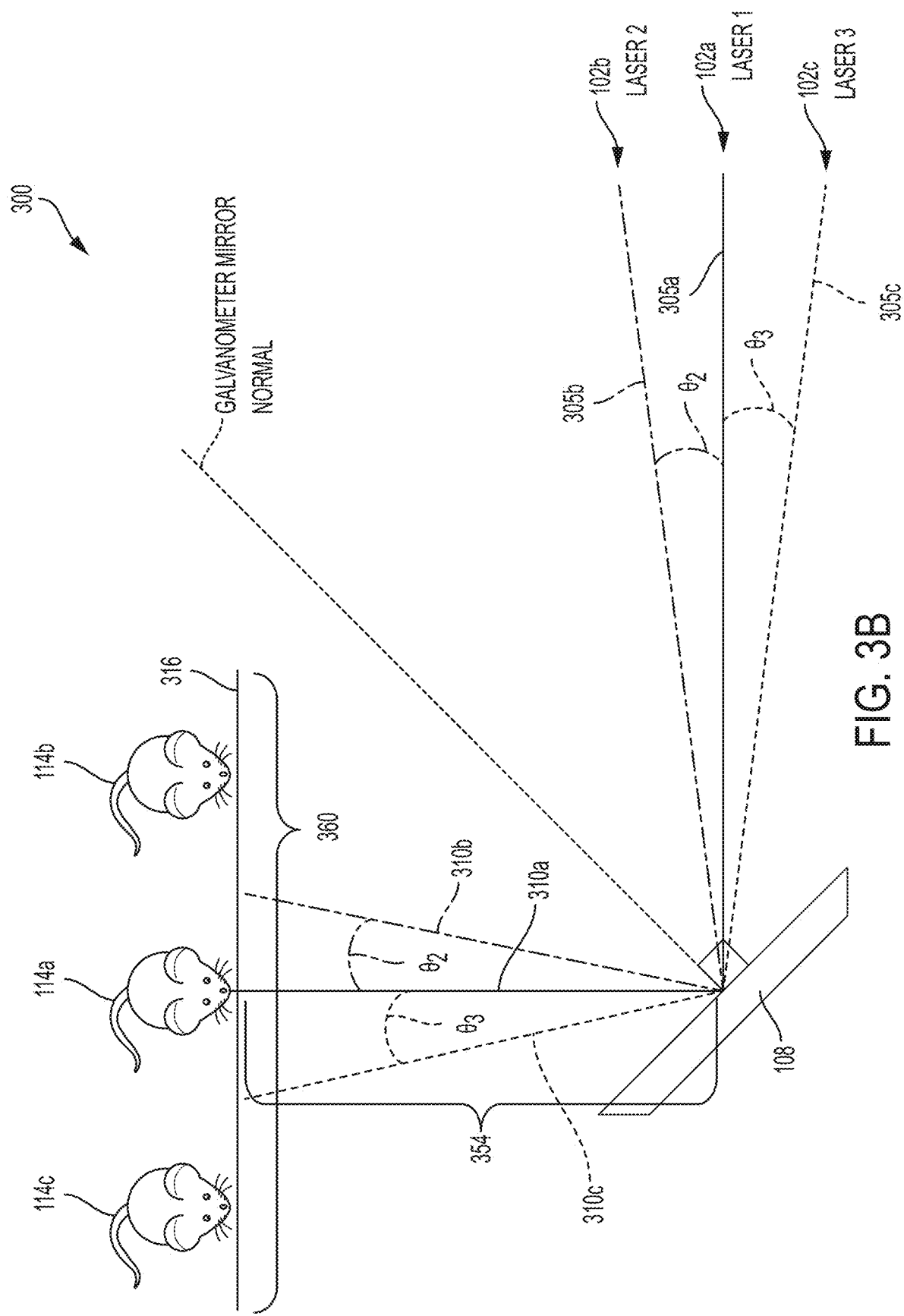
FIG. 3B is a schematic illustrating reflection of three beams of excitation light from three different lasers by a galvanometer mirror of a galvanometer optical scanner, according to an illustrative embodiment.

Turning to FIG. 3B, a size of the shared scan region along a particular dimension of the scan region can be determined as follows. FIG. 3B illustrates reflection of the three beams of excitation light by a first galvanometer mirror 108 in a single plane, such that as the first galvanometer mirror 108 is rotated, they are scanned across a first dimension of each of their respective scan regions. For a first beam of excitation light that is directed "on-axis" to the galvanometer scanner, the size of the corresponding first scan region along the first dimension, $L_a$, is given by equation (18) below, wherein $\theta_{opt}$ is the maximum first optical scan angle associated with the first galvanometer mirror. The maximum and minimum shared scan angles in the positive and negative directions, respectively, are given by equations (19) and (20), respectively.

$$L_a = 2d_1 \tan(\theta_{opt}) \quad (18)$$

$$\theta_{max} = \theta_{opt} - \theta_3 \quad (19)$$

$$\theta_{min} = \theta_{opt} - \theta_2 \quad (20)$$

If the offset angles at which the beams of excitation light from the second and third excitation sources are directed to the galvanometer optical scanner are the same, $\theta_2 = \theta_3$, and the shared scan size along the first dimension, $L_{shared}$, is given by equation (21) below.

$$L_{shared} = 2d_1 \tan(\theta_{opt} - \theta_2) \quad (21)$$

When two galvanometer mirrors are used to scan the beams of excitation light across two-dimensional scan regions, a similar approach can be used to determine a shared scan size (e.g., $L^{(2)}_{shared}$) along a second dimension, associated with a second galvanometer mirror. In certain embodiments, the galvanometer optical scanner is placed a specific distance 354 along a minimal length optical path from the galvanometer optical scanner to a location within the shared scan region (e.g., a central location of the shared scan region) to produce a shared scan region of a desired size. Similar considerations to those discussed above with regard to the optical layout for a single excitation source can be used, along with equations (18) to (21) to determine a size of the shared scan region.

Figure 4:
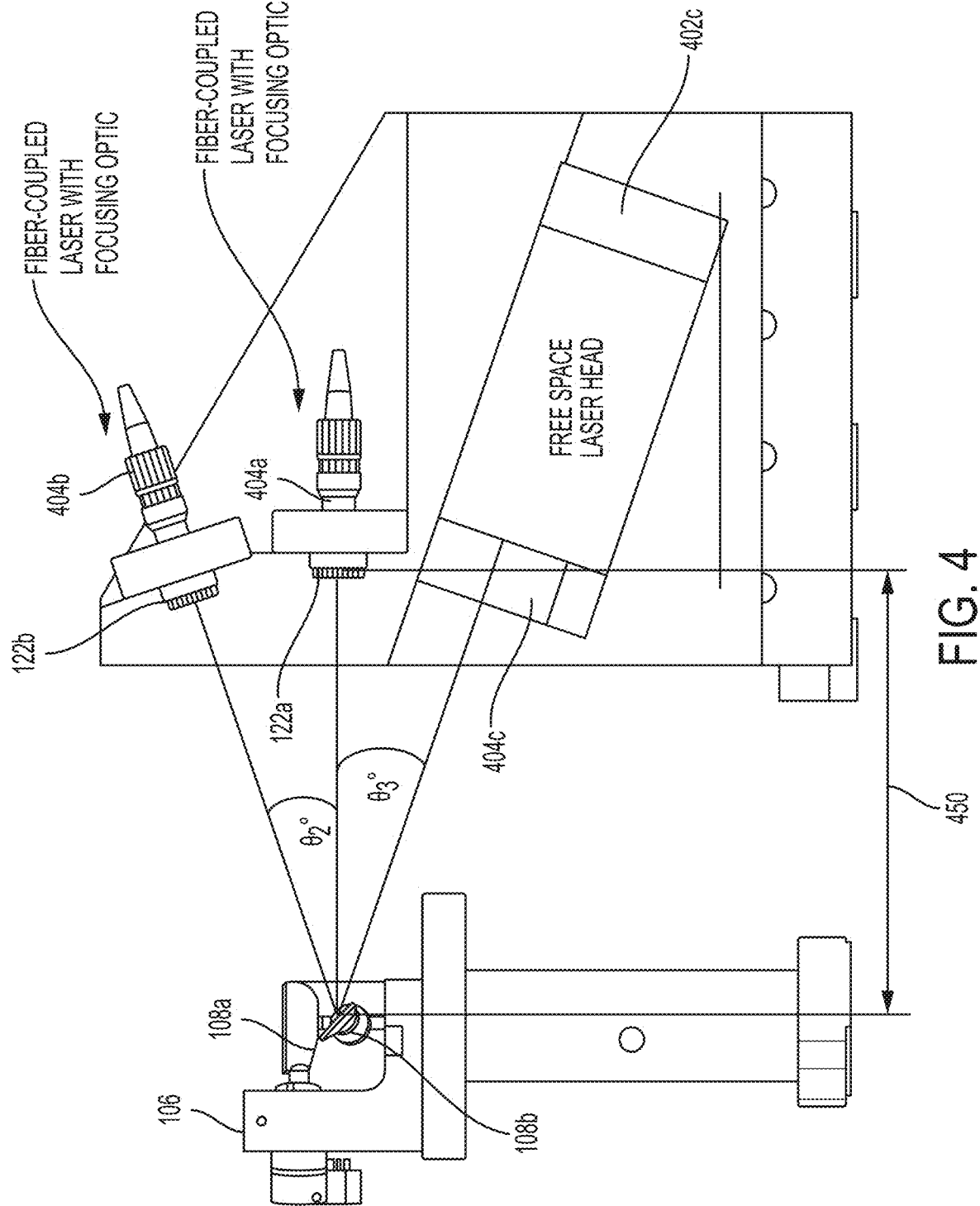
FIG. 4 is a schematic showing a system wherein three lasers are simultaneously aligned to a galvanometer optical scanner comprising two rotating galvanometer mirrors, according to an illustrative embodiment.

FIG. 4 shows a system wherein the outputs 404a, 404b, and 404c of three lasers are offset along a single direction (e.g., a vertical direction; e.g., in a direction along a y-axis) such that the offset angles associated with the second and third excitation sources lie in a single plane.

In certain embodiments, excitation sources may be offset from each other in multiple directions, along multiple axes. For example, in the system shown in FIG. 4 additional excitation sources could be accommodated by positioning their outputs at offsets along an axis perpendicular to the page (e.g., along a z-axis). Aligning multiple outputs of multiple excitation sources such that they are offset from each other along multiple directions and multiple axes in this manner provides a larger area for mounting outputs of the excitations sources and allows more sources to be coupled to the galvanometer optical scanner.

In certain embodiments, each beam of excitation light from each excitation source may be shaped via any one of the beam shaping approaches described above. For example, two of the outputs, 404a and 404b, are distal ends of fibers of fiber coupled lasers. Each fiber coupled laser has a focusing optic 122a and 122b positioned in the respective optical path from its output to the galvanometer optical scanner 106. A third excitation source 402c is a free space laser. No beam shaping optic is positioned in the optical path from the output 404c of the free space laser to the galvanometer optical scanner 106. The free space laser may be engineered to output a focused or collimated beam of excitation light, in accordance with the beam shaping approaches described above, to obtain a desired spot size at all locations within its respective scan region.

The galvanometer optical scanner 106 shown in FIG. 4 comprises two mirrors 108a and 108b for scanning the beams of excitation light from each of the excitation sources along orthogonal directions across the object plane.

In certain embodiments, a minimal distance from either a beam shaping optic or the output of an excitation source 450 is determined based on a spatial separation between the excitation source outputs and offset angles in order to accommodate the multiple beams of excitation light from the excitation sources. In certain embodiments, the minimal distance 450 is greater than the product of (i) the minimum laser separation and (ii) the cotangent of one of the excitation source offset angles (e.g., the smallest absolute value offset angle).

In certain embodiments, tomographic imaging using multiple beams of excitation light is performed in a fashion similar to that described above with respect to FIG. 13 for a single beam of excitation light. In particular, process 1300 described above may be performed for each excitation source, such that a set of multiple tomographic images, each corresponding to a different excitation source, is obtained. As shown in FIG. 3A, a transillumination geometry similar to that described above with respect to FIG. 1A and FIG. 1B may be used for tomographic imaging with multiple excitation sources.

In certain embodiments, the ability to obtain multiple tomographic images using multiple excitation sources allows for multi-spectral imaging. In certain embodiments, multi-spectral imaging involves illuminating one or more objects with a plurality of beams of excitation light, having a distinct wavelength. Accordingly, the each multiple excitation sources that can be aligned as described above can each be used to provide a beam of excitation light having a distinct excitation wavelength. In certain embodiments, each distinct excitation wavelength is used to excite a different fluorescent species. For example, multiple excitation wavelengths within the spectral range from 400 nm to 1300 nm can be used to excite a multiple different fluorescent species. In certain embodiments, each beam of excitation light from each excitation source thus excites, and causes fluorescent emission from a distinct fluorescent species within the one or more subjects. Accordingly, by successively performing tomographic imaging at each excitation wavelength, tomographic images representing the distribution of each of a plurality of fluorescent species within the one or more subjects can be obtained.

E. Setup Validation and Experimental Results

Figure 5:
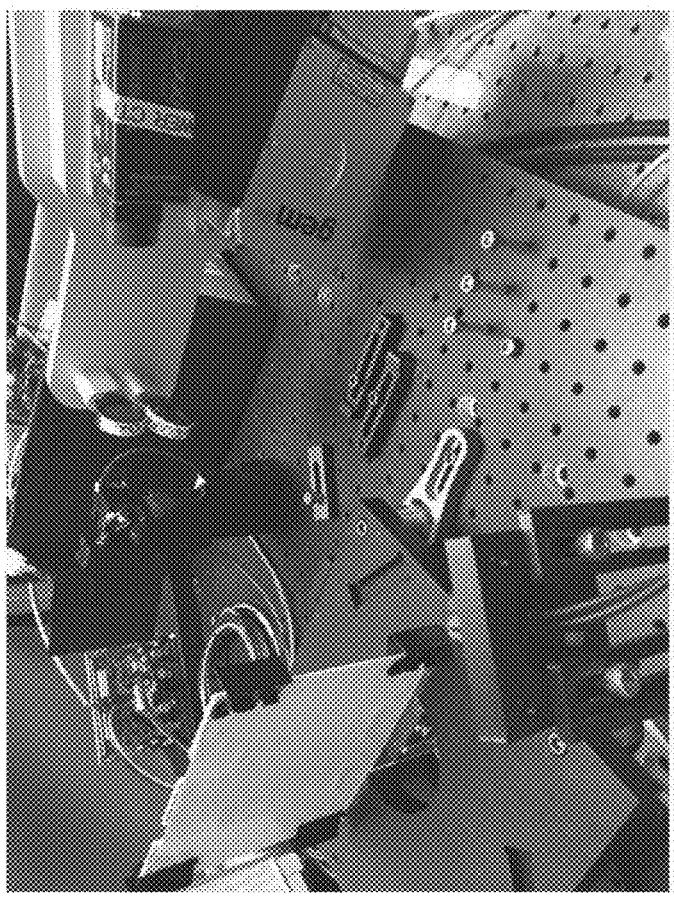
FIG. 5 is a set of two photographs of a wide field of view transillumination excitation system, according to an illustrative embodiment.
Figure 5:
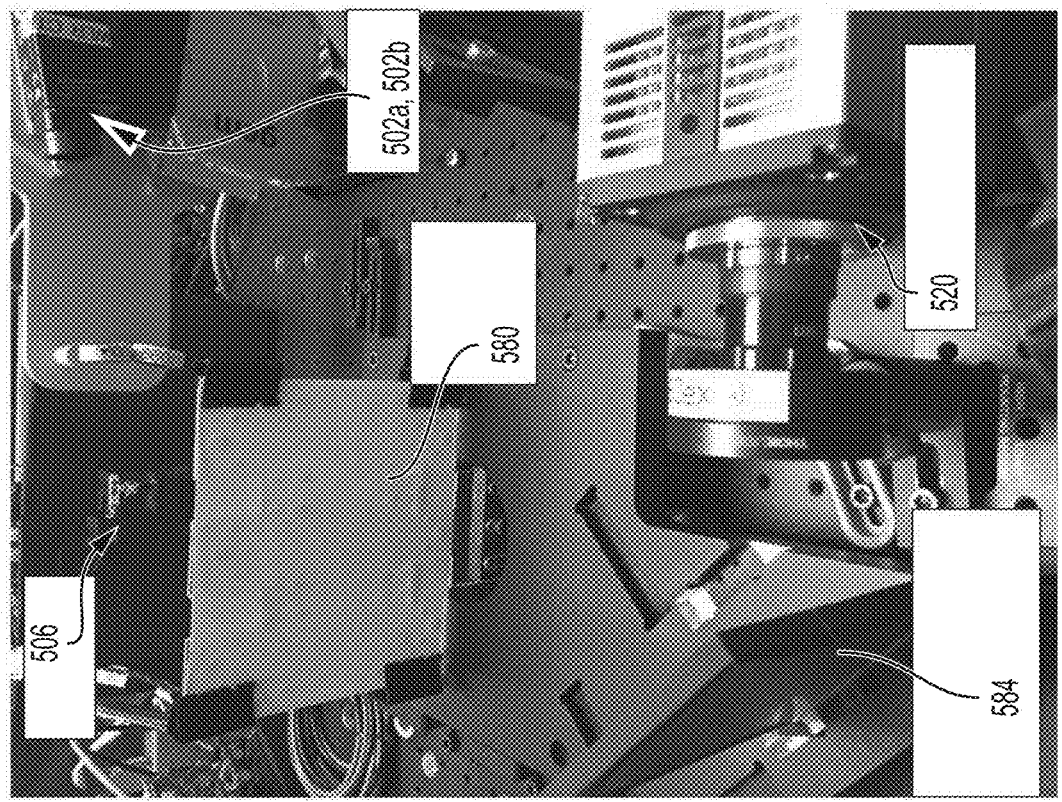

FIG. 5 shows two images of an experimental tomographic imaging system that uses the approach of simultaneously aligning multiple excitation sources described above. The system is shown in FIG. 5 with two free space lasers 502a and 502b as excitation sources. Examples of free space lasers that were used include free space diode lasers and free space diode pumped solid state (DPSS) lasers. The free space lasers used in the optical system were manufactured to directly output appropriately shaped beams of excitation light, as described above. Fiber lasers and fiber coupled lasers were also tested in the optical system. Beam shaping optics were used in combination with the fiber lasers and fiber coupled lasers to achieve desired spot sizes across the scan region.

As shown in the images of FIG. 5B, each laser was aligned to direct its beam of excitation light from its output to a two-axis galvanometer optical scanner 506 comprising two rotating galvanometer mirrors such that the beams of excitation light could be raster scanned across a two-dimensional scan region. An animal holder 580 capable of securing three small animals—mice during imaging was placed approximately at the object plane. A CCD camera 520 was aligned to image the scan area using a folding path mirror 584.

Spot sizes at the object plane were verified with a laser beam profiler at a plurality of locations within across the animal holder, within the scan region of each of the excitation sources. For each laser tested, spot sizes of the beam of excitation light within the scan region were measured to be less than 1 mm in diameter across the full scan region.

Figure 6:
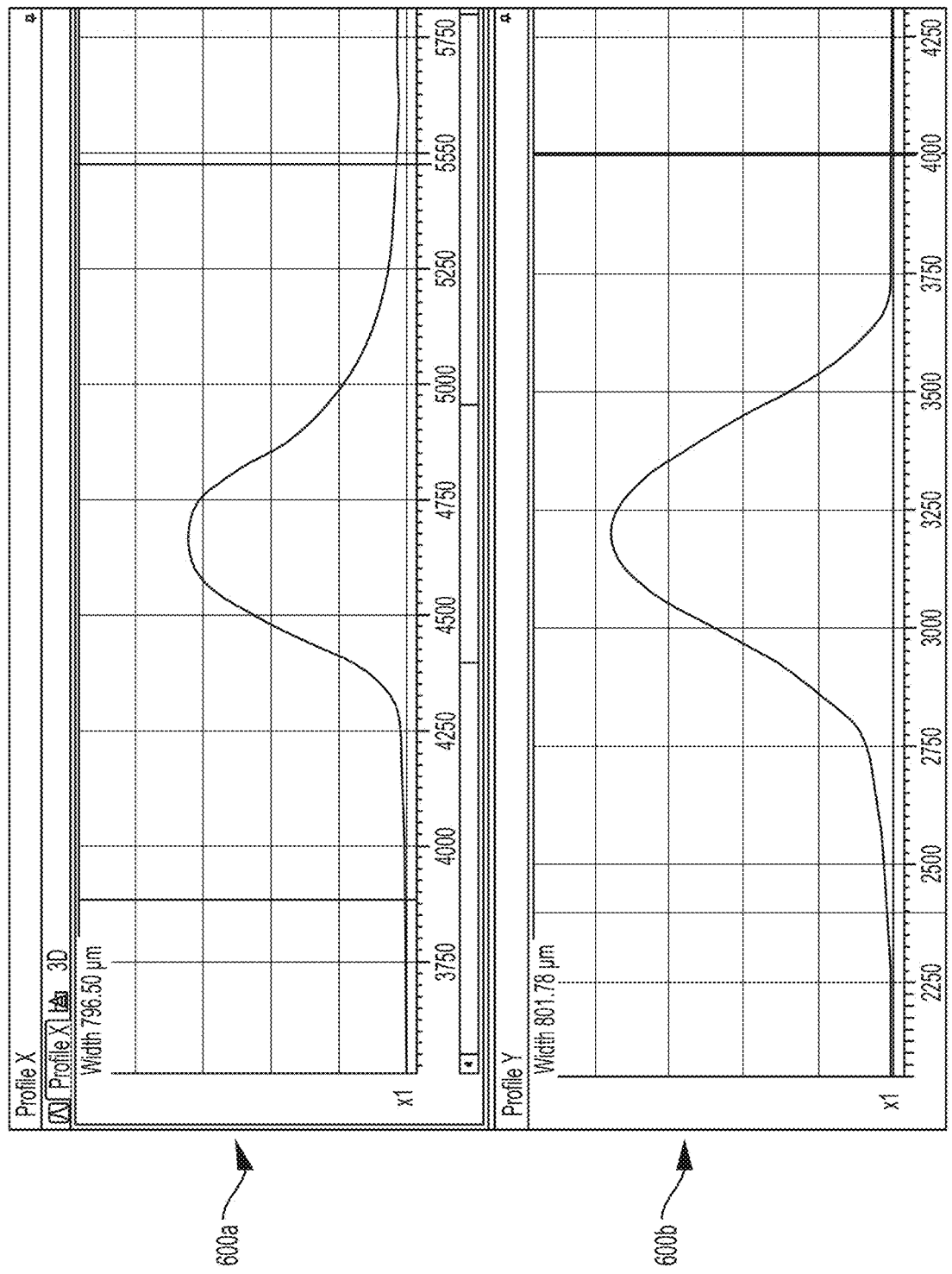
FIG. 6 is a set of plots showing linear width scans along two dimensions for a beam of excitation light from a free space diode laser, measured at an object plane, according to an illustrative embodiment.

FIG. 6 shows graphs detailed X and Y linear profiles for one of the lasers at one location within the scan region. For each of the plots 600a and 600b, the x-axis represents distance in units of μm and the y-axis represents a detected signal proportional to an intensity of the beam of excitation light at a given position. Plot 600a shows variation in the intensity of the beam of excitation light along an x-direction and plot 600b shows variation in the intensity of the beam of excitation light along a y-direction. Widths of the beam of excitation light are measured in the x and y directions as a distance between positions at which the detected signal falls to $1/e^2$ of its maximal value. As shown in FIG. 6, a width along the x-direction was measured to be 796.50 μm and a width along the y-direction was measured to be 801.78 μm, both of which are less than 1 mm.

Figure 7:
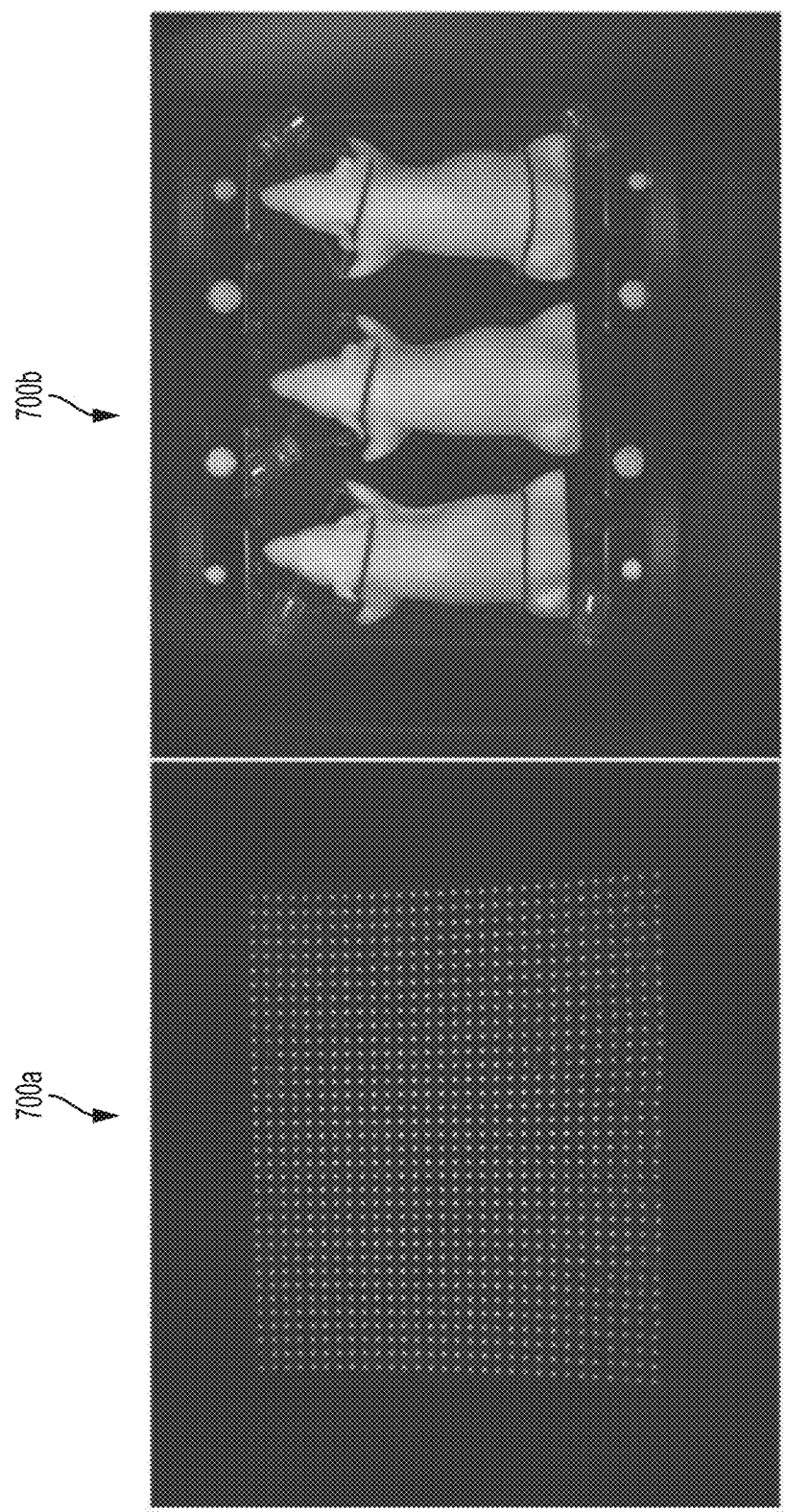
FIG. 7 is a set of two images illustrating a plurality of excitation locations within a scan region and their relation to positions of multiple subjects positioned across the object plane, according to an illustrative embodiment.

The spot size of the beam of excitation light was maintained at below 1 mm throughout the entire scan region. FIG. 7 shows two images that demonstrate the consistently small spot sizes that can be obtained throughout a plurality of excitation locations within the large scan region. Image 700a of FIG. 7 shows a plurality of excitation locations across the scan region. To obtain the image of FIG. 7A, a piece of paper was placed on the animal holder to act as a diffuse, semi-transparent substrate. An image was taken by the CCD camera for each excitation location. All the images were then stacked together, resulting in the grid-like image shown in FIG. 7A. Dark spots in the image of FIG. 7A are due to holes and other occlusions of the animal holder, and are not representative varying spot sizes. Image 700b is a bright field image of three mice secured in the animal holder. Images 700a and 700b are at the same scale and are spatially aligned, such that overlaying image 700a with image 700b illustrates the relation of the plurality of excitation locations to the positions of the three mice secured by the animal holder. Accordingly, taken together, the two images 700a and 700b show how equivalent spot sizes are met across all three animal positions.

Figure 16:
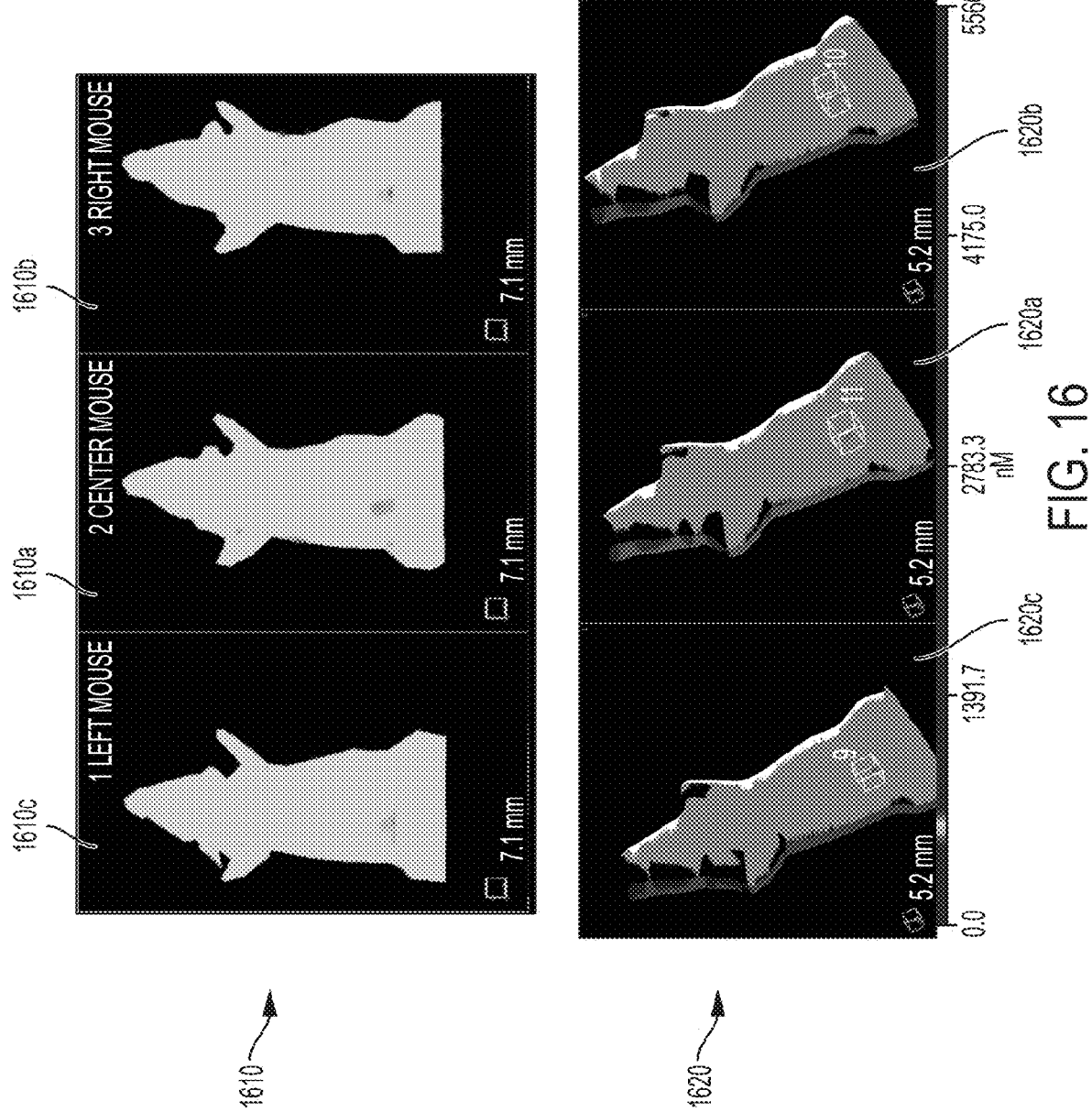
FIG. 16 is set of top and side views for three-dimensional tomographic images obtained for three mice via the beam scanning approaches described herein, according to an illustrative embodiment.

FIG. 16 shows a set of tomographic images obtained for three mouse shaped phantoms using the fast wide-field transillumination tomographic imaging approach described herein. The obtained tomographic images are 3D images showing the distribution of a fluorescent species within each of the three mouse shaped phantoms. A 3D tomographic image was obtained for each of the three mouse shaped phantoms. Top 1610 and side 1620 views of the 3D tomographic images are shown. Image 1610c is a top view of a tomographic image of mouse shaped phantom positioned on the left side of the scan region, image 1610a is a top view of a tomographic image of a mouse shaped phantom positioned at the center of the scan region and image 1610b is a top view of a tomographic image of a mouse shaped phantom positioned on the right hand side of the scan region. Image 1620c is a side view of a tomographic image of mouse shaped phantom positioned on the left side of the scan region, image 1620a is a side view of a tomographic image of a mouse shaped phantom positioned at the center of the scan region and image 1620b is a side view of a tomographic image of a mouse shaped phantom positioned on the right hand side of the scan region. The 3D tomographic images shown in FIG. 16 demonstrate the ability to perform tomographic imaging over a large scan region across which multiple subjects are positioned.

F. Applications

In certain embodiments, the systems and methods described herein provide for fast wide-field transillumination optical tomography. In certain embodiments, the approaches described herein allow for multi-subject imaging in a single scan. In certain embodiments, multiple excitation sources are used for fast wide-field tomographic imaging. In certain embodiments, the optical system layout and beam shaping approaches described herein are applicable to any system where fast wide-field scanning with point illumination (e.g., using small spot sizes) and multiple light sources is used.

G. Computer System and Network Architecture

Figure 14:
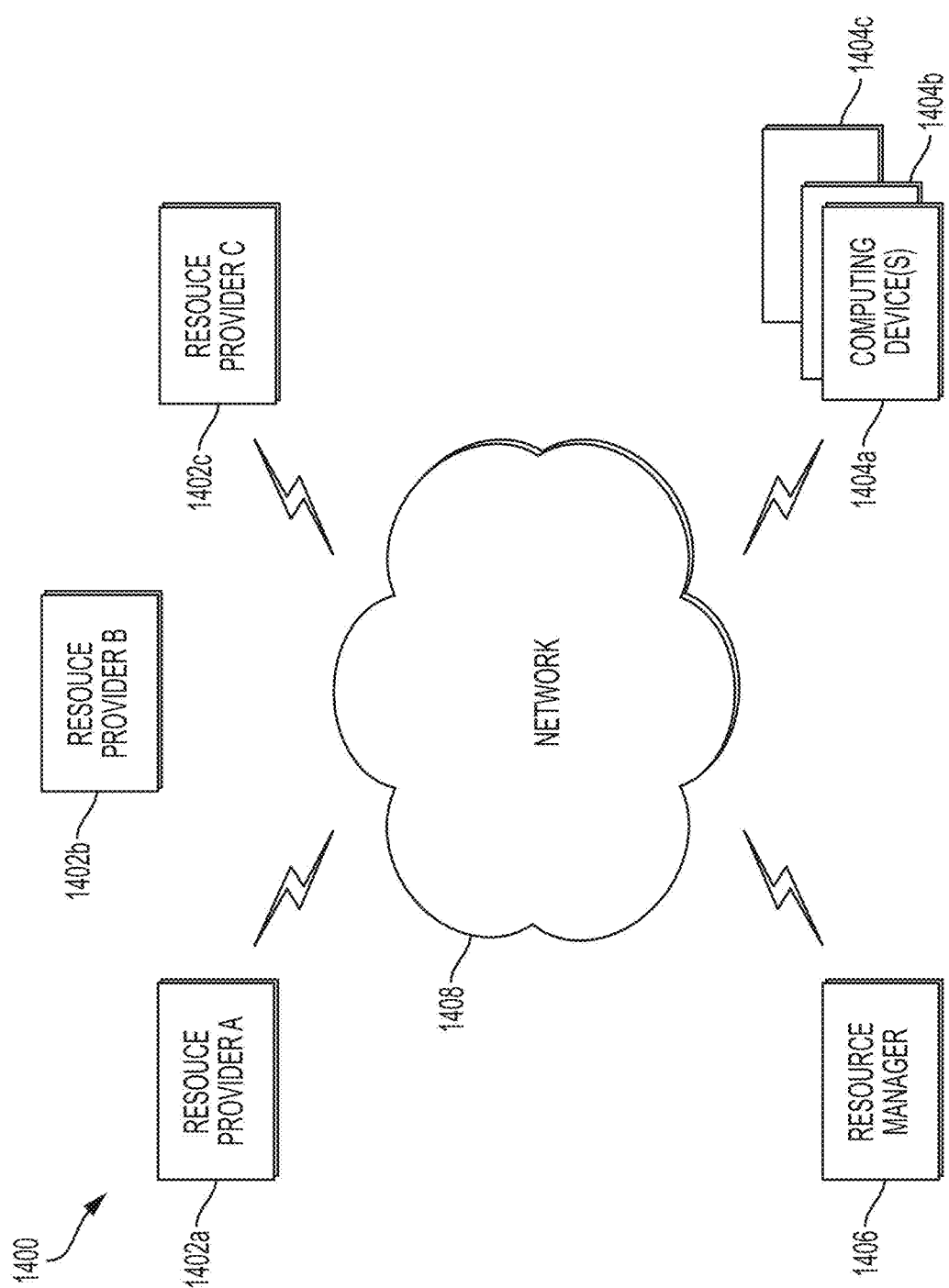
FIG. 14 is a block diagram of an exemplary cloud computing environment, used in certain embodiments.

As shown in FIG. 14, an implementation of a network environment 1400 for use in providing systems and methods for wide field trans-illumination tomographic imaging described herein is shown and described. In brief overview, referring now to FIG. 14, a block diagram of an exemplary cloud computing environment 1400 is shown and described. The cloud computing environment 1400 may include one or more resource providers 1402a, 1402b, 1402c (collectively, 1402). Each resource provider 1402 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 1402 may be connected to any other resource provider 1402 in the cloud computing environment 1400. In some implementations, the resource providers 1402 may be connected over a computer network 1408. Each resource provider 1402 may be connected to one or more computing device 1404a, 1404b, 1404c (collectively, 1404), over the computer network 1408.

The cloud computing environment 1400 may include a resource manager 1406. The resource manager 1406 may be connected to the resource providers 1402 and the computing devices 1404 over the computer network 1408. In some implementations, the resource manager 1406 may facilitate the provision of computing resources by one or more resource providers 1402 to one or more computing devices 1404. The resource manager 1406 may receive a request for a computing resource from a particular computing device 1404. The resource manager 1406 may identify one or more resource providers 1402 capable of providing the computing resource requested by the computing device 1404. The resource manager 1406 may select a resource provider 1402 to provide the computing resource. The resource manager 1406 may facilitate a connection between the resource provider 1402 and a particular computing device 1404. In some implementations, the resource manager 1406 may establish a connection between a particular resource provider 1402 and a particular computing device 1404. In some implementations, the resource manager 1406 may redirect a particular computing device 1404 to a particular resource provider 1402 with the requested computing resource.

Figure 15:
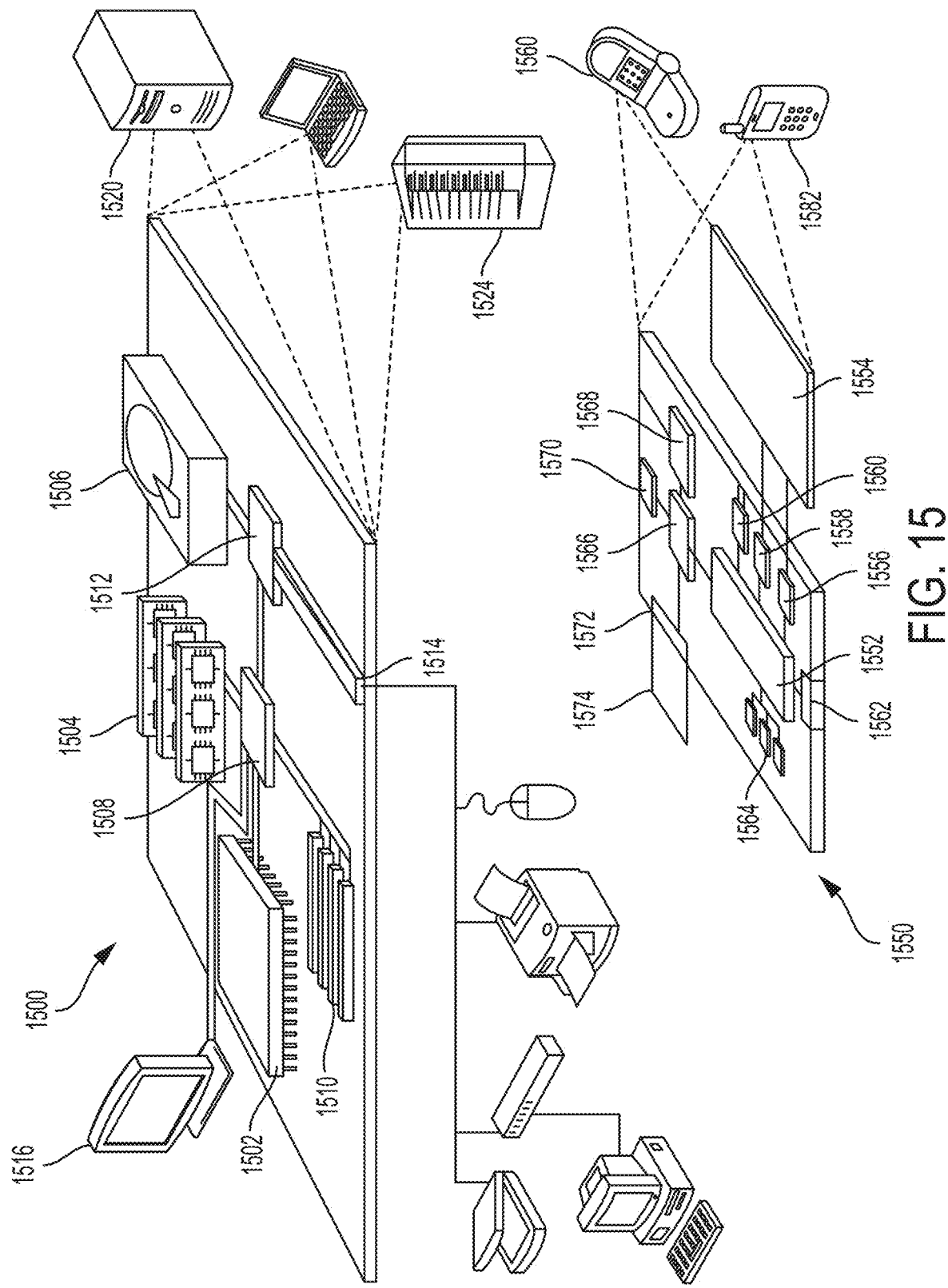
FIG. 15 is a block diagram of an example computing device and an example mobile computing device used in certain embodiments.

FIG. 15 shows an example of a computing device 1500 and a mobile computing device 1550 that can be used to implement the techniques described in this disclosure. The computing device 1500 is intended to represent various forms of digital computers, such as laptops, desktops, workstations, personal digital assistants, servers, blade servers, mainframes, and other appropriate computers. The mobile computing device 1550 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 1500 includes a processor 1502, a memory 1504, a storage device 1506, a high-speed interface 1508 connecting to the memory 1504 and multiple high-speed expansion ports 1510, and a low-speed interface 1512 connecting to a low-speed expansion port 1514 and the storage device 1506. Each of the processor 1502, the memory 1504, the storage device 1506, the high-speed interface 1508, the high-speed expansion ports 1510, and the low-speed interface 1512, are interconnected using various busses, and may be mounted on a common motherboard or in other manners as appropriate. The processor 1502 can process instructions for execution within the computing device 1500, including instructions stored in the memory 1504 or on the storage device 1506 to display graphical information for a GUI on an external input/output device, such as a display 1516 coupled to the high-speed interface 1508. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system). Thus, as the term is used herein, where a plurality of functions are described as being performed by "a processor", this encompasses embodiments wherein the plurality of functions are performed by any number of processors (one or more) of any number of computing devices (one or more). Furthermore, where a function is described as being performed by "a processor", this encompasses embodiments wherein the function is performed by any number of processors (one or more) of any number of computing devices (one or more) (e.g., in a distributed computing system).

The memory 1504 stores information within the computing device 1500. In some implementations, the memory 1504 is a volatile memory unit or units. In some implementations, the memory 1504 is a non-volatile memory unit or units. The memory 1504 may also be another form of computer-readable medium, such as a magnetic or optical disk.

The storage device 1506 is capable of providing mass storage for the computing device 1500. In some implementations, the storage device 1506 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 1502), perform one or more methods, such as those described above. The instructions can also be stored by one or more storage devices such as computer- or machine-readable mediums (for example, the memory 1504, the storage device 1506, or memory on the processor 1502).

The high-speed interface 1508 manages bandwidth-intensive operations for the computing device 1500, while the low-speed interface 1512 manages lower bandwidth-intensive operations. Such allocation of functions is an example only. In some implementations, the high-speed interface 1508 is coupled to the memory 1504, the display 1516 (e.g., through a graphics processor or accelerator), and to the high-speed expansion ports 1510, which may accept various expansion cards (not shown). In the implementation, the low-speed interface 1512 is coupled to the storage device 1506 and the low-speed expansion port 1514. The low-speed expansion port 1514, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 1500 may be implemented in a number of different forms, as shown in the figure. For example, it may be implemented as a standard server 1520, or multiple times in a group of such servers. In addition, it may be implemented in a personal computer such as a laptop computer 1522. It may also be implemented as part of a rack server system 1524. Alternatively, components from the computing device 1500 may be combined with other components in a mobile device (not shown), such as a mobile computing device 1550. Each of such devices may contain one or more of the computing device 1500 and the mobile computing device 1550, and an entire system may be made up of multiple computing devices communicating with each other.

The mobile computing device 1550 includes a processor 1552, a memory 1564, an input/output device such as a display 1554, a communication interface 1566, and a transceiver 1568, among other components. The mobile computing device 1550 may also be provided with a storage device, such as a micro-drive or other device, to provide additional storage. Each of the processor 1552, the memory 1564, the display 1554, the communication interface 1566, and the transceiver 1568, are interconnected using various buses, and several of the components may be mounted on a common motherboard or in other manners as appropriate.

The processor 1552 can execute instructions within the mobile computing device 1550, including instructions stored in the memory 1564. The processor 1552 may be implemented as a chipset of chips that include separate and multiple analog and digital processors. The processor 1552 may provide, for example, for coordination of the other components of the mobile computing device 1550, such as control of user interfaces, applications run by the mobile computing device 1550, and wireless communication by the mobile computing device 1550.

The processor 1552 may communicate with a user through a control interface 1558 and a display interface 1556 coupled to the display 1554. The display 1554 may be, for example, a TFT (Thin-Film-Transistor Liquid Crystal Display) display or an OLED (Organic Light Emitting Diode) display, or other appropriate display technology. The display interface 1556 may comprise appropriate circuitry for driving the display 1554 to present graphical and other information to a user. The control interface 1558 may receive commands from a user and convert them for submission to the processor 1552. In addition, an external interface 1562 may provide communication with the processor 1552, so as to enable near area communication of the mobile computing device 1550 with other devices. The external interface 1562 may provide, for example, for wired communication in some implementations, or for wireless communication in other implementations, and multiple interfaces may also be used.

The memory 1564 stores information within the mobile computing device 1550. The memory 1564 can be implemented as one or more of a computer-readable medium or media, a volatile memory unit or units, or a non-volatile memory unit or units. An expansion memory 1574 may also be provided and connected to the mobile computing device 1550 through an expansion interface 1572, which may include, for example, a SIMM (Single In Line Memory Module) card interface. The expansion memory 1574 may provide extra storage space for the mobile computing device 1550, or may also store applications or other information for the mobile computing device 1550. Specifically, the expansion memory 1574 may include instructions to carry out or supplement the processes described above, and may include secure information also. Thus, for example, the expansion memory 574 may be provide as a security module for the mobile computing device 1550, and may be programmed with instructions that permit secure use of the mobile computing device 1550. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. that the instructions, when executed by one or more processing devices (for example, processor 1552), perform one or more methods, such as those described above. The instructions can also be stored by one or more storage devices, such as one or more computer- or machine-readable mediums (for example, the memory 1564, the expansion memory 1574, or memory on the processor 1552). In some implementations, the instructions can be received in a propagated signal, for example, over the transceiver 1568 or the external interface 1562.

The mobile computing device 1550 may communicate wirelessly through the communication interface 1566, which may include digital signal processing circuitry where necessary. The communication interface 1566 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 1568 using a radio-frequency. In addition, short-range communication may occur, such as using a Bluetooth®, Wi-Fi™, or other such transceiver (not shown). In addition, a GPS (Global Positioning System) receiver module 1570 may provide additional navigation- and location-related wireless data to the mobile computing device 1550, which may be used as appropriate by applications running on the mobile computing device 1550.

The mobile computing device 1550 may also communicate audibly using an audio codec 1560, which may receive spoken information from a user and convert it to usable digital information. The audio codec 1560 may likewise generate audible sound for a user, such as through a speaker, e.g., in a handset of the mobile computing device 1550. Such sound may include sound from voice telephone calls, may include recorded sound (e.g., voice messages, music files, etc.) and may also include sound generated by applications operating on the mobile computing device 1550.

The mobile computing device 1550 may be implemented in a number of different forms, as shown in the figure. For example, it may be implemented as a cellular telephone 1580. It may also be implemented as part of a smart-phone 1582, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, any modules described herein can be separated, combined or incorporated into single or combined modules. Any modules depicted in the figures are not intended to limit the systems described herein to the software architectures shown therein.

Elements of different implementations described herein may be combined to form other implementations not specifically set forth above. Elements may be left out of the processes, computer programs, databases, etc. described herein without adversely affecting their operation. In addition, the logic flows depicted in the figures do not require the particular order shown, or sequential order, to achieve desirable results. Various separate elements may be combined into one or more individual elements to perform the functions described herein. In view of the structure, functions and apparatus of the systems and methods described here, in some implementations.

Throughout the description, where apparatus and systems are described as having, including, or comprising specific components, or where processes and methods are described as having, including, or comprising specific steps, it is contemplated that, additionally, there are apparatus, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A system for fast scanning of excitation light over a wide field of view for tomographic imaging of a plurality of subjects positioned across an object plane, the system comprising:
   (a) an excitation source operable to emit a beam of excitation light, wherein the excitation source is aligned to direct the beam of excitation light along an optical path from an output of the excitation source to a galvanometer optical scanner comprising one or more rotating galvanometer mirrors;
   (b) the galvanometer optical scanner, wherein the galvanometer optical scanner is aligned and operable to direct, during an exposure of the plurality of subjects to the beam of excitation light, the beam of excitation light to a plurality of discrete excitation locations within a scan region of the object plane via reflection by the one or more rotating galvanometer mirrors, such that as the one or more galvanometer mirrors are rotated, the beam of excitation light is scanned across the scan region, thereby providing for illumination of the plurality of subjects positioned across the object plane,
      wherein the plurality of discrete excitation locations comprise a plurality of multi-subject sets of discrete excitation locations, and wherein each of the multi-subject sets of discrete excitation locations comprises a first discrete excitation location corresponding to a first location of a first subject of the plurality of subjects and a second discrete excitation location corresponding to a second location of a second subject of the plurality of subjects, and
      wherein the plurality of subjects are within the scan region and are statically fixed to the object plane as the one or more galvanometer mirrors are rotated;
   (c) one or more detectors aligned and operable to detect, during the exposure of the plurality of subjects to the beam of excitation light, fluorescent light emitted from one or more fluorescent species of the plurality of subjects as a result of excitation by the beam of excitation light at the first discrete excitation location and at the second discrete excitation location of one of the plurality of multi-subject sets of discrete excitation locations;
   (d) a processor; and
   (e) a memory having instructions stored thereon, wherein the instructions, when executed by the processor cause the processor to:
      receive and/or access data corresponding to the detected fluorescent light; and
      obtain one or more tomographic images of the plurality of subjects using the data corresponding to the detected fluorescent light, wherein the one or more tomographic images comprises a multi-subject tomographic image that represents the fluorescent light emitted from the plurality of subjects at the first discrete excitation location and the second discrete excitation location of one of the plurality of multi-subject sets of discrete excitation locations.

2. The system of claim 1, wherein a position of the galvanometer optical scanner is based on one or more maximal rotational angles of the one or more galvanometer mirrors.

3. The system of claim 1, wherein a minimal distance along a minimal length optical path from the galvanometer optical scanner to a location within the scan region is from 150 to 250 mm.

4. The system of claim 1, wherein the excitation source is operable to emit the beam of excitation light from its output as a focused beam of excitation light that converges as it travels (i) towards the galvanometer optical scanner and (ii) from the galvanometer optical scanner to the object plane.

5. The system of claim 4, wherein the focused beam of excitation light emitted from the output of the excitation source has a spot size less than or approximately equal to 1 mm at all locations within the scan region.

6. The system of claim 5, wherein a half-angle divergence of the focused beam of excitation light emitted from the output of the excitation source is less than or equal to 25 mrad.

7. The system of claim 4, wherein the focused beam of excitation light emitted from the output of the excitation source has a half-angle divergence, φ, such that $$\tan(\varphi) < \frac{w_{max} - w_{bw}}{d_2 - d_1},$$

wherein:
   $W_{max}$ is an upper bound for a desired spot size of the beam of excitation light within the scan region,
   $W_{bw}$ is a spot size of the beam of excitation light at its beam waist location, $d_1$ is a minimal distance measured along a minimal length optical path from the galvanometer optical scanner to a location within the scan region, and $d_2$ is a maximal distance along a maximal length optical path from the galvanometer optical scanner to a location within the scan region.

8. The system of claim 1, wherein the system comprises a beam shaping optic positioned in the optical path from the output of the excitation source to the galvanometer optical scanner, wherein the beam shaping optic is at least one of:

(A) a focusing optic, wherein the focusing optic is aligned such that after passing through the focusing optic, the beam of excitation light converges as it travels (i) towards the galvanometer optical scanner and (ii) from the galvanometer optical scanner to the object plane; and (B) a collimating optic, wherein the collimating optic is aligned such that after passing through the collimating optic, the beam of excitation light diverges as it travels (i) towards the galvanometer optical scanner and (ii) from the galvanometer optical scanner to the object plane.

9. The system of claim 8, wherein the beam shaping optic is the focusing optic.

10. The system of claim 9, wherein the focusing optic is positioned such that a spot size of the beam of excitation light is less than or approximately equal to 1 mm in diameter at all locations within the scan region.

11. The system of claim 9, wherein a half-angle divergence, φ, of the beam of excitation light after passing through the focusing optic is such that tan $$\tan(\varphi) < \frac{w_{max} - w_{bw}}{d_2 - d_1},$$

wherein:

$W_{max}$ is an upper bound for a desired spot size of the beam of excitation light, $W_{bw}$ is a spot size of the beam of excitation light at a beam waist, $d_1$ is a minimal distance along a minimal length optical path from the galvanometer optical scanner to a location within the scan region, and $d_2$ is a maximal distance along a maximal length optical path from the galvanometer optical scanner to a location within the scan region.

12. The system of claim 9, wherein a half-angle divergence of the beam of excitation light after passing through the focusing optic is less than or equal to 25 mrad.

13. The system of claim 1, wherein a power of the excitation source is greater than or approximately equal to 100 mW.

14. The system of claim 1, wherein the excitation source is a fiber coupled laser or a fiber laser, and the output of the excitation source from which the beam of excitation light is emitted is a distal end of an optical fiber of the fiber coupled laser or the fiber laser.

15. The system of claim 14, wherein a core diameter of the optical fiber of the fiber coupled laser or the fiber laser is from 5 μm to 400 μm.

16. The system of claim 14, wherein a numerical aperture (NA) of the optical fiber is from 0.1 to 0.3.

17. The system of claim 1, wherein the one or more detectors are aligned and operable to detect the fluorescent light emitted from the fluorescent species in a transillumination geometry, wherein the beam of excitation light is directed towards the object plane from a first side of the object plane and the one or more detectors are aligned and operable to detect fluorescent light emitted in directions outwards from an opposite second side of the object plane.

18. The system of claim 1, wherein:

the one or more detectors are aligned and operable to detect excitation light transmitted through or reflected from the plurality of subjects, and the instructions cause the processor to:
receive and/or access data corresponding to the detected excitation light; and
obtain, one or more tomographic images of the plurality of subjects using the data corresponding to the detected excitation light and the data corresponding to the detected fluorescent light.

19. The system of claim 1, wherein:

for each discrete excitation location of the plurality of discrete excitation locations:
a given subject of the plurality of subjects that is positioned in the path of the beam of excitation light directed towards the discrete excitation location is illuminated by the beam of excitation light at a corresponding illumination location on a surface of the given subject, such that the beam of excitation light is incident on the surface of the given subject at the corresponding illumination location and diffuses within the given subject, thereby providing for excitation of a fluorescent species within the given subject, and
the one or more detectors are aligned and operable to detect a corresponding fluorescence emission image representing detected fluorescent light emitted by the fluorescent species within the given subject that is positioned in the path of the beam of excitation light directed to the discrete excitation location, thereby providing for detection of a plurality of fluorescence emission images, each fluorescence emission image of the plurality of fluorescence emission images corresponding to a discrete excitation location of the plurality of discrete excitation locations, and the instructions cause the processor to:
receive and/or access the data corresponding to the detected fluorescent light at least by receiving and/or accessing the plurality of fluorescence emission images; and
obtain the one or more tomographic images of the plurality of subjects using the plurality of fluorescence emission images.

20. The system of claim 19, wherein:

the one or more detectors are aligned and operable to detect, for each discrete excitation location of the plurality of discrete excitation locations,
a corresponding excitation image representing excitation light transmitted through or reflected by the given subject when the beam of excitation light is incident on the surface of the given subject at the corresponding illumination location, such that a plurality of excitation images are detected, each excitation image of the plurality of excitation images corresponding to a discrete excitation location of the plurality of discrete excitation locations, and the instructions cause the processor to:
receive and/or access data corresponding to detected excitation light, the data corresponding to the detected excitation light comprising the plurality of excitation images; and obtain the one or more tomographic images of the plurality of subjects using the plurality of fluorescence emission images and the plurality of excitation images.

21. The system of claim 1, wherein:
the galvanometer optical scanner is operable to scan the beam of excitation light one multi-subject set of the plurality of multi-subject sets at a time, by directing the beam of excitation light to each discrete excitation location within a given multi-subject set of the plurality of multi-subject sets before proceeding to direct the beam of excitation light to any discrete excitation location of any other multi-subject set of the plurality of multi-subject sets, and
the galvanometer optical scanner is operable to scan the beam of excitation light through each discrete excitation location of each multi-subject set of the plurality of multi-subject sets within a time corresponding to an exposure window of the one or more detectors, and
the one or more detectors are aligned and operable to detect, for each multi-subject set of the plurality of multi-subject sets, a corresponding fluorescence emission image representing detected fluorescent light emitted during the exposure window of the one or more detectors as a result of excitation of the one or more fluorescent species within the plurality of subjects by excitation light directed to each discrete excitation location within the given multi-subject set of the plurality of multi-subject sets.

22. The system of claim 21, wherein:
the data corresponding to the detected fluorescent light comprises, for each multi-subject set of the plurality of multi-subject sets, the corresponding fluorescence emission image, and
the instructions cause the processor to obtain a tomographic image for each subject of the plurality of subjects using the fluorescence emission images.

23. The system of claim 22, wherein the instructions cause the processor to, for each subject of the plurality of subjects:
for each fluorescence emission image corresponding to a multi-subject set of the plurality of multi-subject sets, determine a portion of the fluorescence emission image associated with the first subject or the second subject,
thereby determining one or more single subject fluorescence emission images for the plurality of subjects, wherein each single subject fluorescence image corresponds to a multi-subject set of the plurality of multi-subject sets; and
obtain a tomographic image of the first subject or the second subject using the one or more single subject fluorescence emission images associated with the first subject or the second subject.

24. The system of claim 21, wherein:
the one or more detectors are aligned and operable to detect, for each multi-subject set of the plurality of multi-subject sets,
a corresponding excitation image representing excitation light transmitted through or reflected by the plurality of subjects detected during the exposure window of the one or more detectors as a result of illumination of the plurality of subjects by the beam of excitation light directed to each discrete excitation location within the given multi-subject set of the plurality of multi-subject sets, and the instructions cause the processor to:
receive and/or access data corresponding to the detected excitation light, the data corresponding to the detected excitation light comprising, for each multi-subject set of the plurality of multi-subject sets, the corresponding excitation image; and
obtain a tomographic image for each subject of the plurality of subjects using the detected fluorescence emission images and the detected excitation images.

25. The system of claim 24, wherein the instructions cause the processor to, for each subject of the plurality of subjects:
for each fluorescence emission image corresponding to a multi-subject set of the plurality of multi-subject sets, determine a portion of the fluorescence emission image associated with the first subject or the second subject, thereby determining a single subject fluorescence emission image associated with the first subject or the second subject and corresponding to the multi-subject set, thereby determining one or more single subject fluorescence emission images associated with the first subject or the second subject, wherein each single subject fluorescence emission image corresponds to the multi-subject set;
for each excitation image corresponding to the multi-subject set,
determine a portion of the excitation image associated with the first subject or the second subject, thereby determining a single subject excitation image associated with the first subject or the second subject and corresponding to the multi-subject set, thereby determining one or more single subject excitation images associated with the first subject or the second subject, wherein each single subject excitation image corresponds to the multi-subject set; and
obtain a tomographic image of the first subject or the second subject using the one or more single subject fluorescence emission images associated with the first subject or the second subject and the one or more single subject excitation images associated with the first subject or the second subject.

26. The system of claim 1, wherein a power of the excitation source is between 100 mW and 200 mW.

27. The system of claim 1, wherein a subject of the plurality of subjects comprises a mouse, a rat, a vole, a rabbit, or a hamster.

28. The system of claim 1 wherein:
the plurality of multi-subject sets of discrete excitation locations comprises a first multi-subject set of discrete excitation locations and a second multi-subject set of discrete excitation locations;
the first discrete excitation location of the first multi-subject set of discrete excitation locations is different from the first discrete excitation location of the second multi-subject set of discrete excitation locations; and
the second discrete excitation location of the first multi-subject set of discrete excitation locations is different from the second discrete excitation location of the second multi-subject set of discrete excitation locations.

29. A system for fast scanning of excitation light from a plurality of excitation sources over a wide field of view for tomographic imaging of a plurality of subjects positioned across an object plane, the system comprising:
(a) a plurality of excitation sources, wherein:
each excitation source is operable to emit a respective beam of excitation light, a first excitation source is aligned to direct its respective beam of excitation light along a first optical path from an output of the first excitation source to a galvanometer optical scanner comprising one or more rotating galvanometer mirrors, and each excitation source other than the first excitation source is aligned to direct its respective beam of excitation light along a respective optical path from its output to the galvanometer optical scanner at a corresponding offset angle with respect to the first optical path;

(b) the galvanometer optical scanner, wherein the galvanometer optical scanner is aligned and operable to, for each excitation source, direct, during an exposure of the plurality of subjects to the respective beam of excitation light, the respective beam of excitation light to a respective plurality of discrete excitation locations within a respective scan region of the object plane via reflection by the one or more rotating galvanometer mirrors, such that as the one or more galvanometer mirrors are rotated, the respective beam of excitation light is scanned across the respective scan region, thereby providing for illumination of the plurality of subjects positioned across the object plane, wherein the respective plurality of discrete excitation locations comprise a plurality of multi-subject sets of discrete excitation locations, and wherein each of the multi-subject sets of discrete excitation locations comprises a first discrete excitation location corresponding to a first location of a first subject of the plurality of subjects and a second discrete excitation location corresponding to a second location of a second subject of the plurality of subjects, and wherein the plurality of subjects are statically fixed to the object plane as the one or more galvanometer mirrors are rotated;

(c) one or more detectors aligned and operable to detect, during the exposure of the plurality of subjects to the respective beam of excitation light, fluorescent light emitted from one or more fluorescent species of the plurality of subjects as a result of excitation by the respective beam of excitation light at the first discrete excitation location and at the second discrete excitation location of one of the plurality of multi-subject sets of discrete excitation locations;

(d) a processor; and (e) a memory having instructions stored thereon, wherein the instructions, when executed by the processor cause the processor to:

receive and/or access data corresponding to the detected fluorescent light; and obtain one or more tomographic images of the plurality of subjects using the data corresponding to the detected fluorescent light, wherein the one or more tomographic images comprises a multi-subject tomographic image that represents the fluorescent light emitted from the plurality of subjects at the first discrete excitation location and the second discrete excitation location of one of the plurality of multi-subject sets of discrete excitation locations.

30. The system of claim 29, wherein each excitation source of the plurality of excitation sources emits excitation light having a distinct excitation wavelength within an excitation band of a corresponding fluorescent species within the plurality of subjects.

31. The system of claim 29, wherein the one or more detectors are aligned and operable to detect fluorescent light emitted from the one or more fluorescent species within the plurality of subjects as a result of excitation by the excitation light from each of two or more excitation sources of the plurality of excitation sources.

32. The system of claim 29, wherein:

the data corresponding to the detected fluorescent light comprises, for each of two or more excitation sources of the plurality of excitation sources, a set of associated fluorescence emission signals detected following excitation by excitation light directed towards each of the respective plurality of discrete excitation locations across the respective scan region of the excitation source, and the instructions cause the processor to, for each of the two or more excitation sources, obtain a respective set of one or more tomographic images of the plurality of subjects using the associated fluorescence emission signals, thereby obtaining a set of one or more tomographic images for each of the two or more excitation sources.

33. The system of claim 29, wherein at least a portion of each of the respective scan regions of each of the excitation sources overlap with each other to produce a shared scan region.

34. The system of claim 33, wherein the position of the galvanometer optical scanner is based on one or more maximal rotational angles of the one or more galvanometer mirrors.

35. A method for fast scanning of excitation light over a wide field of view for tomographic imaging of a plurality of subjects positioned across an object plane, the method comprising:

(a) illuminating the plurality of subjects with a beam of excitation light from an excitation source, wherein the excitation source is aligned to direct the beam of excitation light along an optical path from an output of the excitation source to a galvanometer optical scanner comprising one or more rotating galvanometer mirrors, wherein the galvanometer optical scanner is aligned and operable to direct, during an exposure of the plurality of subjects to the beam of excitation light, the beam of excitation light to a plurality of discrete excitation locations within a scan region of the object plane via reflection by the one or more rotating galvanometer mirrors, such that as the one or more galvanometer mirrors are rotated, the beam of excitation light is scanned across the scan region, thereby providing for illumination of the plurality of subjects positioned across the object plane, wherein the plurality of discrete excitation locations comprise a plurality of multi-subject sets of discrete excitation locations, and wherein each of the multi-subject sets of discrete excitation locations comprises a first discrete excitation location corresponding to a first location of a first subject of the plurality of subjects and a second discrete excitation location corresponding to a second location of a second subject of the plurality of subjects, and wherein the plurality of subjects are within the scan region and are statically fixed to the object plane as the one or more galvanometer mirrors are rotated;

(b) detecting, with one or more detectors and during the exposure of the plurality of subjects to the beam of excitation light, fluorescent light emitted from a fluorescent species within the plurality of subjects as a result of excitation by the beam of excitation light at the first discrete excitation location and at the second discrete excitation location of one of the plurality of multi-subject sets of discrete excitation locations;

(c) receiving and/or accessing, by a processor of a computing device, data corresponding to the detected fluorescent light; and (d) obtaining, by the processor, one or more tomographic images of the plurality of subjects using the data corresponding to the detected fluorescent light, wherein the one or more tomographic images comprises a multi-subject tomographic image that represents the fluorescent light emitted from the plurality of subjects at the first discrete excitation location and the second discrete excitation location of one of the plurality of multi-subject sets of discrete excitation locations.

36. A method for fast scanning of excitation light from a plurality of excitation sources over a wide field of view for tomographic imaging of a plurality of subjects positioned across an object plane, the method comprising:

(a) illuminating the plurality of subjects with at least one beam of excitation light emitted by a respective one of a plurality of excitation sources, wherein:
  (i) a first excitation source is aligned to direct its respective beam of excitation light along a first optical path from the first excitation source to a galvanometer optical scanner comprising one or more rotating galvanometer mirrors,
  (ii) each excitation source other than the first excitation source is aligned to direct its respective beam of excitation light along an respective optical path towards the galvanometer optical scanner at a corresponding offset angle with respect to the first optical path from the first excitation source to the galvanometer optical scanner,
  (iii) the galvanometer optical scanner is aligned and operable to, for each excitation source, direct, during an exposure of the plurality of subjects to the respective beam of excitation light, the respective beam of excitation light to a respective plurality of discrete excitation locations within a respective scan region of the object plane via reflection by the one or more rotating galvanometer mirrors, such that as the one or more galvanometer mirrors are rotated, the respective beam of excitation light is scanned across the respective scan region, thereby providing for illumination of the plurality of subjects positioned across the object plane,
    wherein the respective plurality of discrete excitation locations comprise a plurality of multi-subject sets of discrete excitation locations, and wherein each of the multi-subject sets of discrete excitation locations comprises a first discrete excitation location corresponding to a first location of a first subject of the plurality of subjects and a second discrete excitation location corresponding to a second location of a second subject of the plurality of subjects, and
    wherein the plurality of subjects are within the scan region and are statically fixed to the object plane as the one or more galvanometer mirrors are rotated;

(b) detecting, with one or more detectors and during the exposure of the plurality of subjects to the respective beam of excitation light, fluorescent light emitted from one or more fluorescent species of the plurality of subjects as a result of excitation by the respective beam of excitation light at the first discrete excitation location and at the second discrete excitation location of one of the plurality of multi-subject sets of discrete excitation locations;

(c) receiving and/or accessing, by a processor of a computing device, data corresponding to the detected fluorescent light; and (d) obtaining, by the processor, one or more tomographic images of the plurality of subjects using the data corresponding to the detected fluorescent light, wherein the one or more tomographic images comprises a multi-subject tomographic image that represents the fluorescent light emitted from the plurality of subjects at the first discrete excitation location and the second discrete excitation location of one of the plurality of multi-subject sets of discrete excitation locations.

* * * * *